US008721562B2

(12) United States Patent
Abreu

(10) Patent No.: US 8,721,562 B2
(45) Date of Patent: *May 13, 2014

(54) APPARATUS AND METHOD FOR MEASURING BIOLOGIC PARAMETERS

(75) Inventor: Marcio Marc Abreu, New Haven, CT (US)

(73) Assignee: Geelux Holdings, Ltd., Tortola (VG)

( * ) Notice: Subject to any disclaimer, the term of this patent is extended or adjusted under 35 U.S.C. 154(b) by 2027 days.

This patent is subject to a terminal disclaimer.

(21) Appl. No.: 11/713,671

(22) Filed: Mar. 5, 2007

(65) Prior Publication Data
US 2007/0219434 A1    Sep. 20, 2007

Related U.S. Application Data

(62) Division of application No. 10/420,295, filed on Apr. 22, 2003, now Pat. No. 7,187,960.

(60) Provisional application No. 60/374,133, filed on Apr. 22, 2002.

(51) Int. Cl.
 *A61B 5/00* (2006.01)
 *A61B 5/103* (2006.01)
 *A61B 5/117* (2006.01)

(52) U.S. Cl.
USPC ........... 600/549; 600/300; 600/301; 600/309; 600/310; 600/340; 600/587; 600/595

(58) Field of Classification Search
USPC ......... 600/549, 587, 595, 300, 301, 309, 310, 600/340
See application file for complete search history.

(56) References Cited

U.S. PATENT DOCUMENTS 3,545,260 A    12/1970   Lichtenstein et al.
3,585,849 A     6/1971   Grolman
(Continued)

FOREIGN PATENT DOCUMENTS

DE    44 33 104     5/1996
EP    0 236 028     9/1987
(Continued)

OTHER PUBLICATIONS

RCA Technical Notes, Contact Lens Tonometer by Robert E. Morey, RCA TN No. 602, dated Dec. 1964, 2 Pages.
(Continued)

*Primary Examiner* — Rene Towa
*Assistant Examiner* — May Abouelela
(74) *Attorney, Agent, or Firm* — Studebaker & Brackett PC

(57) ABSTRACT

Support structures for positioning sensors on a physiologic tunnel for measuring physical, chemical and biological parameters of the body and to produce an action according to the measured value of the parameters. The support structure includes a sensor fitted on the support structures using a special geometry for acquiring continuous and undisturbed data on the physiology of the body. Signals are transmitted to a remote station by wireless transmission such as by electromagnetic waves, radio waves, infrared, sound and the like or by being reported locally by audio or visual transmission. The physical and chemical parameters include brain function, metabolic function, hydrodynamic function, hydration status, levels of chemical compounds in the blood, and the like. The support structure includes patches, clips, eyeglasses, head mounted gear and the like, containing passive or active sensors positioned at the end of the tunnel with sensing systems positioned on and accessing a physiologic tunnel.

3 Claims, 53 Drawing Sheets

(56) References Cited

U.S. PATENT DOCUMENTS

| | | | |
|---|---|---|---|
| 3,724,263 A | | 4/1973 | Rose et al. |
| 3,769,961 A | | 11/1973 | Fatt |
| 3,963,019 A | | 6/1976 | Quandt |
| 4,186,184 A | | 1/1980 | Zaffaroni |
| 4,297,685 A | * | 10/1981 | Brainard, II ................ 340/575 |
| 4,305,399 A | | 12/1981 | Beale |
| 4,312,358 A | * | 1/1982 | Barney ......................... 600/483 |
| 4,321,261 A | | 3/1982 | Ellis et al. |
| 4,330,299 A | | 5/1982 | Cerami |
| 4,344,438 A | | 8/1982 | Schultz |
| 4,386,831 A | | 6/1983 | Grounauer |
| 4,485,820 A | | 12/1984 | Flower |
| 4,488,558 A | * | 12/1984 | Simbruner et al. .......... 600/376 |
| 4,597,392 A | | 7/1986 | Opitz et al. |
| 4,628,938 A | | 12/1986 | Lee |
| 4,629,424 A | | 12/1986 | Lauks et al. |
| 4,771,792 A | | 9/1988 | Seale |
| 4,784,149 A | | 11/1988 | Berman et al. ................ 128/664 |
| 4,830,014 A | * | 5/1989 | Goodman et al. ........... 600/310 |
| 4,860,755 A | | 8/1989 | Erath |
| 4,922,913 A | | 5/1990 | Waters et al. |
| 4,944,303 A | | 7/1990 | Katsuragi |
| 4,947,849 A | | 8/1990 | Takahashi et al. |
| 4,951,671 A | | 8/1990 | Coan |
| 5,005,577 A | | 4/1991 | Frenkel |
| 5,062,432 A | | 11/1991 | James et al. |
| 5,076,274 A | | 12/1991 | Matsumoto |
| 5,109,852 A | | 5/1992 | Kaye et al. |
| 5,115,815 A | | 5/1992 | Hansen |
| 5,148,807 A | | 9/1992 | Hsu |
| 5,165,409 A | | 11/1992 | Coan |
| 5,179,953 A | | 1/1993 | Kursar |
| 5,183,044 A | | 2/1993 | Nishio et al. |
| 5,190,039 A | * | 3/1993 | Takeuchi et al. ............. 600/311 |
| 5,209,231 A | | 5/1993 | Cote et al. |
| 5,217,015 A | | 6/1993 | Kaye et al. |
| 5,222,495 A | | 6/1993 | Clarke et al. |
| 5,246,867 A | | 9/1993 | Lakowicz et al. |
| 5,251,627 A | | 10/1993 | Morris |
| 5,295,495 A | | 3/1994 | Maddess |
| 5,297,554 A | | 3/1994 | Glynn et al. |
| 5,341,805 A | | 8/1994 | Stavridi et al. |
| 5,342,283 A | | 8/1994 | Good |
| 5,342,789 A | | 8/1994 | Chick et al. |
| 5,352,411 A | | 10/1994 | Khuri |
| 5,356,780 A | | 10/1994 | Robinson et al. |
| 5,375,595 A | | 12/1994 | Sinha et al. |
| 5,383,452 A | | 1/1995 | Buchert |
| 5,433,197 A | | 7/1995 | Stark |
| 5,435,307 A | | 7/1995 | Friauf et al. |
| 5,441,476 A | * | 8/1995 | Kitado et al. ................... 600/26 |
| 5,503,770 A | | 4/1996 | James et al. |
| 5,636,635 A | | 6/1997 | Massie et al. |
| 5,664,578 A | | 9/1997 | Boczan ......................... 600/549 |
| 5,673,692 A | | 10/1997 | Schulze et al. |
| 5,711,915 A | | 1/1998 | Siegmund et al. |
| 5,813,982 A | | 9/1998 | Baratta |
| 5,817,008 A | | 10/1998 | Rafert et al. |
| 5,820,557 A | | 10/1998 | Hattori et al. |
| 5,830,139 A | | 11/1998 | Abreu |
| 5,854,078 A | | 12/1998 | Asher et al. |
| 5,898,004 A | | 4/1999 | Asher et al. |
| 6,011,984 A | | 1/2000 | Van Antwerp et al. |
| 6,040,194 A | | 3/2000 | Chick et al. |
| 6,047,203 A | * | 4/2000 | Sackner et al. ............... 600/388 |
| 6,072,180 A | | 6/2000 | Kramer et al. |
| 6,120,460 A | | 9/2000 | Abreu |
| 6,123,668 A | | 9/2000 | Abreu |
| 6,126,595 A | * | 10/2000 | Amano et al. ................. 600/300 |
| 6,135,968 A | | 10/2000 | Brounstein |
| 6,152,875 A | | 11/2000 | Hakamata |
| 6,178,346 B1 | | 1/2001 | Amundson et al. |
| 6,181,957 B1 | | 1/2001 | Lambert et al. |
| 6,187,599 B1 | | 2/2001 | Asher et al. |
| 6,197,534 B1 | | 3/2001 | Lakowicz et al. |
| 6,197,928 B1 | | 3/2001 | Tsien et al. |
| 6,213,943 B1 | | 4/2001 | Abreu |
| 6,256,522 B1 | | 7/2001 | Schultz |
| 6,290,658 B1 | * | 9/2001 | Kolich ......................... 600/595 |
| 6,292,685 B1 | * | 9/2001 | Pompei ........................ 600/474 |
| 6,312,393 B1 | | 11/2001 | Abreu |
| 6,319,540 B1 | | 11/2001 | Van Antwerp et al. |
| 6,423,001 B1 | | 7/2002 | Abreu |
| 6,470,893 B1 | | 10/2002 | Boesen ........................ 128/899 |
| 6,542,081 B2 | | 4/2003 | Torch ........................... 600/558 |
| 6,543,933 B2 | * | 4/2003 | Stergiopoulos et al. ...... 374/122 |
| 6,544,193 B2 | * | 4/2003 | Abreu ........................... 600/558 |
| 6,681,127 B2 | | 1/2004 | March |
| 6,731,976 B2 | * | 5/2004 | Penn et al. ................... 600/544 |
| 6,846,106 B1 | | 1/2005 | Chen et al. |
| 7,515,054 B2 | * | 4/2009 | Torch ........................ 340/573.1 |
| 7,689,437 B1 | * | 3/2010 | Teller et al. ...................... 705/2 |
| 2001/0028309 A1 | * | 10/2001 | Torch ........................... 340/575 |
| 2002/0035340 A1 | | 3/2002 | Fraden |
| 2002/0049389 A1 | * | 4/2002 | Abreu ........................... 600/558 |
| 2002/0068876 A1 | * | 6/2002 | Pompei et al. ................ 600/549 |
| 2002/0126731 A1 | * | 9/2002 | Stergiopoulos et al. ...... 374/122 |
| 2003/0179094 A1 | * | 9/2003 | Abreu ........................ 340/573.1 |
| 2009/0105605 A1 | * | 4/2009 | Abreu ........................... 600/549 |
| 2010/0113894 A1 | * | 5/2010 | Padiy ........................... 600/301 |
| 2011/0077546 A1 | * | 3/2011 | Fabian ......................... 600/544 |
| 2012/0136285 A1 | * | 5/2012 | Korb et al. ..................... 601/15 |
| 2013/0215928 A1 | * | 8/2013 | Bellifemine .................. 374/121 |

FOREIGN PATENT DOCUMENTS

| | | |
|---|---|---|
| EP | 236 028 | 9/1987 |
| WO | WO 93/01745 | 2/1993 |
| WO | WO 97/19188 | 5/1997 |
| WO | WO 98/22820 | 5/1998 |
| WO | WO 99/51142 | 10/1999 |
| WO | WO 00/10007 | 2/2000 |
| WO | WO 00/13580 | 3/2000 |
| WO | WO 00/16099 | 3/2000 |
| WO | WO 00/18237 | 4/2000 |
| WO | WO 00/64492 | 11/2000 |
| WO | WO 02/03855 | 1/2002 |
| WO | WO 02/067688 | 9/2002 |

OTHER PUBLICATIONS

Ophthal. Physiol. Opt., 1989, vol. 9, Apr. 1989 Research Note, Multiple Applications of the NCT: An Assessment of Instrument's Effect on IOP by G.E. Russell and J.P.G. Bergmanson, pp. 212-214.

Arch Ophthalmol—vol. 97, Mar. 1979, The Pneumatonograph—A Laboratory Study, by Robert A. Moses, M.D. and Walter J. Grodzki Jr., D.D.S., pp. 547-552.

IEEE Transactions on Bio-Medical Engineering, vol. BME-14, No. 2, Apr. 1967, Miniature Passive Pressure Transensor for Implanting in the Eye, by C.C. Collins, pp. 74-83.

Trans. Amer. Acad. of O. & O., Jan.-Feb. 1957, Tonometer Calibration, An Attempt to Remove Discrepancies Found in the 1954 Calibration Scale for Schiotz Tonometers by Jonas S. Friedenwald, M.D., pp. 108-123.

Investigative Ophthalmology, Feb. 1962, The Relationship Between Pressure and Volume Changes in Living and Dead Rabbi Eyes, by John E. eisenlohr and Maurice E. Langham, pp. 63-77.

Investigative Ophthalmology, Sep. 1971, vol. 10, No. 9, Theory and Calibration of the Schiotz Tonometer VII. Experimental Results of Tonometric Measurements: Scale Reading Versus Indentation Volume, by Robert A. Moses and Walter J. Grodzki, pp. 716-723.

The British Journal of Ophthalmology, Jun. 1920, Communications—Tonometry, by HJ. Schiotz, pp. 250-261y=.

American Journal of Ophthalmology, vol. 20, No. 10, Oct. 1937, Contribution to the Theory and Practice of Tonometry by Jonas S. Friedenwald, M.D., pp. 985-1024.

Ophthalmologica vol. 150, No. 5, (1965), Rheoloqy of the Human Sclera, Unifying Formulation of Ocular Rigidity, by W.K. McEwen and Roger St. Helen, pp. 322-346.

(56) References Cited

OTHER PUBLICATIONS

A.M.A. Archives of Ophthalmology. vol. 57, Apr. 1957, Tonometer Calibration, by Earle H. McBain, M.D., pp. 520-531.
The Photonics Dictionary, 1996 Book 4, $42^{nd}$ Edition, pp. D-24, D153.
Manual of Skin diseases, Fifth Edition, Gordon C. Sauer, MD., 1985, pp. 204, 373.
Fm-2 Fluorotron™ Master Ocular Fluorphotometer, 1994 OcuMetrics, Inc.
Textbook of Biochemistry With Clinical Correlations, Second Edition, Thomas M. Devlin, Ph.D., 1986, pp. 118,139.
Physical Optics, Third Revised Edition, Robert W. Wlld, 1961, pp. 650-651.
Ophthal. Physiol. Opt., 1989 vol. 9, Apr. 1989 Research Note, Multiple Applications of the NCT: An Assessment of Instrument's Effect on IOP by G.E. Russell and J.P.G. Bergmanson, pp. 212-214.
Investigative Ophthalmology, Sep. 1971, vol. 10, No. 9, Theory and Calibration of the Schiotz Tonometer VII. Exerimental Results of Tonometric Measurements: Scale Reading Versus Indentation Volume, by Robert A. Moses and Walter J. Grodzki, pp. 716-723.
Ophthalmologica vol. 150, No. 5, (1965), Rheology of the Human Sclera, Unifying Formulation of Ocular Rigidity, by W.K. McEwen and Roger St. Helen, pp. 322-346.
A.M.A. Archives of Ophthalmology, vol. 57, Apr. 1957, Tonometer Calibration, by Earle H. McBain, M.D., pp. 520-531.
Textbook of Biochemistry With Clinical Correlations, Second Edition, Thomas M. Devlin, Ph.D., 1986, pp. 118, 139.

\* cited by examiner

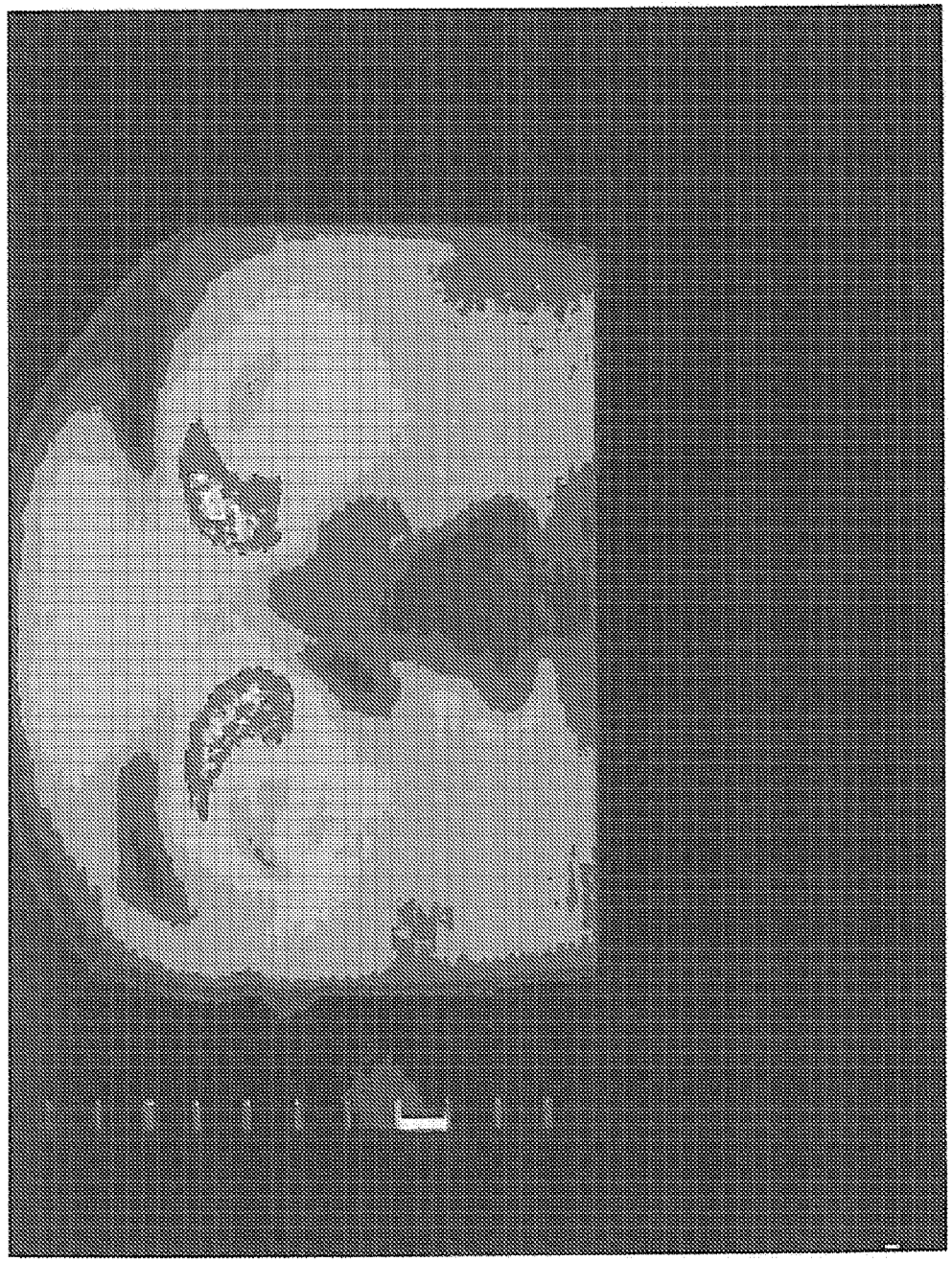

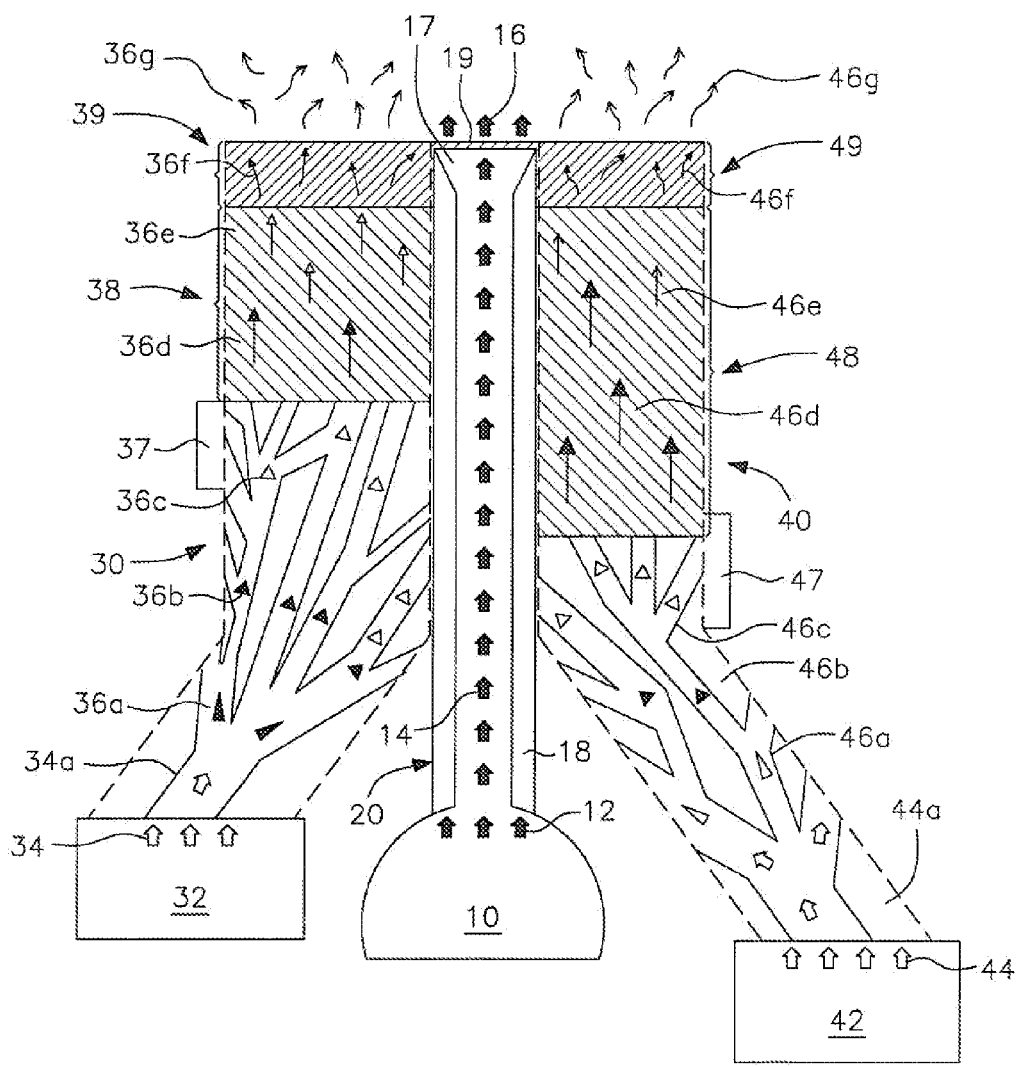

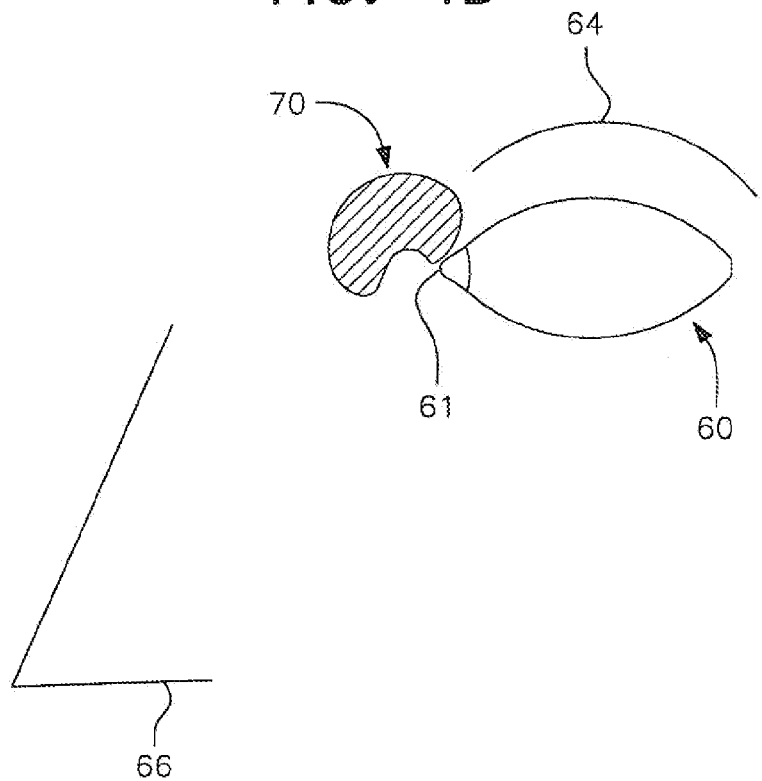
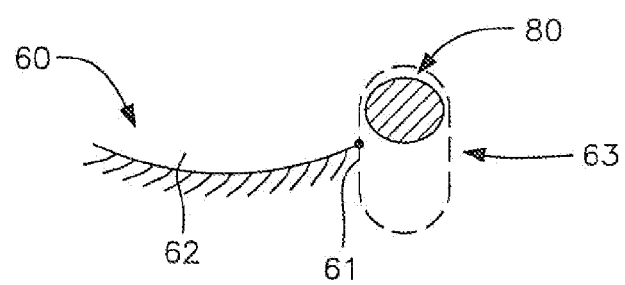

FIG. 6A
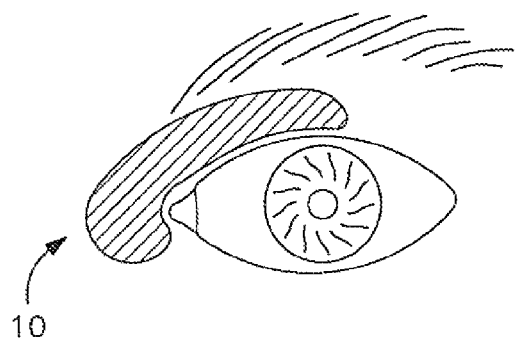
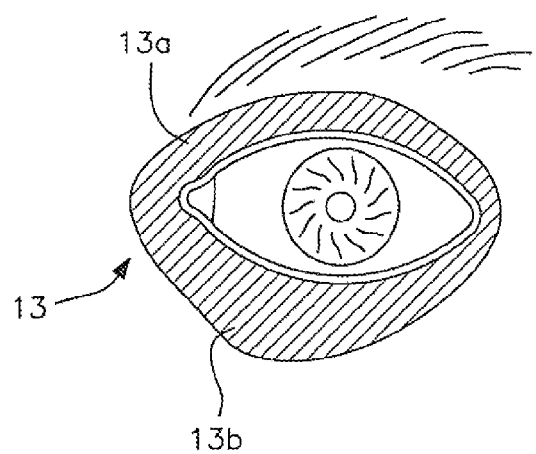

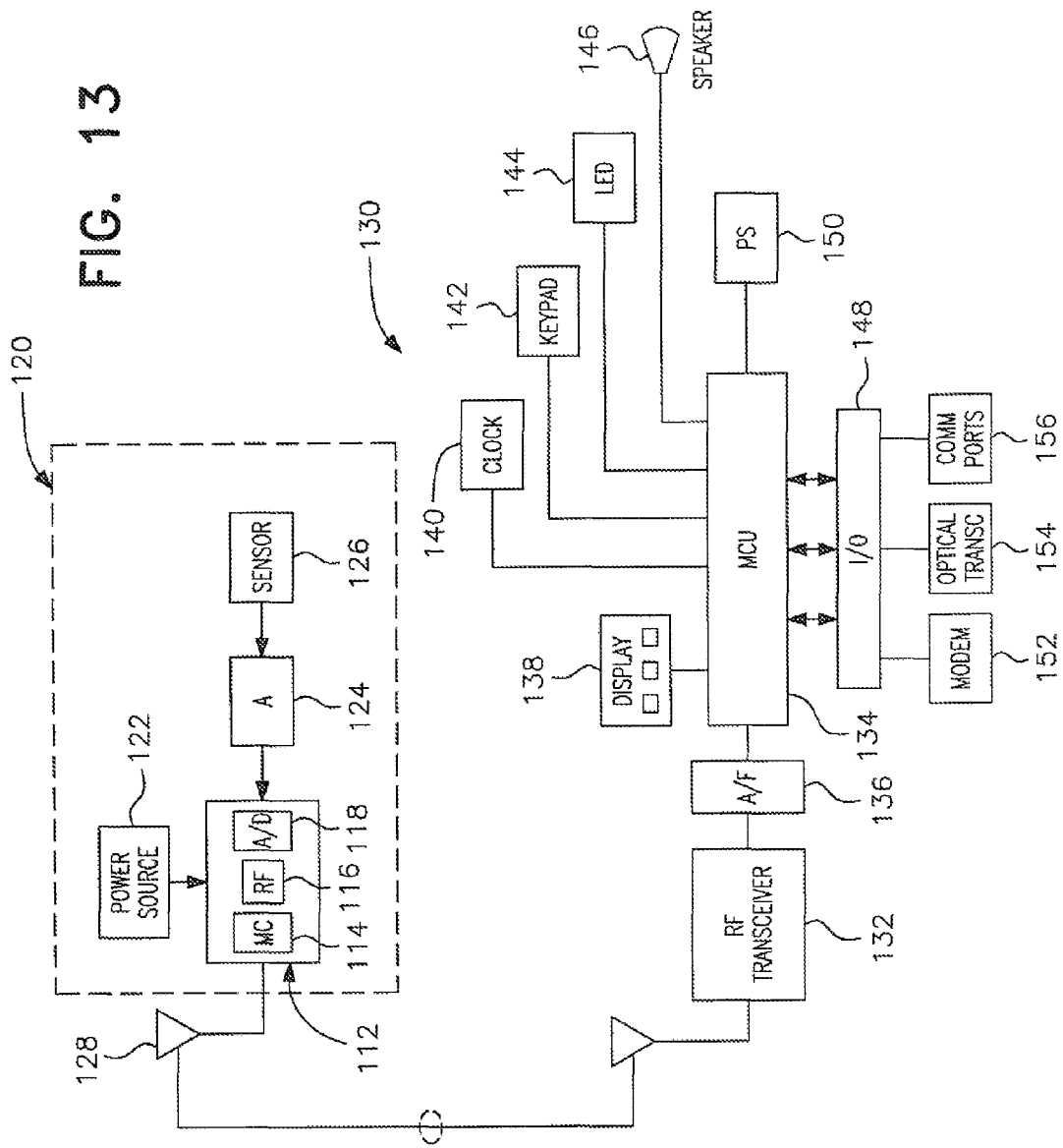

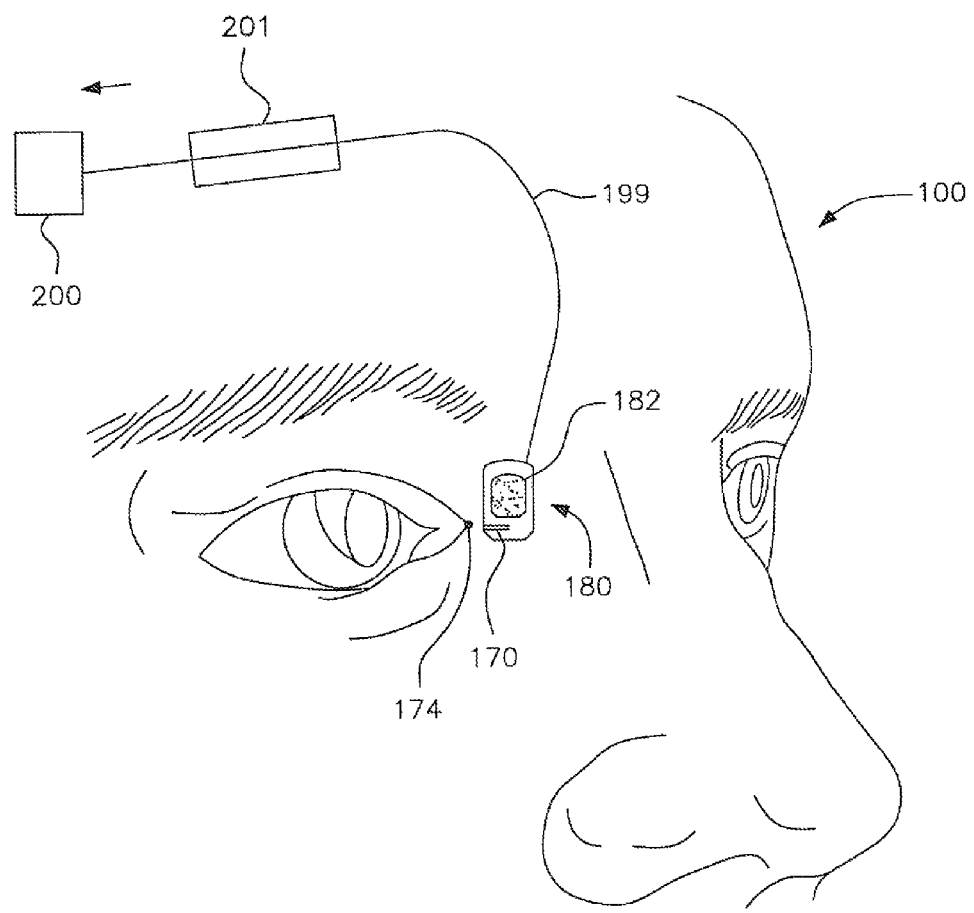

FIG. 19A1
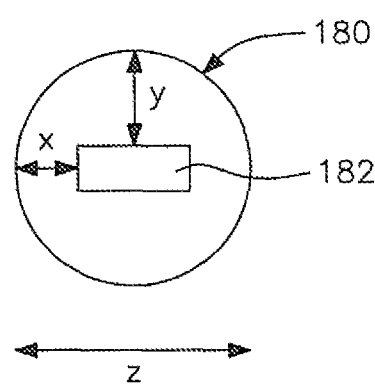
FIG. 19A2
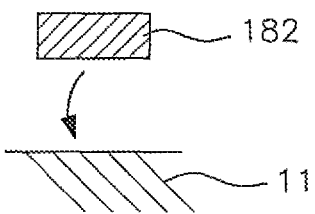
FIG. 19B
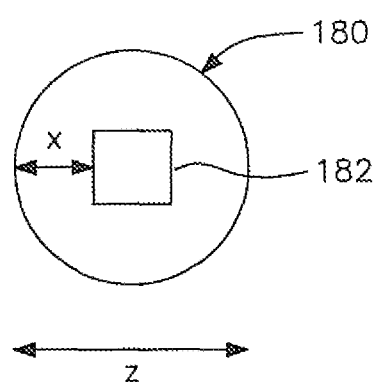
FIG. 19C
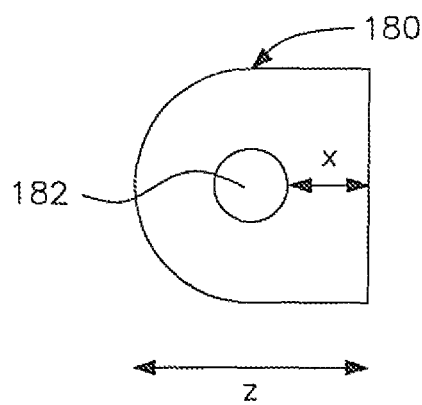
FIG. 19D
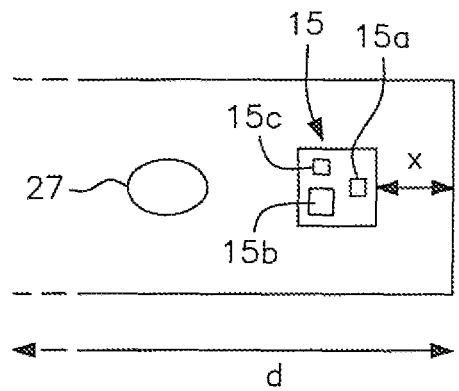

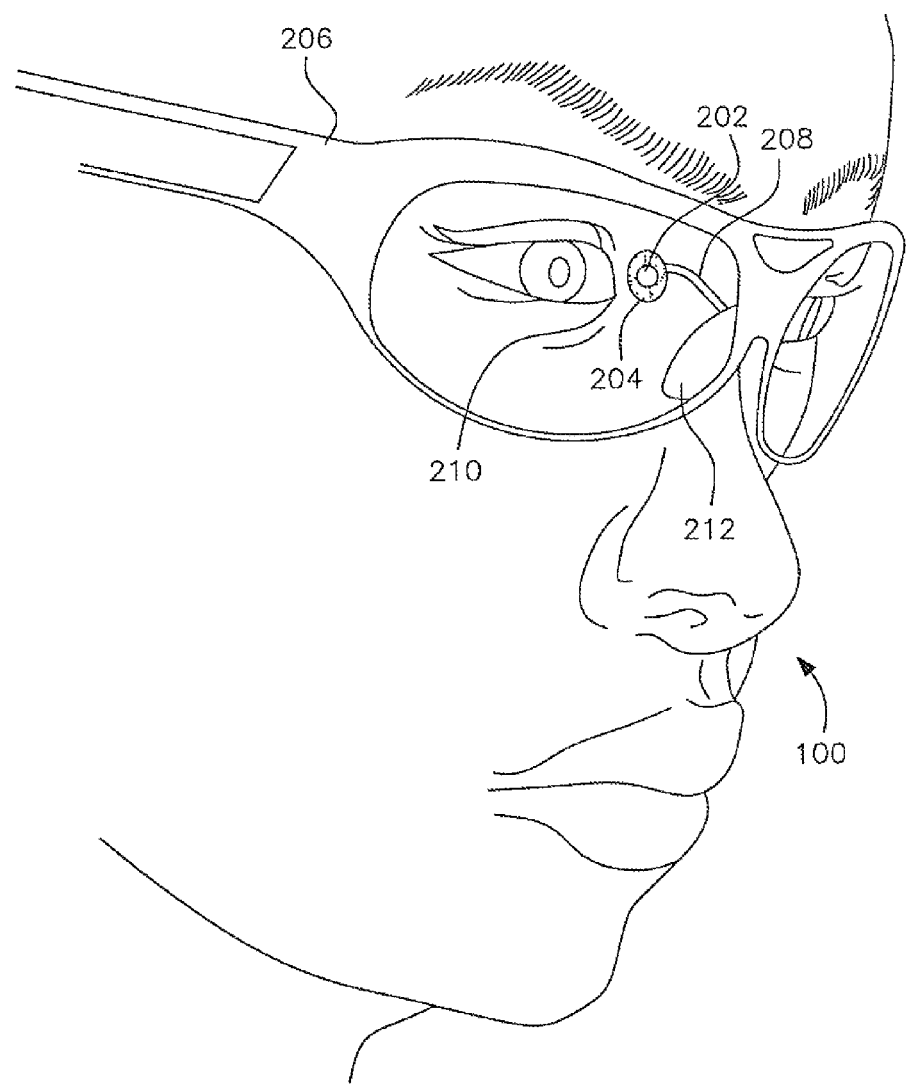

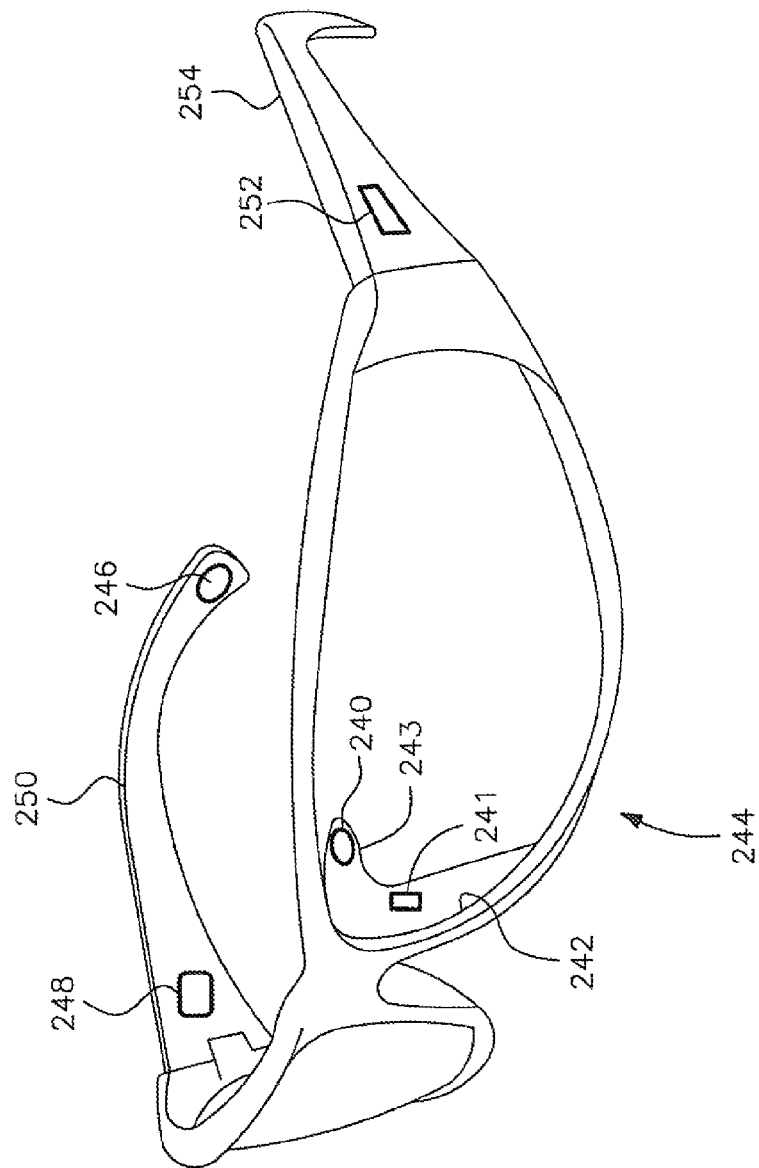

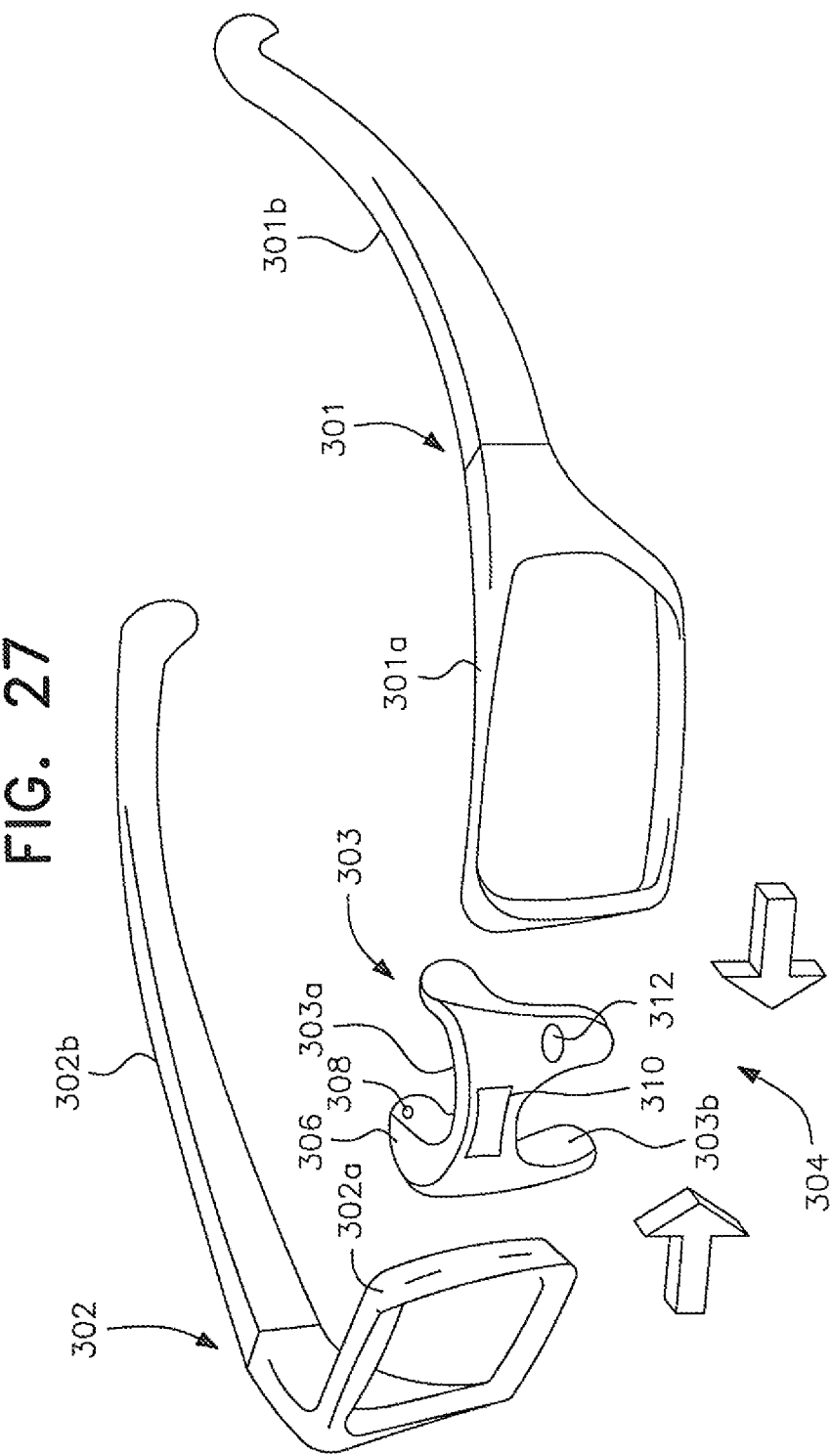

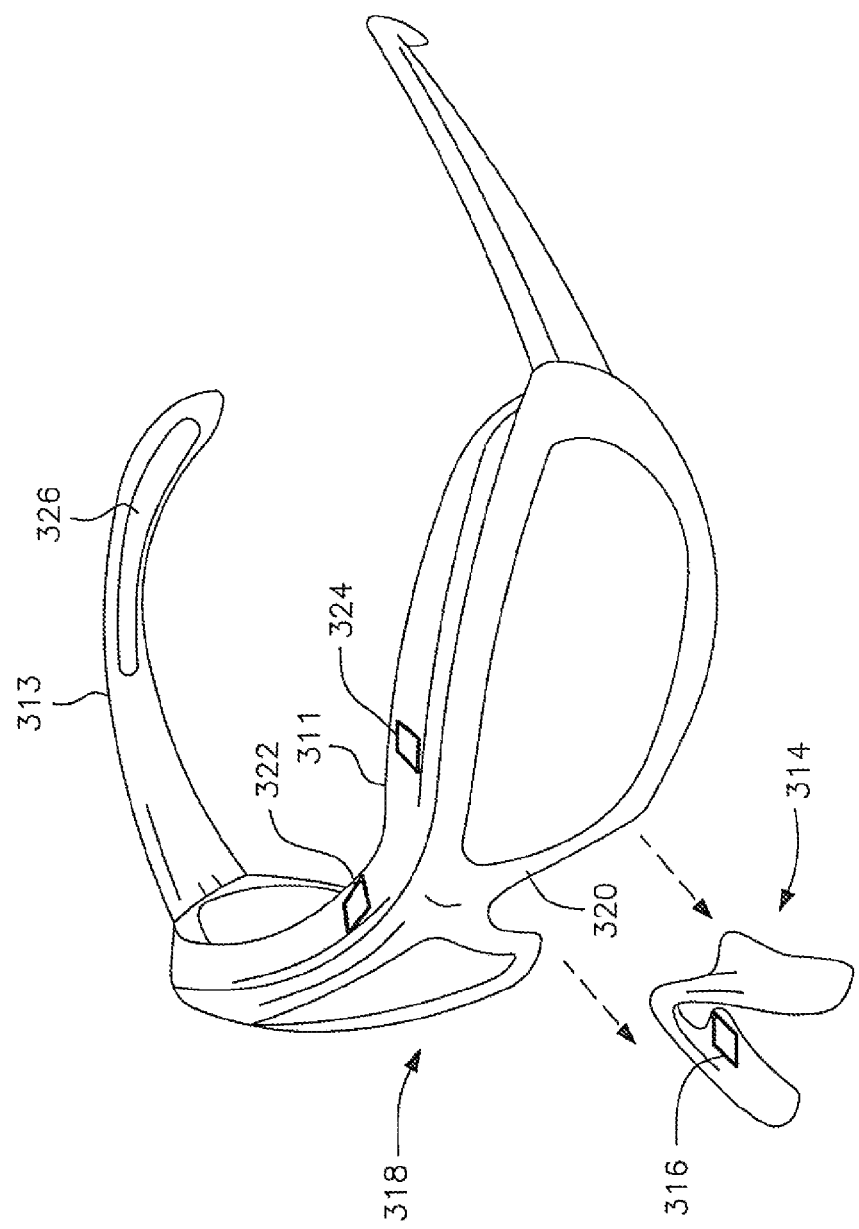

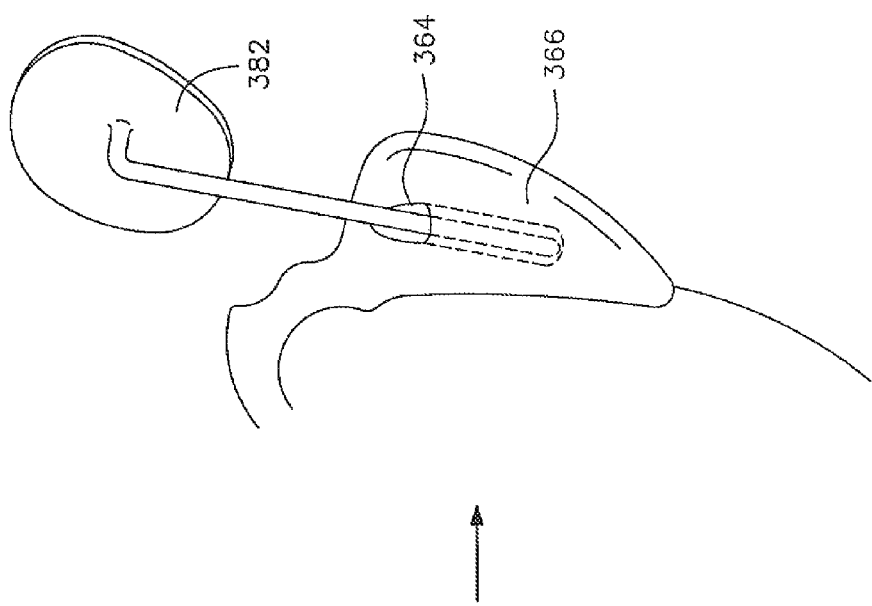
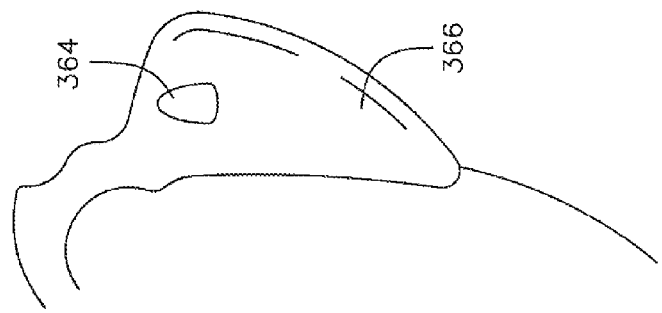

APPARATUS AND METHOD FOR MEASURING BIOLOGIC PARAMETERS

This is a divisional of application Serial No. filed Ser. No. 10/420,295, filed Apr. 22, 2003, now U.S. Pat. No. 7,187,960 which in turn is a complete application of provisional application Ser. No. 60/374,133, filed Apr. 22, 2002.

FIELD OF THE INVENTION

The present invention includes support and sensing structures positioned in a physiologic tunnel for measuring bodily functions and to manage abnormal conditions indicated by the measurements.

BACKGROUND OF THE INVENTION

Interfering constituents and variables can introduce significant source of errors that prevent measured biologic parameters from being of clinical value. In order to bypass said interfering constituents and achieve undisturbed signals invasive and semi-invasive techniques have been used. Such techniques have many drawbacks including difficulties in providing continuous monitoring for long periods of time. Non-invasive techniques also failed to deliver the clinical usefulness needed. The placement of a sensor on the skin characterized by the presence of interfering constituents do not allow obtaining clinically useful nor accurate signals due to the presence of said interfering constituents and background noise which greatly exceeds the signal related to the physiologic parameter being measured.

The most precise, accurate, and clinically useful way of evaluating thermal status of the body in humans and animals is by measuring brain temperature. Brain temperature measurement is the key and universal indicator of both disease and health equally, and is the only vital sign that cannot be artificially changed by emotional states. The other vital signs (heart rate, blood pressure, and respiratory rate) all can be influenced and artificially changed by emotional states or voluntary effort.

Body temperature is determined by the temperature of blood, which emits heat as far-infrared radiation. Adipose tissue (fat tissue) absorbs far-infrared and the body is virtually completely protected with a layer of adipose tissue adherent to the skin. Thus measurement of temperature using the skin does not achieve precision nor accuracy because previous techniques using sensors placed on skin included by the presence of adipose tissue.

Because it appeared to be impossible with current technology to non-invasively measure brain temperature, attempts were made to determine internal body temperature, also referred to as core temperature. An invasive, artificial, inconvenient, and costly process is currently used to measure internal (core) temperature consisting of inserting a catheter with a temperature sensor in the urinary canal, rectum or esophagus. But such methodology is not suitable for routine measurement, it is painful, and has potential fatal complications.

Semi-invasive techniques have also being tried. Abreu disclosed in U.S. Pat. No. 6,120,460 apparatus and methods for measuring core temperature continuously using a contact lens in the eyelid pocket, but the contact lens is a semi-invasive device which requires prescription by a physician and sometimes it is not easy to place the contact lens in the eye of an infant or even in adults and many people are afraid of touching their eyes.

There are several drawbacks and limitations in the prior art for continuous and/or core measurement of temperature.

Measurement of temperature today is non-continuous, non-core and nurse dependent. Nurses have to stick a thermometer in the patient's mouth, rectum or ear. To get core temperature nurses invasively place a tube inside the body which can cause infection and costly complications.

Measurement of core temperature on a routine basis in the hospital and/or continuously is very difficult and risky because it requires an invasive procedure with insertion of tubes inside the body or by ingesting a thermometer pill. The thermometer pill can cause diarrhea, measure temperature of the fluid/food ingested and not body temperature, and have fatal complications if the pill obstructs the pancreas or liver ducts. Placement of sensors on the skin do not provide clinically useful measurements because of the presence of many interfering constituents including fat tissue.

It is not possible to acquire precise and clinically useful measurements of not only brain temperature, but also metabolic parameters, physical parameters, chemical parameters, and the like by simply placing a sensor on the skin. One key element is the presence of fat tissue. Fat varies from person to person, fat varies with aging, fat content varies from time to time in the same person, fat attenuates a signal coming from a blood vessel, fat absorbs heat, fat prevents delivery of undisturbed far-infrared radiation, fat increases the distance traveled by the element being measured inside the body and an external sensor placed on the surface of the skin.

There is a need to identify a method and apparatus that can non-invasively, conveniently and continuously monitor brain temperature in a painless, simple, external and safe manner with sensors placed on the skin.

There is further a need to identify a method and apparatus that can conveniently, non-invasively, safely and precisely monitor biological parameters including metabolic parameters, physical parameters, chemical parameters, and the like.

There is a need to identify an apparatus and method capable of measuring biological parameters by positioning a sensor on a physiologic tunnel for the acquisition of undisturbed and continuous biological signals.

SUMMARY OF THE INVENTION

The present invention provides methods, apparatus and systems that effectively address the needs of the prior art.

In general, the invention provides a set of sensing systems and reporting means which may be used individually or in combination, which are designed to access a physiologic tunnel to measure biological, physical and chemical parameters. Anatomically and physiologically speaking, the tunnel discovered by the present invention is an anatomic path which conveys undisturbed physiologic signals to the exterior. The tunnel consists of a direct and undisturbed connection between the source of the function (signal) within the body and an external point at the end of the tunnel located on the skin. A physiologic tunnel conveys continuous and integral data on the physiology of the body. An undisturbed signal from within the body is delivered to an external point at the end of the tunnel. A sensor placed on the skin at the end of the tunnel allows optimal signal acquisition without interfering constituents and sources of error.

Included in the present invention are support structures for positioning a sensor on the skin at the end of the tunnel. The present invention discloses devices directed at measuring brain temperature, brain function, metabolic function, hydrodynamic function, hydration status, hemodynamic function, body chemistry and the like. The components include devices and methods for evaluating biological parameters using patches, clips, eyeglasses, head mounted gear and the like with sensing systems adapted to access physiologic tunnels to provide precise and clinically useful information about the physiologic status of the wearer and for enhancing the safety and performance of said wearer, and helping to enhance and preserve the life of said wearer by providing adequate reporting means and alert means relating to the biological parameter being monitored. Other components provide for producing direct or indirect actions, acting on another device, or adjusting another device or article of manufacture based on the biological parameter measured.

The search for a better way to measure biological parameters has resulted in long and careful research, which included the discovery of a Brain Temperature Tunnel (BTT) and other physiologic tunnels in humans and animals. The present invention was the first to recognize the physiologic tunnel in the body. The present invention was yet the first to recognize the end of the tunnel on the skin surface in which an optimal signal is acquired and measurements can be done without the presence of interfering constituents and background noise that exceeds the signal being measured. The present invention was also the first to recognize and precisely map the special geometry and location of the tunnel including the main entry point. The present invention was yet first to recognize the precise positioning of sensing systems at the main entry point for optimal signal acquisition. Careful studies have been undertaken including software development for characterizing infrared radiation to precisely determine the different aspects of the tunnel. This research has determined that the measurement of brain (core) temperature and other body parameters can be accomplished in a non-invasive and continuous manner in humans and animals with sensors positioned in a confined area of the skin at the end of a physiologic tunnel.

The key function and critical factor for life preservation and human performance is brain temperature. Brain tissue is the tissue in the body most susceptible to thermal damage, by both high and low temperature. Brain temperature is the most clinically relevant parameter to determine the thermal status of the body and the human brain is responsible for 18 to 20% of the heat produced in the body, which is an extraordinary fact considering that the brain represents only 2% of the body weight. The great amount of thermal energy generated in the brain is kept in a confined space and the scalp, skull, fat and CSF (cerebral spinal fluid) form an insulating layer. The recognition of the BTT by the present invention bypasses the insulating barriers and provides a direct connection to inside the brain physiology and physics.

Anatomically and physiologically speaking, a Brain Temperature Tunnel consists of a continuous, direct, and undisturbed connection between the heat source within the brain and an external point at the end of the tunnel. The physical and physiological events at one end of the tunnel inside the brain are reproduced at the opposite end on the skin. A BTT enables the integral and direct heat transfer through the tunnel without interference by heat absorbing elements, i.e., elements that can absorb far-infrared radiation transmitted as heat by blood within the brain. There are six characteristics needed to define a BTT. These characteristics are:

1) area without heat absorbing elements, i.e., the area must not contain adipose tissue (fat tissue). This is a key and needed characteristic for defining a temperature tunnel,
2) area must have a terminal branch of a vessel in order to deliver the integral amount of heat,
3) terminal branch has to be a direct branch of a blood vessel from the brain,
4) terminal branch has to be superficially located to avoid heat absorption by deep structures such as muscles,
5) area must have a thin and negligible interface between a sensor and the source of thermal energy to achieve high heat flow, and
6) area must not have thermoregulatory arteriovenous shunts.

All six characteristics are present on the skin on the medial canthal area adjacent to the medial corner of the eye above the medial canthal tendon and in the medial third of the upper eyelid. In more detail the end of BTT area on the skin measures about 11 mm in diameter measured from the medial corner of the eye at the medial canthal tendon and extend superiorly for about 6 mm and then extends into the upper eyelid in a horn like projection for another 22 mm.

The BTT area is the only area in the body without adipose tissue, which is in addition supplied by a terminal branch, which has a superficial blood vessel coming from the brain vasculature, and which has a thin interface and no thermoregulatory shunts. The BTT area is supplied by a terminal branch of the superior ophthalmic vein which is a direct connection to the cavernous sinus, said cavernous sinus being an endothelium-lined system of venous channels inside the brain which collects and stores thermal energy. The blood vessel supplying the BTT area is void of thermoregulatory arteriovenous shunts and it ends on the skin adjacent to the medial corner of the eye and in the superior aspect of the medial canthal area right at the beginning of the upper eyelid. The blood vessels deliver undisturbed heat to the skin on the medial canthal area and upper eyelid as can be seen in the color as well as black and white photos of infrared images shown in FIGS. 1 and 2. The undisturbed thermal radiation from the brain is delivered to the surface of the skin at the end of the tunnel. The heat is delivered to an area of skin without fat located at the end of the tunnel. The blood vessel delivering heat is located just below the skin and thus there is no absorption of infrared radiation by deep structures.

If the blood vessel is located deep, other tissues and chemical substances would absorb the heat, and that can invalidate the clinical usefulness of the measurement. There is direct heat transfer and the skin in the BTT area is the thinnest skin in the body and is void of thermoregulatory arteriovenous shunts. A very important aspect for optimal measurement of temperature is no interference by fat tissue and direct heat transfer.

The absence of fat tissue in this particular and unique area in the body at the end of the tunnel allows the undisturbed acquisition of the signal. The combination of those six elements allows the undisturbed and integral emission of infrared radiation from the brain in the form of direct heat transfer at the BTT area location, which can be seen in the infrared image photographs (FIGS. 1 to 8). The BTT and physiologic tunnels are also referred in this description as the "Target Area".

From a physical standpoint, the BTT is the equivalent of a Brain Thermal Energy tunnel with high total radiant power and high heat flow. The temperature of the brain is determined by the balance between thermal energy produced due to metabolic rate plus the thermal energy delivered by the arterial supply to the brain minus the heat that is removed by cerebral blood flow. Convection of heat between tissue and capillaries is high and the temperature of the cerebral venous blood is in equilibrium with cerebral tissue. Accordingly, parenchymal temperature and thermal energy of the brain can be evaluated by measuring the temperature and thermal energy of the cerebral venous blood. The superior ophthalmic vein has a direct and undisturbed connection to the cavernous sinus and carries cerebral venous blood with a thermal energy capacity of 3.6 $J \cdot ml^{-1} \cdot (°C.)^{-1}$ at hematocrit of 45%. Cerebral thermodynamic response, thermal energy, and brain temperature can be evaluated by placing a sensor to capture thermal energy conveyed by the cerebral venous blood at the end of the BTT.

The research concerning BTT and physiologic tunnels involved various activities and studies including: 1) In-vitro histologic analysis of mucosal and superficial body areas; 2) In-vivo studies with temperature evaluation of external areas in humans and animals; 3) In-vivo functional angiographic evaluation of heat source; 4) Morphologic studies of the histomorphometric features of the BTT area; 5) In-vivo evaluation of temperature in the BTT area using: thermocouples, thermistors, and far-infrared; 6) Comparison of the BTT area measurements with the internal eye anatomy and current standard most used (oral) for temperature measurement; 7) Cold and heat challenge to determine temperature stability of BTT; and 8) Infrared imaging and isotherm determination. Software for evaluating geometry of tunnel was also developed and used. Simultaneous measurement of a reference temperature and temperature in the BTT area were done using pre-equally calibrated thermistors. A specific circuit with multiple channels was designed for the experiments and data collection.

The measurement of temperature in the BTT area showed almost identical temperature signal between the BTT area and the internal conjunctival anatomy of the eye, which is a continuation of the central nervous system. Measurement of the temperature in the internal conjunctival anatomy of eye as used in the experiment was described by Abreu in U.S. Pat. Nos. 6,120,460 and 6,312,393. The averaged temperature levels for BTT and internal eye were within 0.1° C. (0.18° F.) with an average normothermia value equivalent of 37.1° C. (98.8° F.) for the BTT and 37° C. (98.6° F.) for the internal eye. Comparison with the standard most used, oral temperature, was also performed. The temperature voltage signal of the BTT area showed an average higher temperature level in the BTT area of an equivalent of 0.3° C. (0.5° F.) when compared to oral.

Subjects underwent cold challenge and heat challenge through exercising and heat room. The lowering and rising of temperature in the BTT area was proportional to the lowering and rising in the oral cavity. However, the rate of temperature change was faster in the BTT area than for oral by about 1.2 minutes, and temperature at the BTT site was 0.5° C. (0.9° F.) higher on few occasions. Subjects of different race, gender, and age were evaluated to determine the precise location of the BTT area across a different population and identify any anatomic variation. The location of the BTT was present at the same location in all subjects with no significant anatomic variation, which can be seen in a sample of infrared imaging of different subjects.

The tunnel is located in a crowded anatomic area and thus the positioning of the sensor requires special geometry for optimal alignment with the end of the tunnel. The clinical usefulness of the tunnel can only be achieved with the special positioning of the sensor in relation to anatomic landmarks and the support structure. The tunnel is located in a unique position with distinctive anatomic landmarks that help define the external geometry and location of the end of the tunnel. The main entry point of the tunnel, which is the preferred location for positioning the sensor, requires the sensor to be preferably placed in the outer edge of a support structure. The preferred embodiment for the measurement of biological parameters by accessing a physiologic tunnel includes sensors positioned in a particular geometric position on the support structure.

The support structure includes patches containing sensors. For the purpose of the description any structure containing an adhesive as means to secure said structure to the skin at the end of the tunnel is referred to as a patch including strips with adhesive surfaces such as a "BAND-AID" adhesive bandage. It is understood that a variety of attachment means can be used including adhesives, designs incorporating spring tension pressure attachment, and designs based on other attachment methods such as elastic, rubber, jelly-pads and the like.

The patches are adapted to position sensors at the end of the tunnel for optimal acquisition of the signal. The patch is preferably secured to the area by having an adhesive backing which lays against the skin, although a combination of adhesive and other means for creating a stable apposition of the sensor to the tunnel can be used such as fastening or pressure.

Support structures also include clips or structures that are positioned at the end of the tunnel with or without adhesive and which are secured to the area by pressure means. Any structure that uses pressure means to secure said structure to the skin at the end of the tunnel is referred as a clip.

Head-mounted structures are structures mounted on the head or neck for positioning sensors on the end of the tunnel and include head bands with accessories that are adjacent to the tunnel, visors, helmets, headphone, structures wrapping around the ear and the like. For the purpose of this description TempAlert is referred herein as a system that measures temperature in the BTT area and has means to report the measured value and that can incorporate alarm means that are activated when certain levels are reached. Support structures yet include any article that has sensing means in which said sensing means are positioned at the end of the tunnel.

Support structures further include medial canthal pieces of eyeglasses. A medial canthal piece is also referred to herein as a medial canthal pad and includes a pad or a piece which positions sensing means on the skin at the medial canthal area on top of a tunnel, with said medial canthal piece being permanently attached to or mounted to an eyeglass. Any sensing means incorporated in an eyeglass (fixed or removable) for accessing a tunnel are referred to herein as EyEXT including means for sensing physical and chemical parameters. Any article of manufacture that has visual function, or ocular protection, or face protection with a part in contact with the tunnel is referred herein as eyeglasses and includes conventional eyeglasses, prescription eyeglasses, reading glasses, sunglasses, goggles of any type, masks (including gas masks, surgical masks, cloth masks, diving masks, eye-mask for sleeping and the like) safety glasses, and the like.

For brain temperature evaluation the tunnel area consists of the medial canthal area and the superior aspect of the medial corner of the eye. For brain function evaluation the tunnel area consists of primarily the upper eyelid area. For metabolic function evaluation the tunnel area consists of an area adjacent to the medial corner of the eye and both the upper and lower eyelids.

The measurement of metabolic function, brain function, immunogenic function, physical parameters, physico-chemical parameters and the like includes a variety of support structures with sensors accessing the physiologic tunnels. The sensors are placed in apposition to the skin immediately adjacent to the medial corner of the eye preferably in the superior aspect of the medial canthal area. The sensor can also be positioned in the medial third of the upper eyelid. The sensor is most preferably located at the main entry point of the tunnel which is located on the skin 2.5 mm medial to the corner of the eye and about 3 mm above the medial corner of the eye. The diameter of the main entry point is about 6 to 7 mm. The positioning of the sensor at the main entry point of the tunnel provides the optimum site for measuring physical and chemical parameters of the body.

Besides a sensor that makes contact with the skin at the Target Area, it is understood that sensors which do not make contact with the skin can be equally used. For instance an infrared-based temperature measuring system can be used. The measurement is based on the Stefan-Boltzman law of physics in which the total radiation is proportional to the fourth power of the absolute temperature, and the Wien Displacement law in which the product of the peak wavelength and the temperature are constant. The field of view of the non-contact infrared apparatus of the invention is adapted to match the size and geometry of the BTT area on the skin.

A variety of lenses known in the art can be used for achieving the field of view needed for the application. For example, but not by way of limitation, a thermopile can be adapted and positioned in a manner to have a field of view aimed at the main entry point of the BTT area on the skin. The signal is then amplified, converted into a voltage output and digitized by a MCU (microcontroller).

This infrared-based system can be integrated into a support structure that is in contact with the body such as any of the support structures of the present invention. In addition, it is understood that the infrared-based system of the present invention can be integrated as a portable or hand-held unit completely disconnected from the body. The apparatus of the present invention can be held by an operator that aims said apparatus at the BTT area to perform the measurement. The apparatus further includes an extension shaped to be comfortably positioned at the BTT site for measuring biological parameters without discomfort to the subject. The extension in contact with the skin at the BTT is shaped in accordance with the anatomic landmarks and the geometry and size of the BTT site. The infrared radiation sensor is positioned in the extension in contact with the skin for receiving radiation emitted from the BTT site.

The present invention provides a method for measuring biological parameters including the steps of positioning sensing means on the skin area at the end of a tunnel, producing a signal corresponding to the biological parameter measured and reporting the value of the parameter measured.

It is also included a method to measure biological parameters by non-contact infrared thermometry comprising the steps of positioning an infrared detector at the BTT site with a field of view that encompasses the BTT site and producing a signal corresponding to the measured infrared radiation. The biological parameters include temperature, blood chemistry, metabolic function and the like.

Temperature and ability to do chemical analysis of blood components is proportional to blood perfusion. The present invention recognizes that the tunnel area, herein also referred as a Target Area, has the highest superficial blood perfusion in the head and has a direct communication with the brain, and that the blood vessels are direct branches of the cerebral vasculature and void of thermoregulatory arteriovenous shunts. It was also recognized that the Target Area has the highest temperature in the surface of the body as can be seen in the photographs of experiments measuring infrared emission from the body and the eye.

The Target Area discovered not only has the thinnest and most homogeneous skin in the whole body but is the only skin area without a fat layer. Since fat absorbs significant amounts of radiation, there is a significant reduction of signal. Furthermore other skin areas only provide imprecise and inaccurate signals because of the large variation of adipose tissue from person to person and also great variability of fat tissue according to age. This interference by a fat layer does not occur in the Target Area. Furthermore, the combined characteristics of the Target Area, contrary to the skin in the rest of the body, enable the acquisition of accurate signals and a good signal to noise ratio which far exceeds background noise. In addition, body temperature such as is found in the surface of the skin in other parts of the body is variable according to the environment.

Another important discovery of the present invention was the demonstration that the Target Area is not affected by changes in the environment (experiments included cold and heat challenge). The Target Area provides an optimum location for temperature measurement which has a stable temperature and which is resistant to ambient conditions. The Target Area discovered has a direct connection to the brain, is not affected by the environment and provides a natural, complete thermal seal and stable core temperature. The apparatus and methods of the present invention achieve precision and clinical usefulness needed with the non-invasive placement of a temperature sensor on the skin in direct contact with the heat source from the brain without the interference of heat absorbing elements.

The Target Area is extremely vascularized and is the only skin area in which a direct branch of the cerebral vasculature is superficially located and covered by a thin skin without a fat layer. The main trunk of the terminal branch of the ophthalmic vein is located right at the BTT area and just above the medial canthal tendon supplied by the medial palpebral artery and medial orbital vein. The BTT area on the skin supplied by a terminal and superficial blood vessel ending in a particular area without fat and void of thermoregulatory arteriovenous shunts provides a superficial source of undisturbed biological signals including brain temperature, metabolic function, physical signals, and body chemistry such as glucose level, and the like.

Infrared spectroscopy is a technique based on the absorption of infrared radiation by substances with the identification of said substances according to its unique molecular oscillatory pattern depicted as specific resonance absorption peaks in the infrared region of the electromagnetic spectrum. Each chemical substance absorbs infrared radiation in a unique manner and has its own unique absorption spectra depending on its atomic and molecular arrangement and vibrational and rotational oscillatory pattern. This unique absorption spectra allows each chemical substance to basically have its own infrared spectrum, also referred to as fingerprint or signature which can be used to identify each of such substances. Radiation containing various infrared wavelengths is emitted at the substance to be measured and the amount of absorption of radiation is dependent upon the concentration of said chemical substance being measured according to Beer-Lambert's Law.

Interfering constituents and variables such as fat, bone, muscle, ligaments and cartilage introduce significant source of errors which are particularly critical since the background noise greatly exceeds the signal of the substance of interest. Since those interfering constituents area not present on the skin at the BTT area, the sensing systems positioned at said BTT are can acquire optimal signal with minimal noise including spectroscopic-based measurements.

Spectroscopic means integrated into support structures disclosed in the present invention can precisely non-invasively measure blood components since the main sources of variation and error, such as fat tissue, are not present in the Target Area. In addition, other key constituents which interfere with electromagnetic energy emission such as muscle, cartilage and bones, are not present in the Target Area either. The blood vessels delivering the infrared radiation are superficially located and the infrared radiation is delivered at the end of the tunnel without interacting with other structures. The only structure to be traversed by the infrared radiation is a very thin skin, which does not absorb the infrared wavelength. The present invention includes infrared spectroscopy means to provide a clinically useful measurement with the precise and accurate determination of the concentration of the blood components at the end of the tunnel.

In addition to spectroscopy in which electromagnetic energy is delivered to the Target Area, the present invention also discloses apparatus and methods for measuring substances of interest through far infrared thermal emission from the Target Area. Yet, besides near-infrared spectroscopy and thermal emission, other means are disclosed for measurement of substances of interest at the Target Area including electroosmosis as a flux enhancement by iontophoresis or reverse iontophoresis with increased passage of fluid through the skin through application of electrical energy. Yet, transcutaneous optical means can also be integrated into support structures including medial canthal pieces, modified nose pads, and the frame of eyeglasses, with said means positioned to access the tunnel.

It is understood that application of current, ultrasonic waves as well as chemical enhancers of flow, electroporation and other means can be used to increase permeation at the tunnel site such as for example increased flow of glucose with the use of alkali salts. In addition creating micro holes in the target area with a laser, or other means that penetrate the skin can be done with the subsequent placement of sensing means on the BTT site, with said means capable of measuring chemical compounds. Furthermore, reservoirs mounted on or disposed within support structures, such as the frame and pads of eyeglasses, can deliver substances transdermally at the BTT site by various means including iontophoresis, sonophoresis, electrocompression, electroporation, chemical or physical permeation enhancers, hydrostatic pressure and the like.

In addition to measure the actual amount of oxygen in blood, the present invention also discloses means to measure oxygen saturation and the amount of oxygenated hemoglobin. In this embodiment the medial canthal piece of a support structure or the modified nose pads of eyeglasses contain LEDs emitting at two wave lengths around 940 and 660 nanometers. As the blood oxygenation changes, the ratio of the light transmitted by the two frequencies changes indicating the oxygen saturation. Since the blood level is measured at the end of a physiologic brain tunnel, the amount of oxygenated hemoglobin in the arterial blood of the brain is measured, which is the most valuable and key parameter for athletic purposes and health monitoring.

The present invention also provides a method for measuring biological parameters with said method including the steps of directing electromagnetic radiation at the BTT area on the skin, producing a signal corresponding to the resulting radiation and converting the signal into a value of the biological parameter measured.

Besides using passive radio transmission or communication by cable; active radio transmission with active transmitters containing a microminiature battery mounted in the support structure can also be used. Passive transmitters act from energy supplied to it from an external source. The transensor transmits signals to remote locations using different frequencies indicative of the levels of biological parameters. Ultrasonic micro-circuits can also be mounted in the support structure and modulated by sensors which are capable of detecting chemical and physical changes at the Target Area. The signal may be transmitted using modulated sound signals particularly under water because sound is less attenuated by water than are radio waves.

One preferred embodiment comprises a support structure including a patch adapted to be worn on or attached with adhesives to the tunnel and includes structural support, a sensor for measuring biological parameters, power source, microcontroller and transmitter. The parts can be incorporated into one system or work as individual units. The sensor is located preferably within 7 mm from the outer edge of the patch. The apparatus of the invention can include a temperature sensor located in the outer edge of the patch for sensing temperature. The transmitter, power source and other components can be of any size and can be placed in any part of the patch or can be connected to the patch as long as the sensing part is placed on the edge of the patch in accordance with the principles of the invention. The sensor in the patch is positioned on the skin adjacent to the medial canthal area (medial corner of the eye) and located about 2 mm from the medial canthal tendon. The sensor can preferably include electrically-based sensors, but non-electrical systems can be used such as chemicals that respond to changes in temperature including mylar.

Besides patches, another preferred embodiment for measuring biological parameters at the physiologic tunnel includes a medial canthal pad. The medial canthal piece is a specialized structure containing sensors for accessing the tunnel and adapted to be worn on or attached to eyeglasses in apposition to the tunnel and includes structural support, a sensor for measuring biological parameters, power source, microcontroller and transmitter. The parts can be incorporated into one system or work as individual units. The sensors are positioned on the BTT area. The transmitter, power source, and other components can be placed in the medial canthal pad or in any part of the eyeglasses. A medial canthal piece or extension of nose pads of eyeglasses allow accessing the physiologic tunnel with sensing devices laying in apposition to the BTT area.

The apparatus of the invention include a temperature sensor located in the medial canthal pad. For temperature measurement the sensing system is located on a skin area that includes the medial canthal corner of the eye and upper eyelid. The sensor in the medial canthal pad is preferably positioned on the skin adjacent to the medial canthal area (medial corner of the eye). Although one of the preferred embodiments for measurement of brain temperature consists of medial canthal pads, it is understood that also included in the scope of the invention are nose pads of a geometry and size that reach the tunnel and that are equipped with temperature sensors preferably in the outer edge of said nose pads for measuring brain temperature and other functions. An oversized and modified nose pad containing sensors using a special geometry for adequate positioning at the BTT area is also included in the invention.

With the disclosure of the present invention and by using anatomic landmarks in accordance with the invention the sensor can be precisely positioned on the skin at the end of the tunnel. However, since there is no external visible indication on the skin relating to the size or geometry of the tunnel, accessory means can be used to visualize, map or measure the end of the tunnel on the skin. These accessory means may be particularly useful for fitting medial canthal pads or modified nose pads of eyeglasses.

Accordingly, a infrared detector using thermocouple or thermopiles can be used as an accessory for identifying the point of maximum thermal emission and to map the area. An infrared imaging system or thermography means may be preferably used. In this instance, an optical store selling the eyeglasses can have a thermal imaging system. The optician, technician and the like take an infrared image picture or film the area, and in real time localize the tunnel of the particular user. The medial canthal pads or modified nose pads can then be adjusted to fit the particular user based on the thermal infrared imaging. The eyeglasses are fitted based on the thermal image created. This will allow customized fitting according to the individual needs of the user. Any thermography-based system can be used including some with great visual impact and resolution as a tri-dimensional color thermal wave imaging.

It is also a feature of the invention to provide a method to be used for example in optical stores for locating the tunnel including the steps of measuring thermal infrared emission, producing an image based on the infrared emission, and detecting the area with the highest amount of infrared emission. Another step that can be included is adjusting sensors in support structures to match the area of highest infrared emission.

One of said support structures includes the medial canthal pieces or nose pads of eyeglasses. The thermal imaging method can be used for fitting a patch, but said patch can be positioned at the tunnel by having an external indicator for lining up said indicator with a permanent anatomic landmark such as the medial corner of the eye. Although medial canthal pieces of eyeglasses can have an external indicator for precise positioning, since opticians are used to fit eyeglasses according to the anatomy of the user, the thermal imaging method can be a better fit for eyeglasses than an external indicator on the medial canthal pieces or modified nose pads of eyeglasses.

The source of the signal is key for the clinical usefulness of the measurement. The brain is the key and universal indicator of the health status of the body. The signal coming from the brain or brain area provides the most clinically useful data. In accordance with another embodiment, the measurement of biological parameters will be described. The amount of sodium and other elements in sweat is a key factor for safety and performance of athletes and military, as well as health monitoring.

For instance hyponatremia (decreased amount of sodium) can lead to reduced performance and even death. Hyponatremia can occur due to excess water intake, commonly occurring with intense physical activity and military training. Sweat can be considered as an ultrafiltrate of blood. The blood vessels supplying the skin on the head are branches of the central nervous system vasculature. The amount of chemical substances present in the sweat coming from those blood vessels is indicative of the amount of chemical substances present in the cerebral vasculature. For instance, sodium concentration of sweat from blood vessels in the head changes in relation to the rates of sweating. The apparatus and methods of the present invention can prevent death or harm due to water intoxication, by providing alert signals when the levels of sodium in sweat reach a certain threshold for that particular wearer. The presence of various chemical elements, gases, electrolytes and pH of sweat and the surface of the skin can be determined by the use of suitable electrodes and suitable sensors integrated in the eyeglasses and other support structures mounted on the head or fitted on the head or face. These electrodes, preferably microelectrodes, can be sensitized by several reacting chemicals which are in the sweat or the surface of the skin. The different chemicals and substances can diffuse through suitable permeable membranes sensitizing suitable sensors.

For example but not by way of limitation, electrochemical sensors can be used to measure various analytes such as glucose using a glucose oxidase sensor and the pilocarpine iontophoresis method can be used to measure electrolytes in sweat alone or in conjunction with microfluidics system. Besides the support structures of the present invention, it is also understood that other articles such as watches, clothing, footwear and the like can be adapted to measure concentration of substances such as electrolytes present in sweat, however there is reduced clinical relevance for evaluating metabolic state of an individual outside the central nervous system.

Body abnormalities may cause a change in the pH, osmolarity, and temperature of the sweat derived from brain and neck blood vessels as well as change in the concentration of substances such as acid-lactic, glucose, lipids, hormones, gases, markers, infectious agents, antigens, antibody, enzymes, electrolytes such as sodium, potassium and chloride, and the like. Eyeglasses and any head gear can be adapted to measure the concentration of substances in sweat. Microminiature glass electrodes mounted in the end portion of the temple of eyeglasses sitting behind the ear or alternatively mounted on the lens rim against the forehead can be used to detect divalent cations such as calcium, as well as sodium and potassium ion and pH. Chloride-ion detectors can be used to detect the salt concentration in the sweat and the surface of the skin.

Many agents including biological warfare agents and HIV virus are present in sweat and could be detected with the eyeglasses or support structure on the head or face using sensors coated with antibodies against the agent which can create a photochemical reaction with appearance of calorimetric reaction and/or potential shift with subsequent change in voltage or temperature that can be detected and transmitted to a monitoring station or reported locally by audio or visual means. Electrocatalytic antibodies also can generate an electrical signal when there is an antigen-antibody interaction. It is also understood that other articles such as watches, clothing, footwear, and the like or any article capturing sweat can be adapted to identify antigens, antibody, infectious agents, markers (cancer, heart, genetic, metabolic, drugs, and the like) in accordance with the present invention. However, identification of those elements away from the central nervous system is of reduced clinical relevance.

The different amounts of fluid encountered in sweat can be easily quantified and the concentration of substances calibrated according to the amount of fluid in sweat. The relationship between the concentration of chemical substances and molecules in the blood and the amount of said chemical substances in the sweat can be described mathematically and programmed in a computer.

The present invention also includes eyeglasses or support structures in which a radio frequency transensor capable of measuring the negative resistance of nerve fibers is mounted in the eyeglasses or support structure. By measuring the electrical resistance, the effects of microorganisms, drugs, and poisons can be detected. The system also comprises eyeglasses in which a microminiature radiation-sensitive transensor is mounted in said eyeglasses or support structure.

The brain has a rich vasculature and receives about 15% of the resting cardiac output and due to the absence of fat the tunnel offers an area for optimal signal acquisition for evaluating hemodynamics. Accordingly, change in the viscosity of blood can be evaluated from a change in damping on a vibrating quartz micro-crystal mounted in the eyeglasses or support structure and the invention can be adapted to measure blood pressure and to provide instantaneous and continuous monitoring of blood pressure through an intact wall of a blood vessel from the brain and to evaluate hemodynamics and hydrodynamics. Also, by providing a contact microphone, arterial pressure can be measured using sonic means.

Pressure can be applied to a blood vessel through a micro cuff mounted in the medial canthal pads, or alternatively by the temples of eyeglasses. Pressure can also be applied by a rigid structure, and the preferred end point is reached when sound related to blood turbulence is generated. The characteristic sound of systole (contraction of the heart) and diastole (relaxation of the heart) can be captured by the microphone. A microphone integrated into the medial canthal pad can be adapted to identify the heart sounds. Pressure transducers such as a capacitive pressure transducer with integral electronics for signal processing and a microphone can be incorporated in the same silicon structure and can be mounted in the medial canthal pad. Motion sensors and/or pressure sensors can be mounted in the medial canthal pad to measure pulse.

Reversible mechanical expansion methods, photometric, or electrochemical methods and electrodes can be mounted in the eyeglasses or support structures of the present invention and used to detect acidity, gases, analyte concentration, and the like. Oxygen gas can also be evaluated according to its magnetic properties or be analyzed by micro-polarographic sensors mounted in the eyeglasses or other support structure. A microminiature microphone mounted in the eyeglasses or other support structure can also be adapted to detect sounds from the heart, respiration, flow, vocal and the environment, which can be sensed and transmitted to a remote receiver or reported by local audio and visual means. The sensors are adapted and positioned to monitor the biological parameters at the end of the tunnel.

The eyeglasses or other support structures can also have elements which produce and radiate recognizable signals and this procedure could be used to locate and track individuals, particularly in military operations. A permanent magnet can also be mounted in the eyeglasses and used for tracking as described above. A fixed frequency transmitter can be mounted in the eyeglasses and used as a tracking device which utilizes a satellite tracking system by noting the frequency received from the fixed frequency transmitter to a passing satellite, or via Global Positioning Systems. Motion and deceleration can be detected by mounting an accelerometer in the eyeglasses. The use of eyeglasses as tracking means can be useful for locating a kidnapped individual or for rescue operations in the military, since eyeglasses are normally unsuspecting articles.

The use of integrated circuits and advances occurring in transducer, power source, and signal processing technology allow for extreme miniaturization of the components which permits several sensors to be mounted in one unit.

The present invention provides continuous automated brain temperature monitoring without the need for a nurse. The present invention can identify a spike in temperature. Thus, proper diagnosis is made and therapy started in a timely fashion. Time is critical for identifying the temperature spike and organism causing the infection. Delay in identifying spike and starting therapy for the infection can lead to demise of the patient. The invention timely and automatically identifies the temperature spike and prevents the occurrence of complications.

The present invention also alerts the user about overheating or hypothermia to allow:
1. Proper hydration;
2. Increased performance;
3. Increased safety; and
4. Feed back control in treadmills and other exercise machines for keeping proper hydration and performance.

Annually many athletes, construction workers, college students and the general public unnecessarily die due to heatstrokes. Once the brain reaches a certain temperature level such as 40° C., an almost irreversible process ensues. Because there are no specific symptoms and after a certain point there is rapid increase in brain temperature, heatstroke has one of the highest fatality rates. The more severe and more prolonged the episode, the worse the predicted outcome, especially when cooling is delayed. Without measuring core temperature and having an alert system when the temperature falls outside safe levels it is impossible to prevent hyperthermia and heatstroke. The present invention provides means for continuous monitoring of temperature with alert systems that can prevent dangerous levels to be reached and cooling measures applied if needed. The apparatus can be adapted to be used in an unobtrusive manner by athletes, military, workers and the general population.

All chemical reactions in the body are dependent on temperature. High temperature can lead to enzymatic changes and protein denaturation and low temperature can slow down vital chemical reactions. Hydration is dependent on brain temperature and loss of fluid leads to a rise in brain temperature. Minimal fluctuations in the body's temperature can adversely affect performance and increase risk of illness and of life threatening events. Therefore, it is essential that athletes, sports participants, military personnel, police officers, firefighters, forest rangers, factory workers, farmers, construction workers and other professionals have precise means to know exactly what is their brain temperature.

When the core temperature rises, the blood that would otherwise be available for the muscles is used for cooling via respiration and perspiration. The body will do this automatically as temperature moves out of the preferred narrow range. It is this blood shifting that ultimately impairs physical performance and thermal induced damage to brain tissue interferes with normal cognitive function. Intense exercise can increase heat production in muscles 20 fold. In order to prevent hyperthermia and death by heat stroke athletes drink water. Because the ingestion of water is done in a random fashion, many times there is water intoxication which can lead to death as occurs to many healthy people including marathon runners and military personnel. Both, excess of water (overhydration) or lack of water (dehydration) can lead to fatal events besides reducing performance. Therefore, it is essential that individuals have precise means to know exactly when and how much to drink. By monitoring brain temperature with the present invention proper hydration can be achieved and athletes and military will know precisely when and how much water to ingest.

Timely ingestion of fluids according to the core temperature allows optimization of cardiovascular function and avoidance of heat strain. Because there is a delay from the time of ingestion of fluid to absorption of said fluid by the body, the method of invention includes signaling the need for ingestion at a lower core temperature such as 38.5° C. to account for that delay, and thus avoid the onset of exhaustion. The temperature threshold can be adjusted according to each individual, the physical activity, and the ambient temperature.

In addition, software can be produced based on data acquired at the BTT site for optimizing fitness, athletic performance, and safety. The upper temperature limit of a particular athlete for maintaining optimal performance can be identified, and the data used to create software to guide said athlete during a competition. For instance, the athlete can be informed on the need to drink cold fluid to prevent reaching a certain temperature level which was identified as reduced performance for said athlete. Brain temperature level for optimal performance identified can be used to guide the effort of an athlete during competition and training. Hyperthermia also affects mental performance and software based on data from the BTT can be produced to optimize mental and physical performance of firefighters in an individual manner. People can have different thresholds for deleterious effects of hyperthermia and thus setting one level for all users may lead to underutilization of one's capabilities and putting others at risk of reduced performance. Likewise, exercise endurance and mental performance is markedly reduced by hypothermia and the same settings can be applied for low temperature situations. Determinations of brain temperature, oxygen and lactic acid levels can also be used for endurance training of athletes, fitness training, and to monitor the effects of training. The system, method, and apparatus of the invention provides means for enhancing safety and optimizing fitness for athletes and recreational sports participants.

It is a feature of the invention to provide a method for the precise and timely intake of fluids including the steps of measuring brain temperature, reporting the signal measured, and ingesting an amount of fluid based on the signal measured. Other steps can be included such as reporting means using voice reproduction or visual means to instruct on what beverage to drink and how much to drink to reduce core temperature. It is understood that the method of the present invention can combine measurement of temperature associated with measurement of sodium in sweat or blood, in accordance with the principles of the invention.

Children do not tolerate heat as well as adults because their bodies generate more heat relative to their size than adults do. Children are also not as quick to adjust to changes in temperatures. In addition, children have more skin surface relative to their body size which means they lose more water through evaporation from the skin. It is understood that different sizes, shapes, and designs of medial canthal pads including children size can be used in the present invention. Children eyeglasses equipped with sensors can have a booster radio transmitter that will transmit the signal to a remote receiver and alert parents about dangerous temperature levels. The eyeglasses can be incorporated with a detecting system to send a signal if the eyeglasses were removed or if the temperature sensor is not capturing signals in a proper manner. By way of illustration, but not of limitation, pressure sensing means can be incorporated in the end of the temples to detect if the sunglasses are being worn, and an abrupt drop in the pressure signal indicates glasses were removed or misplacement of the sensor can also generate an identifiable signal. An adhesive, a double-sided adhesive tape, or other means for increasing grip can be used in the medial canthal pads to assure more stable position. It is understood that the eyeglasses can come equipped with sensors to detect ambient temperature and humidity, which allows for precisely alerting the wearer about any aspect affecting heat conditions.

In the current industrial, nuclear and military settings, personnel may be required to wear protective clothing. Although the protective clothing prevent harm by hazardous agents, the garments increase the rate of heat storage. It is understood that the present invention can be coupled with garments with adjustable permeability to automatically keep the core temperature within safe limits.

In addition, the present invention alerts an individual about risk of thermal damage (risk of wrinkles and cancer) at the beach or during outdoor activities. When one is at the beach, watching a game in a stadium, camping or being exposed to the sun, the radiant energy of the sun is absorbed and transformed into thermal energy. The combination of the different means of heat transfer to the body lead to an increase in body temperature, which is reflected by the brain temperature. Convection and conduction can also lead to an increase in body temperature through heat transfer in the absence of sun light. The absorption of heat from the environment leads to a rise in the average kinetic energy of the molecules with subsequent increase in core temperature.

The levels of core temperature is related to the risk of thermal damage to the skin. After certain levels of heat there is an increased risk of denaturing protein and breaking of collagen in the skin. This can be compared with changes that occur when frying an egg. After a certain amount of thermal radiation is delivered the egg white changes from fluidic and transparent to a hard and white structure. After the egg white reaches a certain level of temperature the structural change becomes permanent. After a certain level of increase in core temperature during sun exposure, such as a level of 37.7° Celsius to 37.9° Celsius at rest (e.g.; sun bathing), thermal damage may ensue and due to the disruption of proteins and collagen there is an increased risk for wrinkle formation. The increased brain temperature correlates to the amount of thermal radiation absorbed by the body, and the duration of exposure of the temperature level times the level of temperature is an indicator of the risk of thermal damage, wrinkle formation, and skin cancer.

The present invention provides an alarm system that can be set up to alert in real time when it is time to avoid sun exposure in order to prevent further absorption of thermal radiation and reduce the risk of dermatologic changes, as can occur during outdoor activities or at the beach. In addition, thermal damage to the skin prevents the skin from adequately cooling itself and can result in increasing the risk of dehydration which further increases the temperature. The present invention helps preserve the beauty and health of people exposed to sun light and during outdoor activities while allowing full enjoyment of the sun and the benefits of sun light.

By the present invention, a method for timing sun exposure includes the steps of measuring body temperature, reporting the value measured and avoiding sun exposure for a certain period of time based on the level measured.

Hypothermia is the number one killer in outdoor activities in the U.S. and Europe. Hypothermia also decreases athletic performance and leads to injuries. It is very difficult to detect hypothermia because the symptoms are completely vague such as loss of orientation and clumsiness which are indistinguishable from general behavior. Without measuring core temperature and having an alert system when the temperature falls outside safe levels it is impossible to prevent hypothermia due to the vague symptoms. The present invention can alert an individual about hypothermia during skiing, scuba diving, mountain climbing and hiking. The present invention provides means to precisely inform when certain temperature thresholds are met, either too high or too low temperature.

The present invention continuously monitors the brain temperature and as soon as a temperature spike or fever occurs it activates diagnostics systems to detect the presence of infectious agents, which can be done locally in the BTT site, or the infectious agents can be identified in other parts of the body such as the blood stream or the eyelid pocket. The present invention can be also coupled to drug dispensing means for the automated delivery of medications in accordance with the signal produced at the BTT site including transcutaneous means, iontophoresis or by injection using a pump.

The invention also includes a tool for family planning. The system can detect spike and changes in basal temperature and identify moment of ovulation and phases of the menstrual cycle. This allows a woman to plan pregnancy or avoid pregnancy. This eliminates the need for invasive devices used for monitoring time for artificial insemination not only for humans but also animals. The invention can yet detect the start of uterine contractions (parturition) and allow a safer birth for animals. Support structures can be equally used in the BTT of animals.

The present invention also includes Automated Climate control according to the value measured at the BTT. The temperature of the user controls the temperature in the car. When the body starts to warm up, the signal from the apparatus of the invention automatically activates the air conditioner according to the user settings, alternatively it activates heat when the body is cold. This automation allows drivers to concentrate on the road and thus can reduce the risk for car crashes. It is understood that other articles that can affect body temperature can be controlled by the present invention including vehicle seats. Likewise, automated climate control at home, work, or any confined area can be achieved by activating the thermostat directly or via BlueTooth technology. Besides convenience and comfort, this automation allows saving energy since gross changes manually done in the thermostat leads to great energy expenditure.

It is understood that any body temperature measuring system can provide automated climate control or adjust temperature of articles in accordance with the principles of the present invention.

The present invention yet includes methods for reducing weight. It includes monitoring of temperature during programs for weight reduction based on increasing body heat to reduce said weight. The system alerts athletes on a weight losing program to prevent injury or death by overheating. The system can monitor temperature of people in sauna, steam rooms, spas and the like as part of weight reduction programs in order to prevent injuries and enhance results.

Yet, methods to enhance memory and performance besides preserving health by providing an automated mechanism to control ambient temperature and surrounding body temperature based on the brain temperature measured by the present invention. Human beings spent about one third of their lives sleeping. Many changes in body temperature occur during sleep. All of the metabolism and enzymatic reactions in the body are dependent on adequate level of temperature. The adequate control of ambient temperature which matches the needs of body temperature such as during sleeping have a key effect on metabolism. Adequate ambient temperature and surrounding temperature of objects which matches body temperature allow not only for people to sleep better, but also to achieve improved efficiency of enzymatic reactions which leads to improved mental ability and improved immune response. A variety of devices such as blankets, clothing, hats, mattress, pillows, or any article touching the body or in the vicinity of the body can be adapted to automatically increase or decrease temperature of said articles according to the temperature signal from the present invention.

The body naturally becomes cooler during the night and many people have restless sleep and turn continuously in bed because of that temperature effect. Since the tossing and turning occurs as involuntary movements and the person is not awake, said person cannot change the stimuli such as for instance increasing room temperature or increasing temperature of an electric blanket. The present invention automatically changes the ambient temperature or temperature of articles to match the temperature needs of the person. This is particularly useful for infants, elderly, diabetics, neuro-disorders, heart disease, and a variety of other conditions, since this population has reduced neurogenic response to changes in body temperature, and said population could suffer more during the night, have increased risk of complications besides decreased productivity due to sleep deprivation.

The invention also provides means and methods to be used with bio feedback activities. A brain temperature signal from the sensor at the BTT site produces a feedback signal as an audio tone or visual display indicating temperature and a series of tones or colors identify if the brain temperature is increasing (faster frequency and red) or decreasing (lower frequency and blue). The display means can be connected by wires to the support structure holding the sensor at the BTT site.

Head cooling does not change brain temperature. Athletes, military, firefighters, construction workers and others are at risk of heatstroke despite pouring cold water on their head or using a fan. Medically speaking that is a dangerous situation because the cool feeling sensed in the head is interpreted as internal cooling and the physical activity is maintained, when in reality the brain remains at risk of thermal induced damage and heatstroke. Other medical challenges related to temperature disturbances concern response time. The brain has a slower recovery response to temperature changes than core temperature (internal temperature measured in rectum, bladder, esophagus, and other internal means). Thus, internal measurement may indicate stable temperature while the brain temperature remains outside safe levels, with risk of induced damage to cerebral tissue, either due to hypothermia or hyperthermia. The only medically acceptable way to prevent cerebral tissue damage due to temperature disturbances is by continuous monitoring brain temperature as provided by the present invention.

The present invention utilizes a plurality of active or passive sensors incorporated in support structures for accessing a physiologic tunnel for measuring biological parameters. The present invention preferably includes all functions in a miniature semiconductor chip, which as an integrated circuit, incorporates sensor, processing and transmitting units and control circuits.

The present invention includes means for collecting thermal radiation from a BTT site, means for positioning temperature sensitive devices to receive thermal radiation from the BTT site and means for converting said thermal radiation into the brain temperature. The present invention also provides methods for determining brain temperature with said methods including the steps of collecting the thermal emission from the BTT site, producing a signal corresponding to the thermal emission collected, processing the signal and reporting the temperature level. The invention also includes means and methods for proper positioning of the temperature sensor in a stable position at the BTT site.

It is also an object of the present invention to provide support structures adapted to position a sensor on the end of a tunnel on the skin to measure biological parameters.

It is an object of the present invention to provide apparatus and methods to measure brain (core) temperature including patches, adhesives strips, elastic means, clips and the like containing sensors positioned on a physiologic tunnel.

It is an object of the present invention to provide multipurpose eyeglasses equipped with medial canthal pads containing sensors positioned on a physiologic tunnel for measuring biological parameters It is another object of the present invention to provide new methods and apparatus for measuring at least one of brain temperature, chemical function and physical function.

It is yet an object of the invention to provide apparatus that fit on both adults and children.

It is also an object of the invention to provide apparatus that report the signal produced at the tunnel by at least one of wired connection to reporting means, wireless transmission to reporting means and local reporting by audio, visual or tactile means such as by vibration incorporated in support structures.

It is yet another object of the present invention to provide apparatus that allow the wearer to avoid dehydration or overhydration (water intoxication).

It is a further object of the present invention to provide methods and apparatus that allows athletes and sports participants to increase their performance and safety.

It is yet an object of the present invention to provide support structure positioned sensors on a tunnel which can be worn at least by one of athletes during practice and competition, military during training and combat, workers during labor and the general public during regular activities.

It is another object of the present invention to increase safety and comfort in vehicles by providing automated climate control and vehicle seat control based on the core temperature of the occupants of the vehicle.

It is an object of the present invention to provide methods and apparatus that act on a second device based on the level of the biological parameter measured.

It is another object of the invention to provide methods and apparatus to preserve skin health, reduce risk of wrinkles and reduce the risk of skin cancer by preventing sun damage by thermal radiation and alerting the wearer when the temperature has reached certain thresholds.

It is also an object of the invention to provide methods and apparatus for achieving controlled weight loss based on heat-based weight loss approach.

It is also an object of the invention to provide methods and apparatus to alert athletes in a weight losing program based on increasing body temperature to prevent injury or death by overheating.

It is also an object of the invention to provide methods and apparatus that allow monitoring fever and spikes of temperature.

It is also an object of the invention to provide means for family planning by detecting time of ovulation.

It is a further object of the invention to provide methods and apparatus for the delivery of medications in accordance with the signal produced at the tunnel.

It is yet an object of the invention to provide methods and apparatus that enhance occupational safety by continually monitoring biological parameters.

It is also an object of the invention to provide an article of manufacture with a sensing apparatus positioned on a tunnel for monitoring biological parameters that can be fitted or mounted in at least one of the frame of eyeglasses, the nose pads of eyeglasses, the structure of a head mounted gear and clothing.

The invention also features transmitting the signal from the support structure to act on at least one of exercise equipment, bikes, sports gear, protective clothing, footwear and medical devices.

It is yet an object of the invention to provide support structures that transmit the signal produced at the tunnel to treadmills and other exercise machines for keeping proper hydration and preventing temperature disturbances of the user.

It is yet another object of the invention to provide apparatus and methods for monitoring biological parameters by accessing a physiologic tunnel using active or passive devices.

The invention yet features transmission of the signal from the support structures to watches, pagers, cell phones, computers, and the like.

These and other objects of the invention, as well as many of the intended advantages thereof, will become more readily apparent when reference is made to the following description taken in conjunction with the accompanying drawings.

BRIEF DESCRIPTION OF THE DRAWINGS

FIG. 1B is a computer generated thermal infrared color image of the human face showing the brain temperature tunnel.

FIG. 2A is a schematic diagram showing a physiologic tunnel.

FIG. 4B is a schematic diagram of the image in FIG. 4A.

FIG. 5B is a schematic diagram of the image in FIG. 5A.

FIG. 6A is a schematic diagram showing the brain temperature tunnel and the metabolic tunnel.

FIG. 13 is a schematic block diagram of one preferred embodiment.

FIG. 18 is a perspective view of another preferred embodiment showing a person wearing a support structure with a sensor positioned on the skin at the end of the tunnel and connected by a wire.

FIGS. 19A1, 19A2, 19B, 19C and 19D are schematic diagrams of preferred geometry and dimensions of support structures and sensing means

FIGS. 22A to 22C are perspective views of preferred embodiments showing a person wearing a support structure incorporated as a medial canthal pad with a sensor positioned on the skin at the end of the tunnel in accordance with the present invention.

FIGS. 23A and 23B are perspective views of an alternative embodiment showing a support structure comprised of modified nose pads with a sensor positioned on the skin at the end of the tunnel in accordance with the present invention.

FIG. 27 is an exploded perspective view of another preferred embodiment showing a three piece support structure.

FIG. 28A is an exploded perspective view of one preferred embodiment of support structure showing a removable medial canthal piece.

FIG. 31C is a side perspective view of part of the support structure of FIG. 31B.

FIG. 31D is a side perspective view of a medial canthal piece secured at the support structure.

DETAILED DESCRIPTION OF THE PREFERRED EMBODIMENTS

Figure 1A:
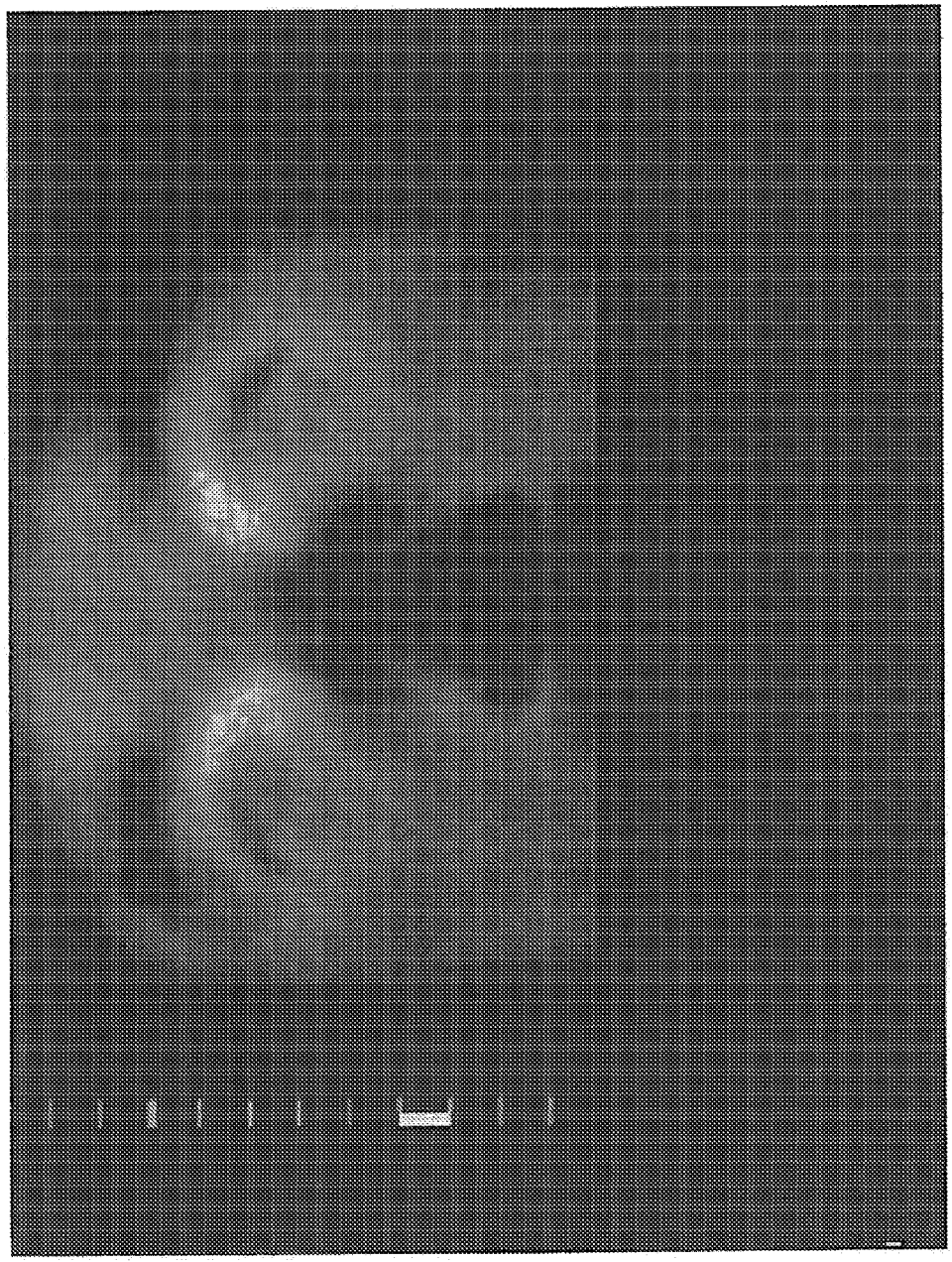
FIG. 1A is a thermal infrared image of the human face showing the brain temperature tunnel.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

FIG. 1A shows a thermal infrared image of the human face showing a physiologic tunnel. The figure shows an image of the end of the brain temperature tunnel (BTT) depicted as white bright spots in the medial canthal area and the medial half of the upper eyelid. The end of the BTT on the skin has special geometry, borders, and internal areas and the main entry point is located on the supero-medical aspect of the medial canthal area diametrically in position with the inferior portion of the upper eyelid and 4 mm medial to the medial corner of the eye. From there the boundary goes down in the medial canthal area diametrically in position with the medial corner of the eye, and within 5 mm down from the medial corner of the eye, and proceeding up to the upper eyelid with the lateral boundary beginning at the mid-part of the upper eyelid as a narrow area and extending laterally in a fan-like shape with the superior boundary beginning in the mid-half of the upper eyelid.

The scale indicates the range of temperature found in the human face. The hottest spots are indicated by the brightest white spots and the coldest areas are black, temperature between the hottest and coldest areas are seen in different hues in a gray scale. The nose is cold (seen as black) since it is primarily composed of cartilage and bones, and consequently has a lower blood volume. That is the reason why frostbite is most common in the nose.

The surrounding periocular area of the upper and lower eyelids (seen as gray) is hotter because of high vascularization and the reduced amount of adipose tissue. The skin underneath the eyelids is very thin and does not have adipose tissue either. However, the other conditions necessary to define a brain temperature tunnel are not present in this area.

The BTT requirements also include the presence of a terminal branch to deliver the total amount of heat, a terminal branch that is a direct branch from a vessel from the brain, a terminal branch that is superficially located to avoid far-infrared radiation absorption by other structures, and no thermoregulatory arteriovenous shunts. Thus, the BTT, i.e., the skin area in the medial corner of the eye and upper eyelid, is the unique location that can access a brain temperature tunnel. The skin around the eyelids delivers undisturbed signals for chemical measurements using spectroscopy and is defined as a metabolic tunnel with optimal acquisition of signals for chemical evaluation, but not for evaluation of the total radiant power of the brain.

FIG. 1B is a computer generated thermal infrared color plot image of the human face showing in detail the geometry and different areas of the brain temperature tunnel and surrounding areas. Only few creatures such as some beetles and rattle snakes can see this type of radiation, but not humans. The infrared images make the invisible into visible. Thus the geometry and size of the tunnel can be better quantified. The color plot of the isothermal lines show the peripheral area of the tunnel in red and the central area in yellow-white with the main entry point at the end of the BTT located in the superomedial aspect of the medial canthal area above the medial canthal tendon.

The main entry point is the area of most optimal signal acquisition. The image also shows the symmetry of thermal energy between the two BTT sites. Since other areas including the forehead do not have the aforementioned six characteristics needed to define a BTT, said areas have lower total radiant power seen as light and dark green. Thus the forehead is not suitable to measure total radiant power. The whole nose has very little radiant power seen as blue and purple areas, and the tip of the nose seen as brown has the lowest temperature of the face. Thus, the nose area is not suitable for measuring biological parameters.

FIG. 2A is a schematic diagram of a physiologic tunnel, more particularly a Brain Temperature Tunnel. From a physical standpoint, the BTT is a brain thermal energy tunnel characterized by a high total radiant power and high heat flow and can be characterized as a Brain Thermal Energy tunnel. The tunnel stores thermal energy and provides an undisturbed path for conveying thermal energy from one end of the tunnel in the cavernous sinus inside of the brain to the opposite end on the skin with the thermal energy transferred to the surface of the skin at the end of the tunnel in the form of far-infrared radiation. High heat flow occurs at the end of tunnel which is characterized by a thin interface, and the heat flow is inversely proportional to the thickness of the interface.

The total radiated power (P) at the end of the tunnel is defined by $P = \sigma * e * A * T^4$, where $\sigma$ is the Stefan-Boltzman constant with a value $\sigma = 5.67 \times 10^{-8}$ $W \cdot m^{-2} \cdot K^{-4}$ and e is the emissivity of the area. Since the end of the tunnel provides an optimal area for radiation, the total power radiated grows rapidly as the temperature of the brain increases because of the $T^4$ term in the equation. As demonstrated in the experiments in the present invention mentioned, the radiated power in the BTT occurred at a faster rate than the radiated power in the tongue and oral cavity.

The BTT site on the skin is a very small area measuring only less than 0.5% of the body surface area. However, this very small skin region of the body provides the area for the optimal signal acquisition for measuring both physical and chemical parameters.

FIG. 2A shows the brain 10 with the thermal energy 12 stored in its body. The BTT 20 include the brain 10, the thermal energy stored in the brain 12, the thermal energy stored in the tunnel 14 and the thermal energy 16 transferred to the exterior at the end of the tunnel. The thermal energy 12, 14, 16 is represented by dark arrows of same size and shape. The arrows have the same size indicating undisturbed thermal energy from one end of the tunnel to the other and characterized by equivalent temperature within the tunnel.

Thermal energy from the sinus cavernous in the brain 10 is transferred to the end of the tunnel 16 and a rapid rate of heat transfer occurs through the unimpeded cerebral venous blood path. The tunnel also has a wall 18 representing the wall of the vasculature storing the thermal energy with equivalent temperature and serving as a conduit from the inside of the body 10 to the exterior (skin surface) 19 which ends as a terminal vessel 17 transferring the total amount of thermal energy to said skin 19.

The skin 19 is very thin and allows high heat flow. The thickness of skin 19 is negligible compared to the skin 39, 49 in non-tunnel areas 30 and 40 respectively. Due to the characteristics of skin 19, high heat flow occurs and thermal equilibrium is achieved rapidly when a sensor is placed on the skin 19 at the end of the BTT 20.

In other areas of skin in the face and in the body in general, and in the exemplary non-tunnel areas 30 and 40 of FIG. 2 several interfering phenomena occur besides the lack of direct vasculature connection to the brain, and includes self-absorption and thermal gradient. 1. Self-absorption: This relates to the phenomena that deep layers of tissue selectively absorb wavelengths of infrared energy prior to emission at the surface. The amount and type of infrared energy self-absorbed is unknown. At the surface those preferred emissions are weak due to self-absorption by the other layers deriving disordered thermal emission and insignificant spectral characteristic of the substance being analyzed being illustratively represented by the various size, shapes and orientations of arrows 34a to 36g and 44a to 46g of FIG. 2. Self-absorption in non-tunnel areas thus naturally prevents useful thermal emission for measurement to be delivered at the surface. 2. Thermal gradient: there is a thermal gradient with the deeper layers being warmer than the superficial layers, illustratively represented by thicker arrows 36d and 46d in the deeper layers compared to thinner arrows 36e and 46e located more superficially. There is excessive and highly variable scattering of photons when passing through various layers such as fat and other tissues such as muscles leading to thermal loss.

Contrary to that, the tunnel area 20 is homogeneous with no absorption of infrared energy and the blood vessels are located on the surface. This allows undisturbed delivery of infrared energy to the surface of the skin 19 and to a temperature detector such as an infrared detector placed in apposition to said skin 19. In the BTT area there is no thermal gradient since there is only a thin layer of tissue 19 with terminal blood vessel 17 directly underneath said thin interface skin 19. The thermal energy 16 generated by the terminal blood vessel 17 exiting to the surface skin 19 corresponds to the undisturbed brain (true core) temperature of the body. The preferred path for achieving thermal equilibrium with brain tissue temperature is through the central venous system which exits the brain and enters the orbit as the superior ophthalmic vein. The arterial blood is 0.2 to 0.3 degrees Celsius lower when compared to the central venous blood, and said arterial blood is not the actual equivalent of the brain temperature. Thus although arterial blood may be of interest in certain occasions, the venous system is the preferred carrier of thermal energy for measurement of brain temperature. Arterial blood temperature may be of interest to determine possible brain cooling by the arterial blood in certain circumstances.

Non-tunnel areas 30 and 40 are characterized by the presence of heat absorbing elements. The non-tunnel areas 30 and 40 are defined by broken lines characterizing the vulnerability of interference by heat absorbing constituents and by the disorganized transferring of heat in said non-tunnel areas 30 and 40. Various layers and other constituents in non-tunnel areas 30 and 40 selectively absorb infrared energy emitted by the deeper layers before said energy reaches the surface of skin, and the different thermal energy and the different areas are represented by the different shapes and sizes of arrows and arrows heads.

Non-tunnel area 30 can be representative of measuring temperature with a sensor on top of the skin anatomically located above the heart 32. White arrows 34 represent the thermal energy in the heart 32. Non-tunnel area 30 includes the heart 32 and the various blood vessels and its branches 36a, 36b, 36c, 36d storing thermal energy.

Different amounts of heat are transferred and different temperatures measured depending on the location and anatomy of blood vessels 36a, 36b, 36c. The blood vessels branch out extensively from the main trunk 34a. The non-tunnel area 30 also includes heat absorbing structures 37 such as bone and muscles which thermal energy 34 from the heart 32 need to be traversed to reach the skin 39. The non-tunnel area 30 also includes a variable layer of fat tissue 38 which further absorbs thermal energy. The reduced amount of thermal energy reaching the skin surface 39 due to the presence of fat 38 is represented by the arrows 36d and 36e, in which arrow 36d has higher temperature than arrow 36e. Non-tunnel area 30 also includes a thick skin 39 with low heat flow represented by arrows 36f.

The thick skin 39 corresponds to the skin in the chest area and fat layer 38 corresponds to the variable amount of fat present in the chest area. Arrows 36g represent the disordered and reduced total radiant power delivered after said thermal energy traverses the interfering constituents in the non-tunnel area including a thick interface and heat absorbing structures. In addition, BTT 20 has no fat layer as found in non-tunnel areas 30 and 40. Lack of a thick interface such as thick skin and fat, lack of thermal barriers such as fat, and lack of heat absorbing elements such as muscles allows undisturbed emission of radiation at the end of the BTT. Lack of a thick interface such as thick skin and fat, lack of thermal barriers such as fat, and lack of heat absorbing elements such as muscles allowed undisturbed emission of radiation at the end of the BTT.

Yet referring to FIG. 2, non-tunnel area 40 can be representative of measuring temperature with a sensor on top of the skin in the arm 42. The heat transfer in non-tunnel area 40 has some similarity with non-tunnel area 30 in which the end result is a disordered and reduced total radiant power not representative of the temperature at the opposite end internally. The blood vessels branch out extensively from the main trunk 44a. Thermal energy and temperature in blood vessels 46a, 46b, 46c is different than in areas 36a, 36b, 36c. The structures that thermal energy 44 needs to traverse to reach the skin are also different compared to non-tunnel 30. The amount of heat absorbing structures 47 is different and thus the end temperature at non-tunnel 40 is also different when compared to non-tunnel area 30. The amount of fat 48 also varies which changes the energy in areas area 46d and 46e, wherein 46d is deeper than area 46e. Thick skin 49 also reduces heat flow and the temperature of the area 46f. Reduction of radiant power indicated by arrow 46g when compared to radiant power 36g is usually quite different, so different skin temperature is measured depending on the area of the body. This applies to the whole skin surface of the body, with the exception of the skin at the end of the BTT.

Measurements of internal temperature such as rectal do not have the same clinical relevance as measurement in the brain. Selective brain cooling has been demonstrated in a number of mammalian species under laboratory conditions and the same process could occur in humans. For instance the temperature in bladder and rectum may be quite different than the brain. High or low temperature in the brain may not be reflected in the temperature measured in other internal organs.

Figure 2B:
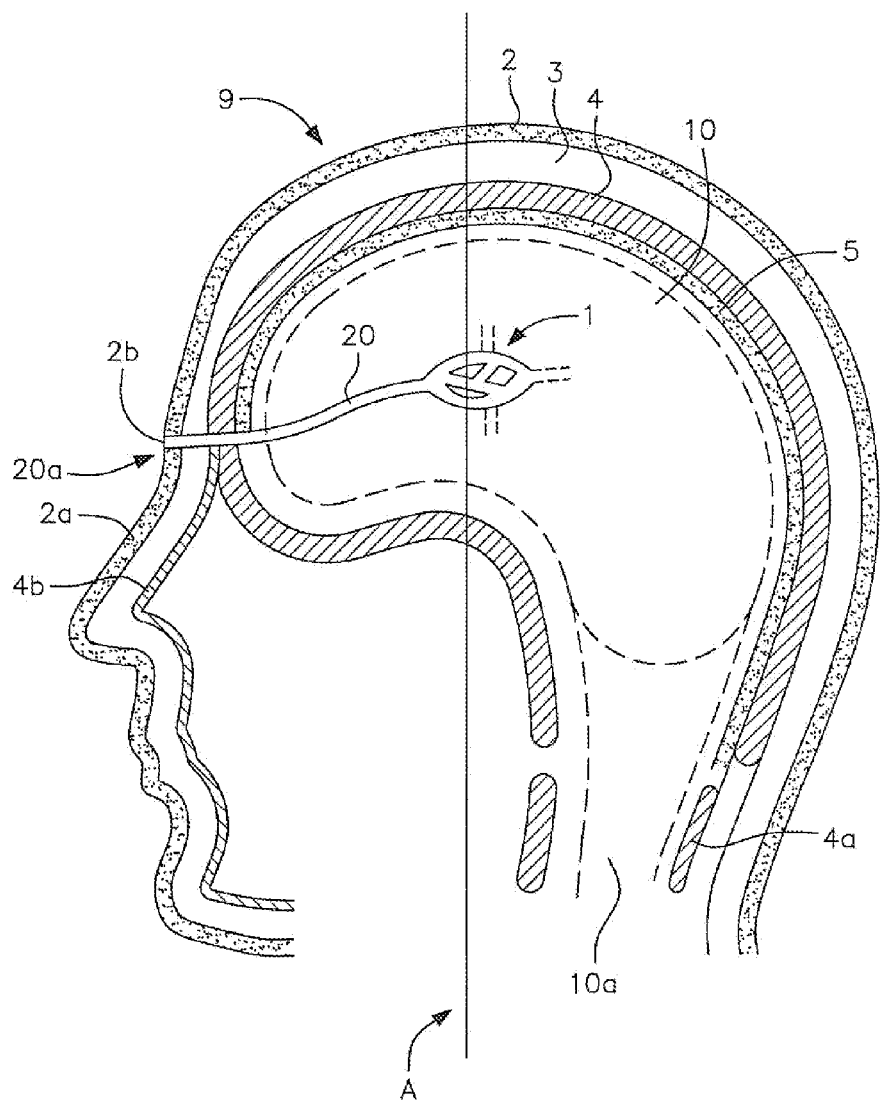
FIG. 2B is a cross-sectional schematic diagram of the human head showing the tunnel.

FIG. 2B is a cross-sectional schematic diagram of the human head 9 showing the brain 10, spinal cord 10a, the tunnel 20 represented by the superior ophthalmic vein, the cavernous sinus 1, which is the thermal energy storage compartment for the brain, and the various insulating barriers 2, 2a, 3, 4, 4a, 4b, 5 that keep the brain as a completely thermally insulated structure. Insulating barriers include skin 2 corresponding to the scalp, skin 2a corresponding to the skin covering the face, fat 3 covering the whole surface of the skull and face, skull bone 4, spinal bone 4a surrounding spinal cord 10a, facial bone 4b covering the face, and cerebral spinal fluid (CSF) 5. The combined thickness of barriers 2,3,4,5 insulating the brain can reach 1.5 cm to 2.0 cm, which is a notable thickness and the largest single barrier against the environment in the whole body. Due to this completely confined environment the brain cannot remove heat efficiently and heat loss occurs at a very lower rate. Skin 2 corresponds to the scalp which is the skin and associated structure covering the skull and which has low thermal conductivity and works as an insulator. Fat tissue 3 absorbs the majority of the far-infrared wavelength and works as a thermal buffer. Skull bone 4 has low thermal conductivity and the CSF works as a physical buffer and has zero heat production.

The heat generated by metabolic rate in the brain corresponds to 20% of the total heat produced by the body and this enormous amount of heat is kept in a confined and thermally sealed space. Brain tissue is the most susceptible tissue to thermal energy induced damage, both high and low levels of thermal energy. Because of the thermal insulation and physical inability of the brain to gain heat or lose heat, both hypothermic (cold) and hyperthermic (hot) states can lead to brain damage and death can rapidly ensue, as occur to thousands of healthy people annually besides seizures and death due to high fever in sick people. Unless appropriate and timely warning is provided by continuously monitoring brain temperature anyone affected by cold or hot disturbances is at risk of thermal induced damage to the brain.

FIG. 2B also shows a notably small entry point 20a measuring less than 0.5% of the body surface which corresponds to the end of the tunnel 20 on the skin 2b. The skin 2b is extremely thin with a thickness of 1 mm or less compared to the skin 2 and 2a which are five fold or more, thicker than skin 2b.

The tunnel 20 starts at the cavernous sinus 1 which is a conduit for venous drainage for the brain and for heat transfer at the end of the tunnel 20 as a radiant energy. Tunnel 20 provides an obstructed passage to the cavernous sinus 1, a structure located in the middle of the brain, and which is in direct contact with the two sources of heat to the brain: 1) thermal energy produced due to metabolic rate by the brain and carried by the venous system; and 2) thermal energy delivered by the arterial supply from the rest of the body to the brain. This direct contact arrangement is showed in detail in FIG. 2C, which is a coronal section of FIG. 2B corresponding to the line marked "A".

Figure 2C:
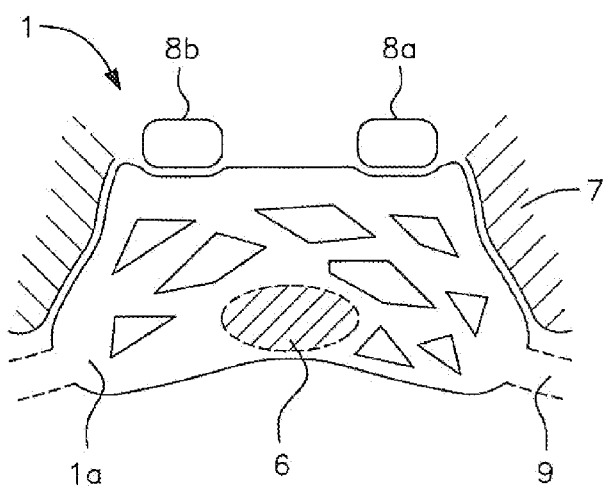
FIG. 2C is a coronal section schematic diagram showing the cavernous sinus of FIG. 2B.

FIG. 2C is a coronal section through the cavernous sinus 1 which is a cavity-like structure with multiple spaces 1a filled with venous blood from the veins 9 and from the superior ophthalmic vein 6. Cavernous sinus 1 collects thermal energy from brain tissue 7, from arterial blood of the right and left internal carotid arteries 8a, 8b, and from venous blood from vein 9. All of the structures 7, 8a, 8b, 9 are disposed along and in intimate contact with the cavernous sinus 1. A particular feature that makes the cavernous sinus 1 of the tunnel a very useful gauge for temperature disturbances is the intimate association with the carotid arteries 8a, 8b. The carotid arteries carry the blood from the body, and the amount of thermal energy delivered to the brain by said vessels can lead to a state of hypothermia or hyperthermia. For instance during exposure to cold, the body is cold and cold blood from the body is carried to the brain by internal carotid arteries 8a, 8b, and the cavernous sinus 1 is the entry point of those vessels 8a, 8b to the brain.

As soon as cold blood reaches the cavernous sinus 1 the corresponding thermal energy state is transferred to the tunnel and to the skin surface at the end of the tunnel, providing therefore an immediate alert even before the cold blood is distributed throughout the brain. The same applies to hot blood for instance generated during exercise which can lead to a 20 fold heat production compared to baseline. This heat carried by vessels 8a, 8b is transferred to the cavernous sinus 1 and can be measured at the end of the tunnel. In addition, the thermal energy generated by the brain is carried by cerebral venous blood and the cavernous sinus 1 is a structure filled with venous blood.

Figure 3B:
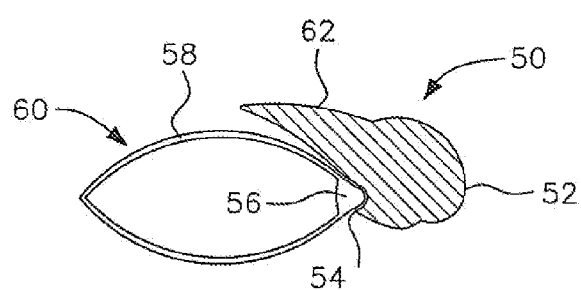
FIG. 3B is a schematic diagram of the image in FIG. 3A showing the geometry at the end of the tunnel.
Figure 3A:
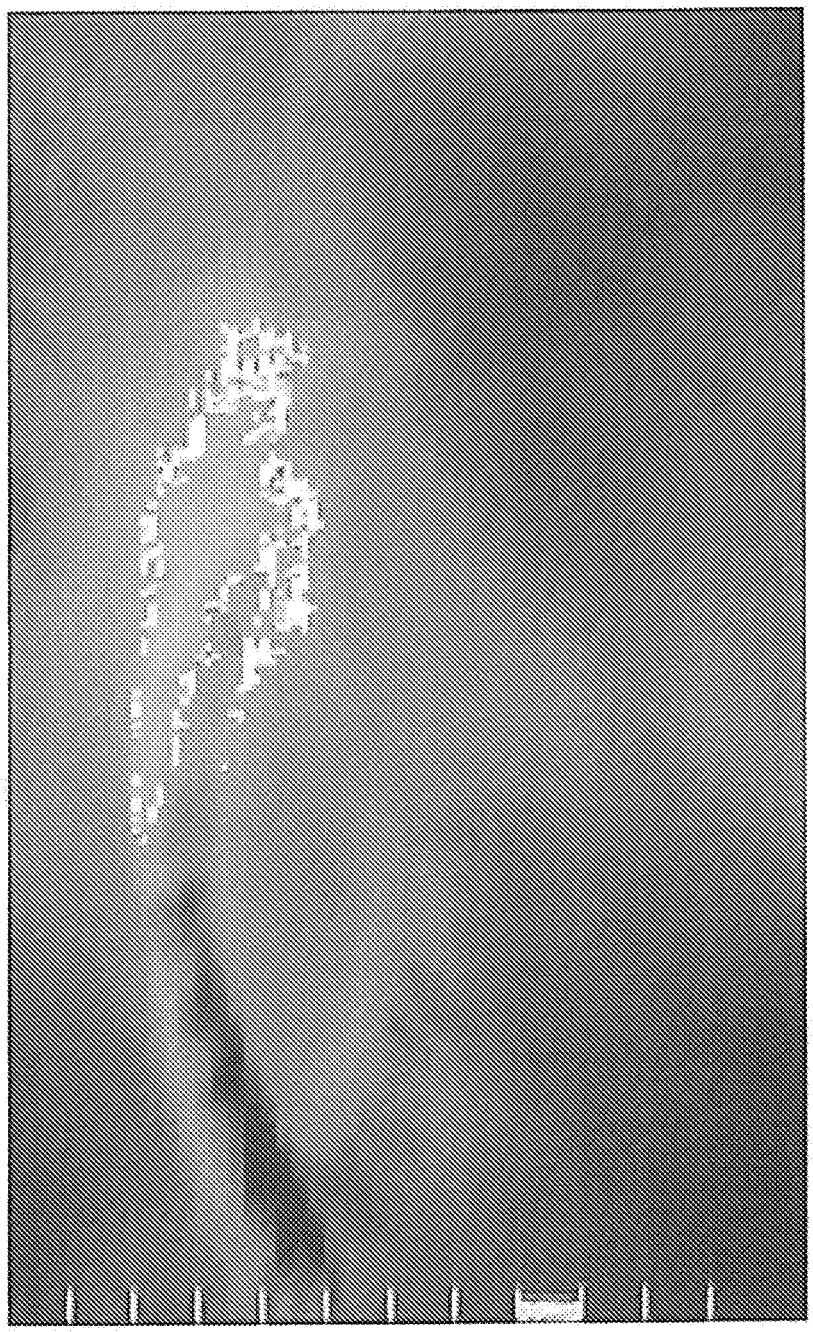
FIG. 3A is a thermal infrared image of the human face showing the tunnel.

FIG. 3A is a thermal infrared image of the human face in which the geometry of the end of the tunnel on the skin can be visualized. The white bright spots define the central area of the tunnel. FIG. 3B is a schematic diagram of an exemplary geometry on the skin surface at the end of the tunnel. The medial aspect 52 of the tunnel 50 has a round shape. The lateral aspect 54 borders the upper lid margin 58 and caruncle 56 of the eye 60. The tunnel extends from the medial canthal area 52 into the upper eyelid 62 in a horn like projection.

Figure 4A:
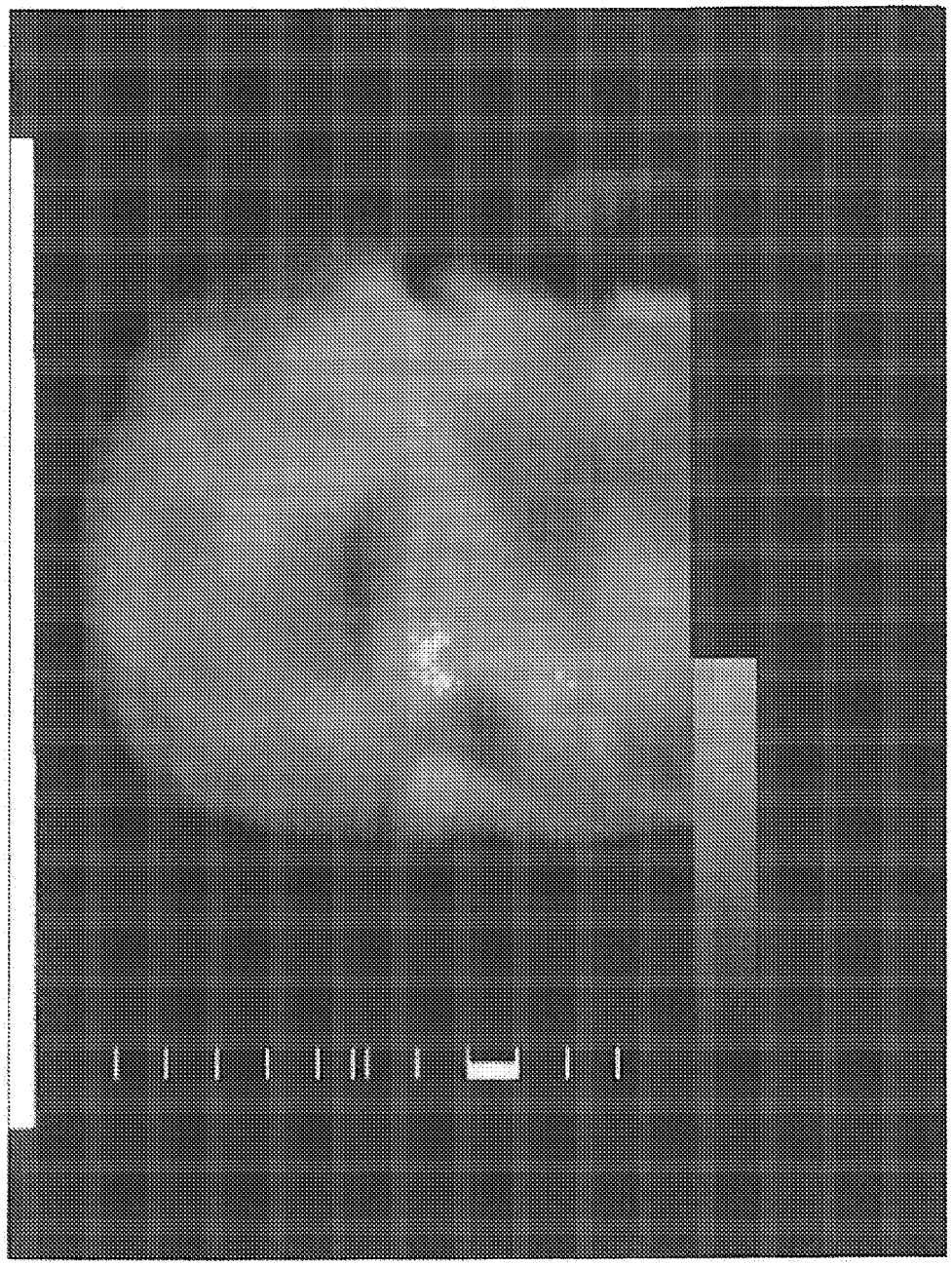
FIG. 4A is a thermal infrared image of the side of the human face showing a general view of the main entry point of the brain temperature tunnel.

The internal areas of the tunnel 50 include the general area for the main entry point and the main entry point as shown in FIGS. 4A to 5D. FIG. 4A is a thermal infrared image of the side of the human face showing a general view of the main entry point of the brain temperature tunnel, seen as white bright points located medial and above the medial canthal corner. FIG. 4B is a diagram showing the general area 70 of the main entry point and its relationship to the eye 60, medial canthal corner 61, eyebrow 64, and nose 66. The general area 70 of the main entry point provides an area with more faithful reproduction of the brain temperature since the area 70 has less interfering elements than the peripheral area of the tunnel.

Figure 5A:
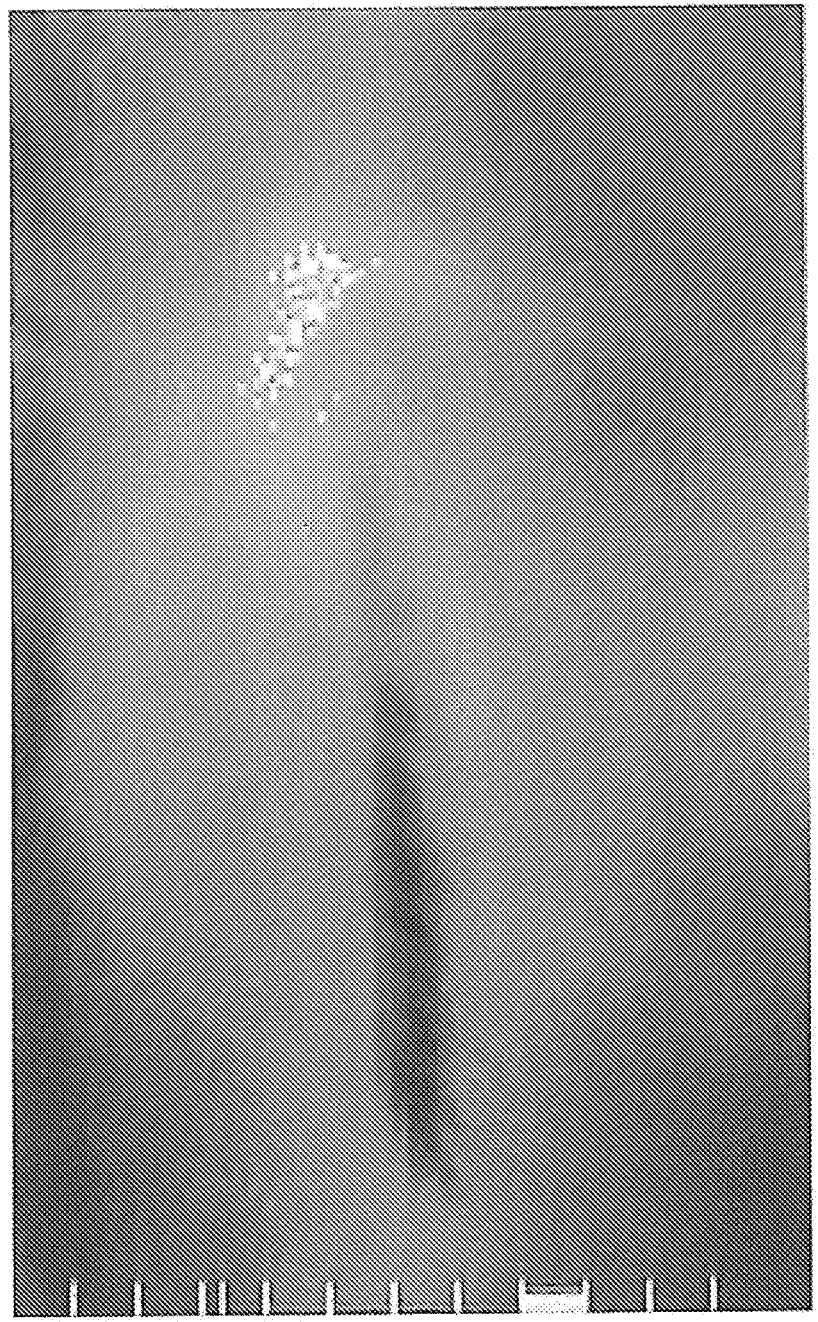
FIG. 5A is a thermal infrared image of the front of the human face showing the main entry point of the brain temperature tunnel.

FIG. 5A is a thermal infrared image of the front of the human face with the right eye closed showing the main entry point of the brain temperature tunnel seen as white bright spots above and medial to the medial canthal corner. With closed eyes it is easy to observe that the radiant power is coming solely from the skin at the end of BTT.

FIG. 5B is a diagram showing the main entry point 80 and its relationship to the medial canthal corner 61 of closed eye 60 and eyelids 62. The main entry point 80 of the tunnel provides the area with the most faithful reproduction of the brain temperature since the area 80 has the least amount of interfering elements and is universally present in all human beings at an equivalent anatomical position. The main entry point 80 has the highest total radiant power and has a surface with high emissivity. The main entry point 80 is located on the skin in the superior aspect of the medial canthal area 63, in the supero-medial aspect of the medial canthal corner 61.

Figure 5C:
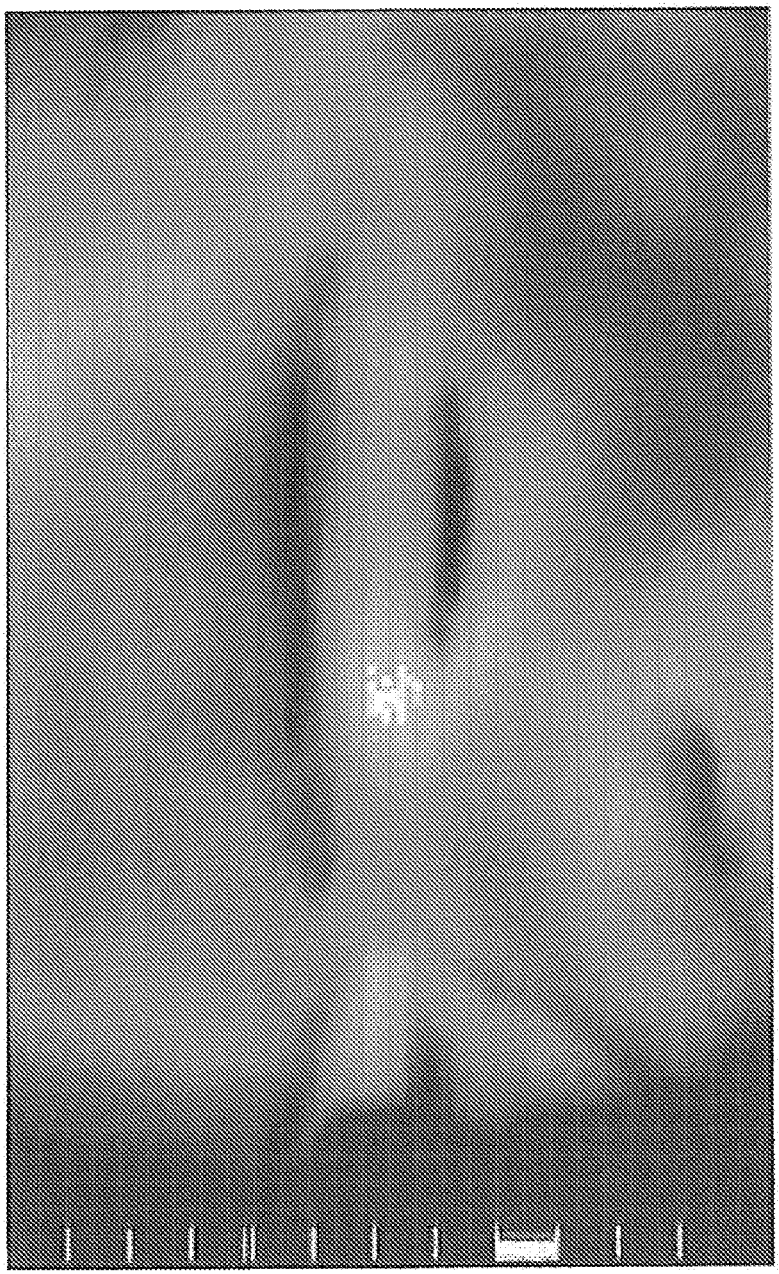
FIG. 5C is a thermal infrared image of the side of the human face in FIG. 5A showing the main entry point of the brain temperature tunnel.

FIG. 5C is a thermal infrared image of the side of the human face in FIG. 5A with the left eye closed showing a side view of the main entry point of the brain temperature tunnel, seen as bright white spots. It can be observed with closed eyes that the radiant power is coming solely from the skin at the end of BTT.

Figure 5D:
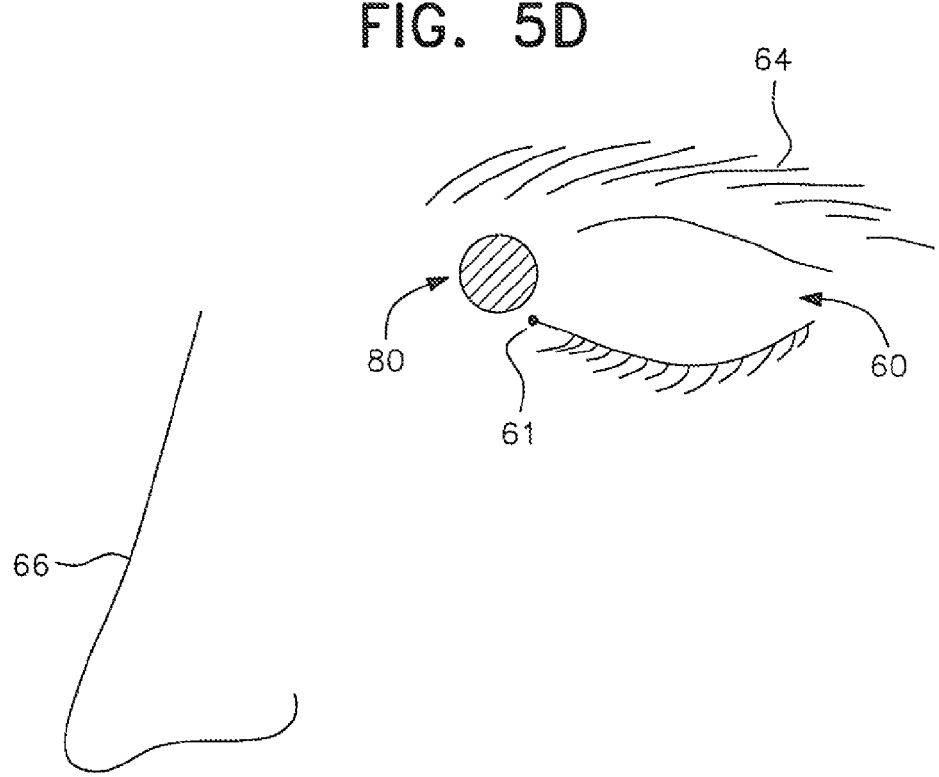
FIG. 5D is a schematic view of the image in FIG. 5C.

FIG. 5D shows the main entry point 80 in the superior aspect of the medial canthal area above the medial canthal corner 61, and also shows the position of main entry point 80 in relation to the eye 60, eyebrow 64 and nose 66. Support structures can precisely position sensing means on top of the main entry point of the tunnel because the main entry point is completely demarcated by anatomic landmarks. In general the sensor is positioned on the medial canthal skin area above the medial canthal corner and adjacent to the eye. Although indicators can be placed on support structures to better guide the positioning of the sensor, the universal presence of the various permanent anatomic landmarks allows the precise positioning by any non-technical person.

The main entry point is the preferred location for the positioning of the sensor by the support structure, but the placement of a sensor in any part of the end of the tunnel including the general entry point area and peripheral area provides clinically useful measurements depending on the application. The degree of precision needed for the measurement will determine the positioning of the sensor. In cases of neurosurgery, cardiovascular surgery, or other surgical procedure in which the patient is at high risk of hypothermia or malignant hyperthermia, the preferred position of the sensor is at the main entry point. For recreational or professional sports, military, workers, fever detection at home, wrinkle protection in sunlight, and the like, positioning the sensor in any part of the end of the tunnel area provides the precision needed for clinical usefulness.

Figure 6:
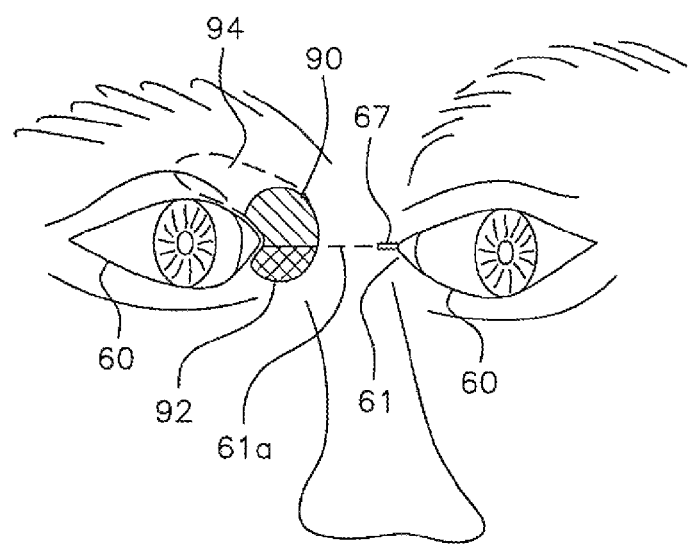
FIG. 6 is a schematic view of the face showing the general area of the main entry point of the tunnel and peripheral parts.

In accordance with the present invention, FIG. 6 is a schematic view of the face showing the general area of the main entry point of the tunnel 90 and the overall area of the end of the tunnel and its relationship to the medial canthal tendon 67. The end of the tunnel includes the general main entry point area 90 and the upper eyelid area 94. The area 90 has a peripheral portion 92. Both medial canthal areas have a medial canthal tendon and the left eye is used to facilitate the illustration. The medial canthal tendon 67 arises at the medial canthal corner 61 of eye 60. The left medial canthal tendon 67 is diametrically opposed to the right medial canthal tendon as shown by broken lines 61a which begins at the medial corner of the eye 61. Although the main entry point is above the medial canthal tendon 67, some of the peripheral area 92 of the tunnel is located below tendon 67.

FIG. 6A is a schematic diagram showing two physiologic tunnels. The upper figure shows the area corresponding to the BTT 10. The lower figure shows an area corresponding to a metabolic tunnel 13 which includes the upper eyelid area 13a and lower eyelid area 13b seen as light blue areas in FIG. 1B. For measuring the concentration of chemical substances the total radiant power is not mandatory. The key aspect for clinical useful spectroscopic measurements is signal coming from the cerebral area and the reduction or elimination of interfering constituents, and the main interfering constituent is adipose tissue. By removing adipose tissue and receiving spectral information carried by a vasculature from the brain, precise and clinical measurements can be achieved. The sensors supported by support structure are adapted to have a field of view that matches in total or in part the metabolic tunnel 13 for capturing thermal radiation from said tunnel 13.

Figure 7A:
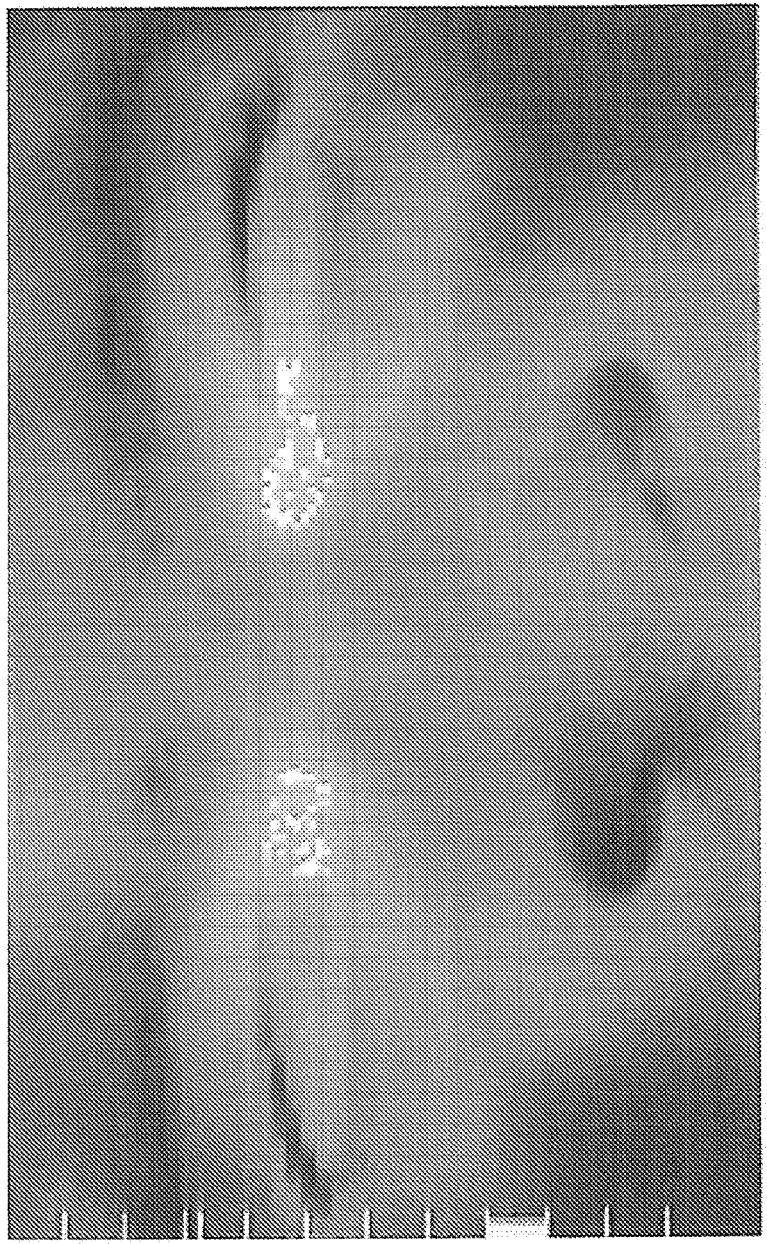
FIGS. 7A and 7B are thermal infrared images of the human face before and after cold challenge.
Figure 7B:

To determine the thermal stability of the tunnel area in relation to environmental changes, cold and heat challenge tests were performed. FIGS. 7A and 7B are thermal infrared images of an exemplary experiment showing the human face before and after cold challenge. In FIG. 7A the face has a lighter appearance when compared to FIG. 7B which is darker indicating a lower temperature. The nose in FIG. 7A has an overall whitish appearance as compared to the nose in FIG. 7B which has an overall darker appearance. Since the areas outside the tunnel have thermoregulatory arteriovenous shunts and interfering constituents including fat, the changes in the temperature of the environment are reflected in said areas. Thus measurements in those non-tunnel areas of the face reflect the environment instead of the actual body temperature. The non-tunnel areas of the skin in the face and body can change with the changes in ambient temperature. The radiant power of the tunnel area remains stable and there is no change in the amount of thermal energy demonstrating the stability of the thermal emission of the area. Changes of thermal radiation at the tunnel area only occur when the brain temperature changes, which provides the most reliable measurement of the thermal status of the body.

Figure 8A:
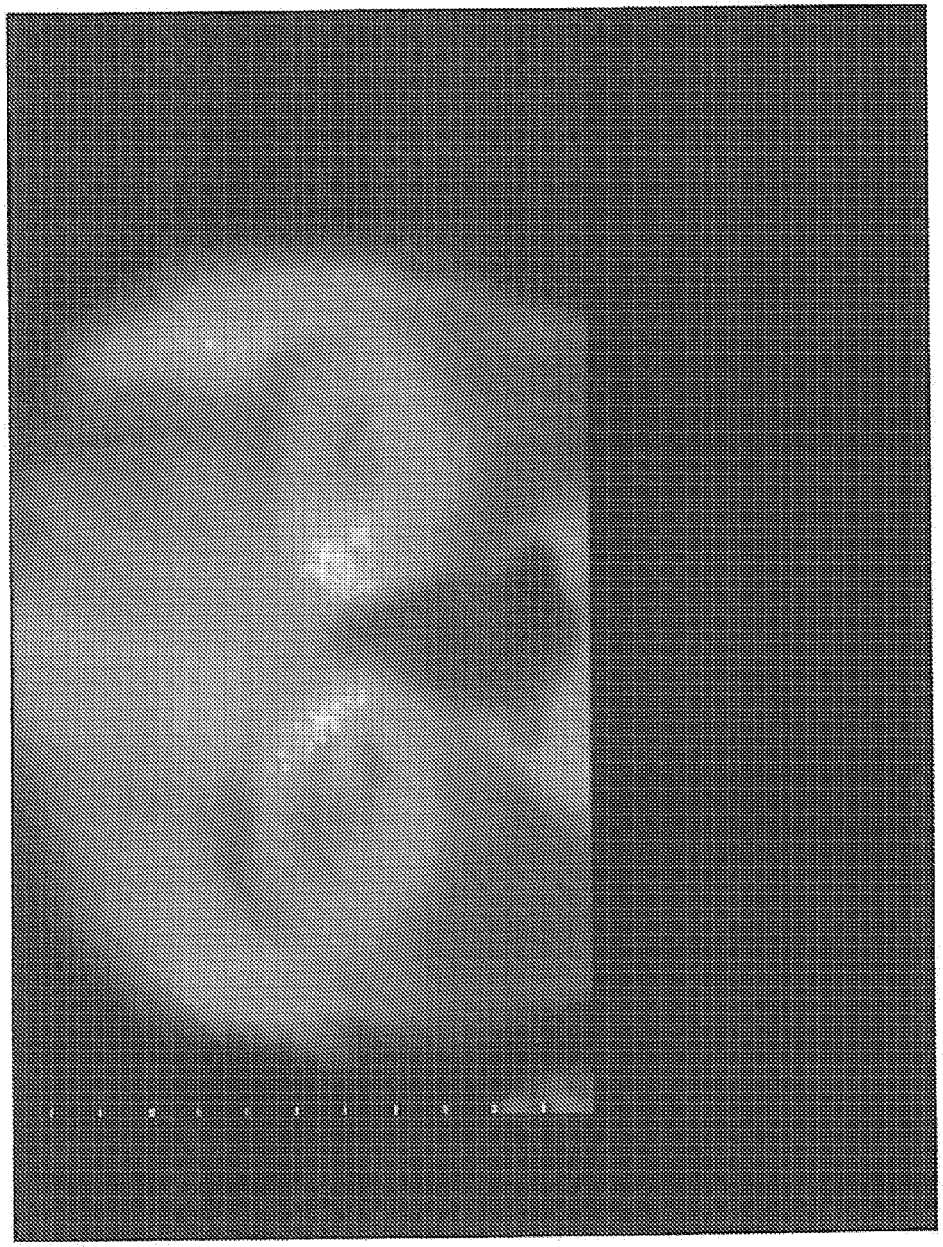
FIGS. 8A and 8B are thermal infrared images of the human face of different subjects showing the tunnel.
Figure 8B:
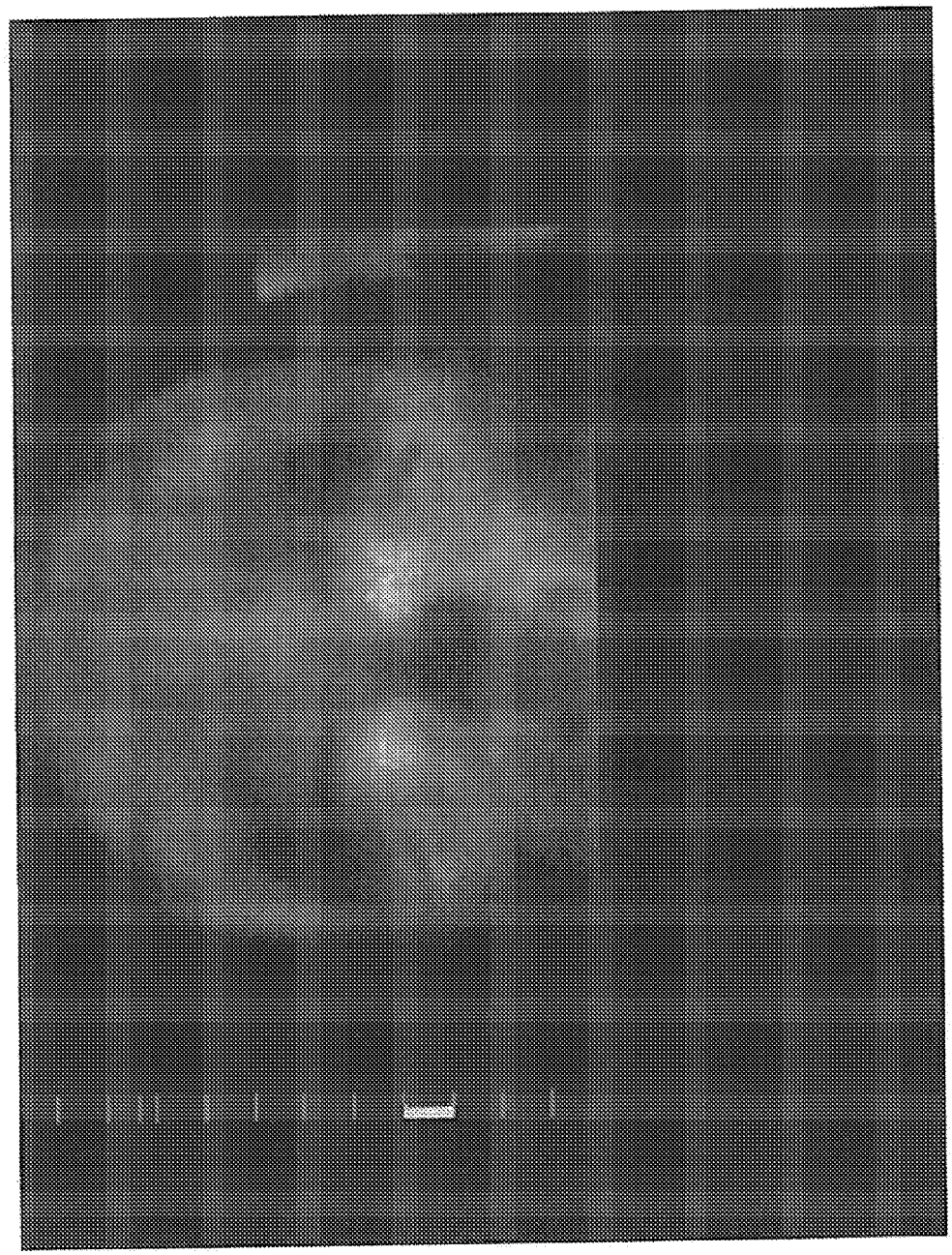
Figure 9A:
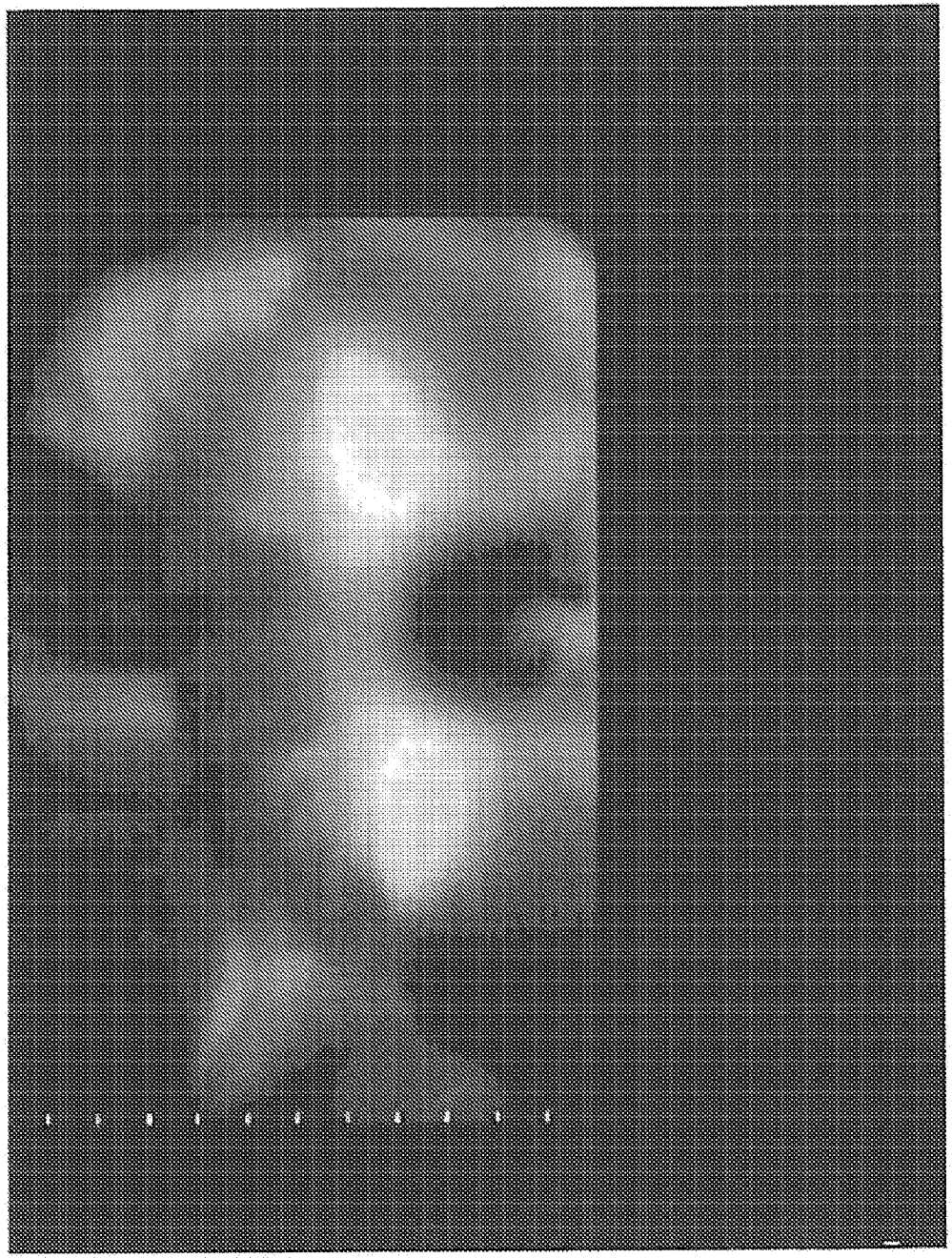
FIGS. 9A and 9B are thermal infrared images of animals showing a tunnel.
Figure 9B:
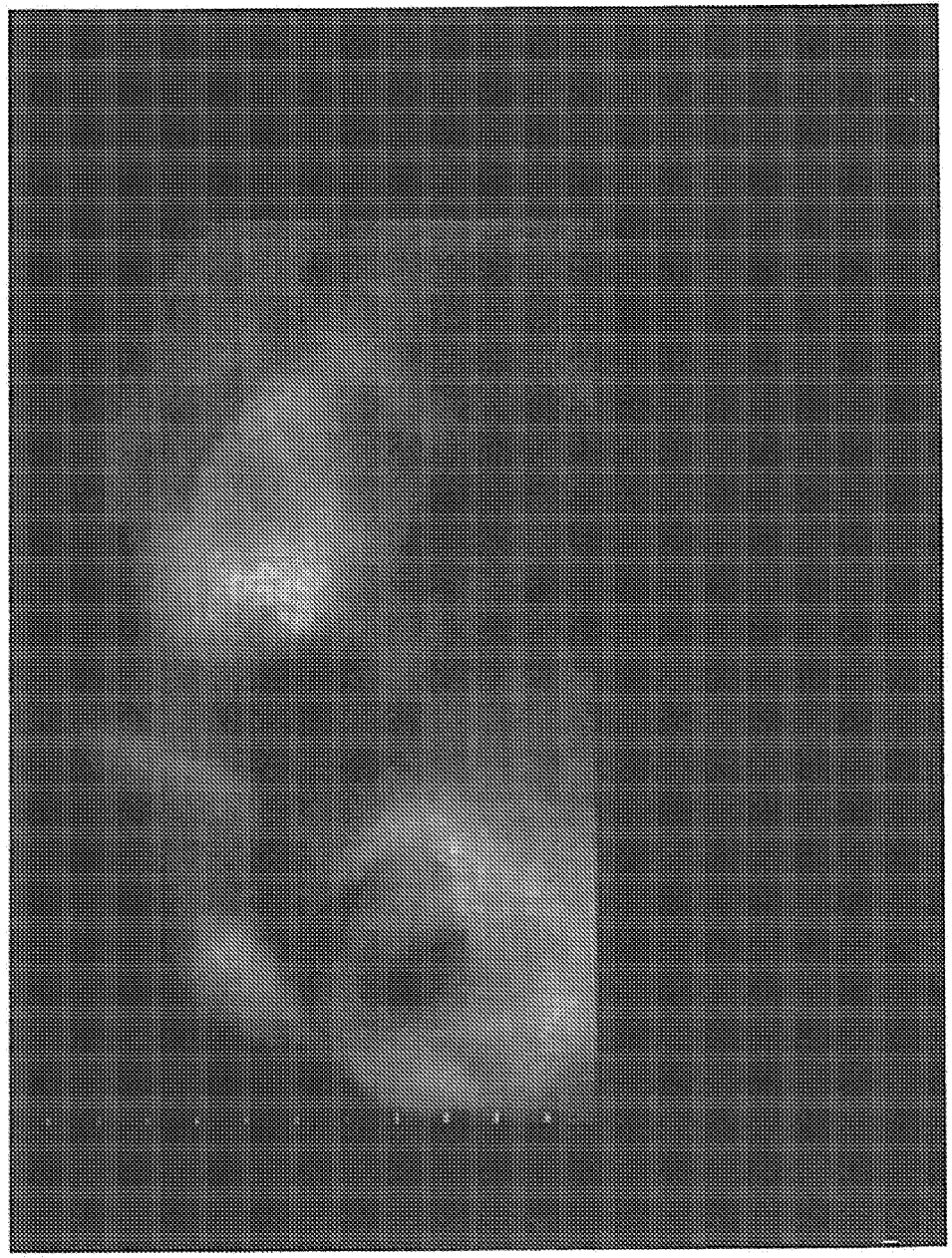

FIGS. 8A and 8B are thermal infrared images of the human face of different subjects showing the tunnel seen as bright white spots in the medial canthal area. The physiologic tunnel is universally present in all individuals despite anatomic variations and ethnic differences. FIGS. 9A and 9B are thermal infrared image showing that the tunnel seen as bright white spots are equally present in animals, illustrated here by a cat (FIG. 9A) and a dog (FIG. 9B).

Figure 10:
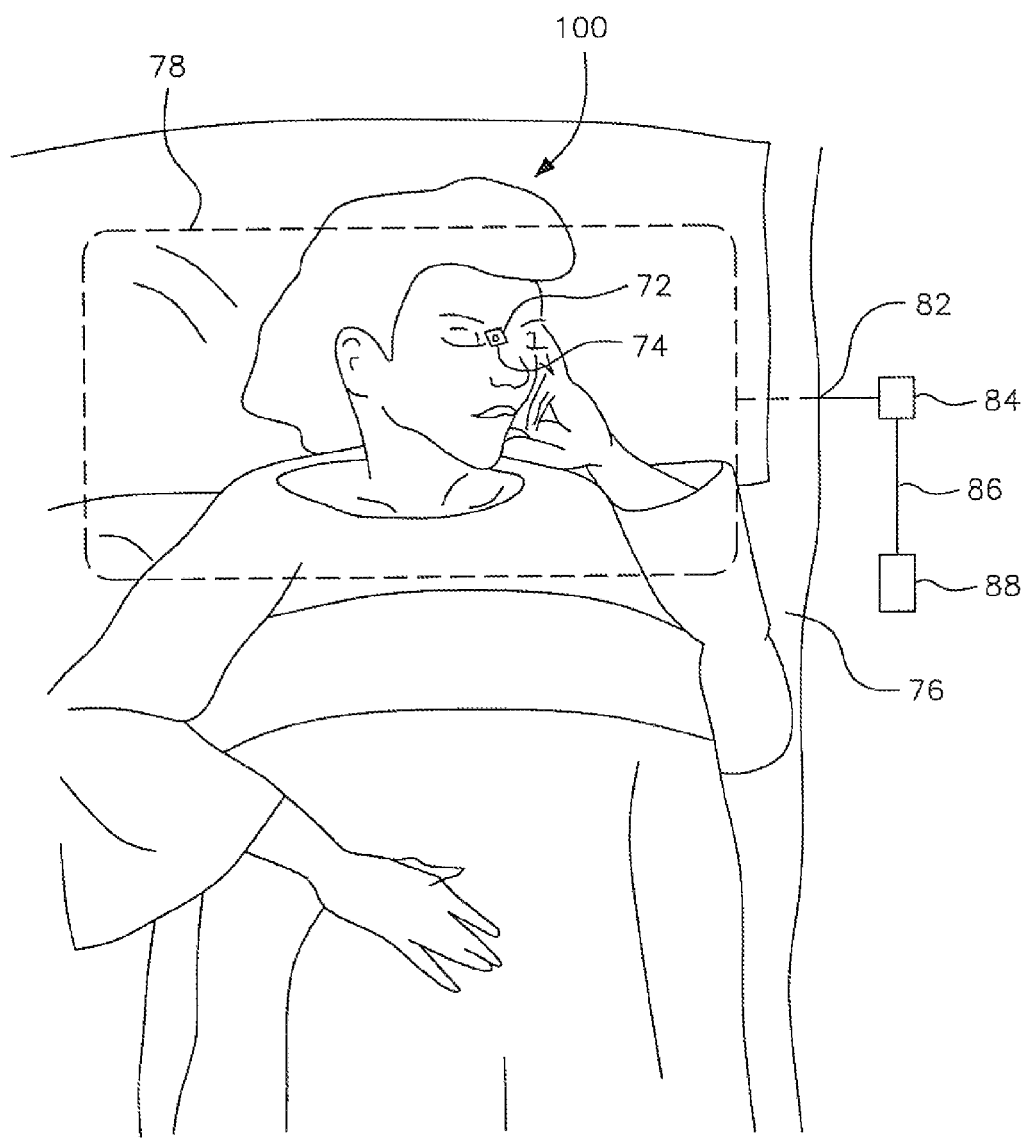
FIG. 10 is a perspective view of a preferred embodiment showing a person wearing a support structure comprised of a patch with a passive sensor positioned on the skin at the end of the tunnel in accordance with the present invention.

A preferred embodiment includes a temperature sensor with measurement processing electronics housed in a patch-like support structure which positions a passive sensor directly in contact with the skin over the brain temperature tunnel site. Accordingly, FIG. 10 is a perspective view of a preferred embodiment showing a person 100 wearing a support structure comprised of a patch 72 with a passive sensor 74 positioned on the skin at the end of the tunnel. Person 100 is laying on a mattress 76 which contains antenna 78. Wire 82 extends from antenna 78 to controller unit 84 with said controller 84 communicating with device 88 by communication line 86. Exemplary device 88 includes a decoding and display unit at the bedside or at the nursing station. It is understood that controller unit 84 besides communicating by cable 86, can also contain wireless transmission means to wirelessly transmit the signal acquired to a remote station. This inductive radio frequency powered telemetry system can use the same antenna 78 to transfer energy and to receive the signal.

The antenna 78 can be secured to a mattress, pillow, frame of a bed, and the like in a removable or permanent manner. The preferred embodiment includes a thin flat antenna encapsulated by a flexible polymer that is secured to a mattress and is not visible to the user. Alternatively an antenna can be placed in any area surrounding the patient, such as on a night stand.

The antenna 78 and controller unit 84 works as a receiver/interrogator. A receiver/interrogator antenna 78 causes RF energy to radiate to the microcircuit in the patch 72. This energy would be stored and converted for use in the temperature measurement process and in the transmission of the data from the patch 72 to the antenna 78. Once sufficient energy has been transferred, the microcircuit makes the measurement and transmits that data to the receiver/interrogator antenna 78 with said data being processed at controller 84 and further communicated to device 88 for display or further transmission. The switching elements involved in the acquisition of the sensor data (measurement of the energy) is done in a sequence so that the quantized answer is available and stored prior to the activation of the noise-rich transmission signal. Thus the two inherently incompatible processes successfully coexist because they are not active simultaneously.

The capability of the RF link to communicate in the presence of noise is accomplished by spreading the spectral content of the transmitted energy in a way that would inherently add redundancy to the transmission while reducing the probability that the transmission can ever be interpreted by the receiver/interrogator 78 as another transmission or noise that would cause the receiver/interrogator 78 to transmit and display incorrect information. This wireless transmission scheme can be implemented with very few active elements. The modulation purposely spreads the transmission energy across the spectrum and thus provides noise immunity and the system can be ultimately be produced via batch processing and thus at a very low cost.

Since the energy to operate sensor 74 in patch 72 comes from the antenna 78, the microcircuit in said patch 72 can be very small and ultra-thin. Size of the patch 72 would be further minimized to extremely small dimensions by the design approach that places all the processing function of the RF link in the controller unit 84 working as a receiver. RF messaging protocol and the control of the sensor 74 resides in the receiver/interrogator controller 84 powered by commercially available batteries or by AC current. Thus the RF messaging protocol and the control of the sensor 74 is directly controlled by the MCU of controller 84. The circuit resident in the patch 72 is preferably completely self-contained. The sensing system 74 in the patch 72 is preferably a silicon microcircuit containing the circuits needed to support the sensor, quantatize the data from the sensor, encode the data for radio frequency transmission, and transmit the data, besides power conditioning circuits and digital state control. Sensor, support circuitry, RF power and communications are all deposited on a micro-chip die allowing the circuit to be built in large quantities and at very low cost. This scheme is preferably used for both passive and active devices.

The operational process can consist of two modes, manual or automated. In the manual mode, an operator such as a nurse activates the system and RF energy radiated to the microcircuit in the patch 72 would be stored and converted for use in the temperature measurement process and in the transmission of the data from the end of the BTT to the antenna 78. Once sufficient energy has been transferred (less than 1 second) the microcircuit would make the measurement and transmit the data to the antenna 78 receiver and controller 84 to be displayed for example on a back-lit LCD display at the nursing station. An audio "beep" will signal that the data had been received and is ready for view. In the automated mode, the process is done automatically and continuously by interrogation at preset frequency and an alarm being activated when the reading is outside the specified range. A tri-dimensional antenna can also be used and the controller 84 set up to search the three dimensions of the antenna to assure continued and proper connection between antenna 78 and sensing means 74. It is also understood that the sensor can modulate reflected RF energy. Accordingly, the energy will trigger the unit to acquire a temperature measurement, and then the unit will modulate the reflected energy. This reflected energy and information will be received at the interrogator and displayed as above.

The present invention also provides a method for monitoring biological parameters, which comprises the steps of: securing a passive sensor to the body; generating electromagnetic radiation from a device secured to at least one of a mattress, a pillow and the frame of a bed; generating a signal from said passive sensor; receiving said signal by a device secured to at least one of a mattress, a pillow and the frame of a bed; and determining the value of the biological parameter based on said signal.

It is understood that a variety of external power sources such as electromagnetic coupling can be used including an ultra-capacitor charged externally through electromagnetic induction coupling and cells that can be recharged by an external oscillator. It is also understood that the sensing system can be remotely driven by ultrasonic waves.

Figure 11:
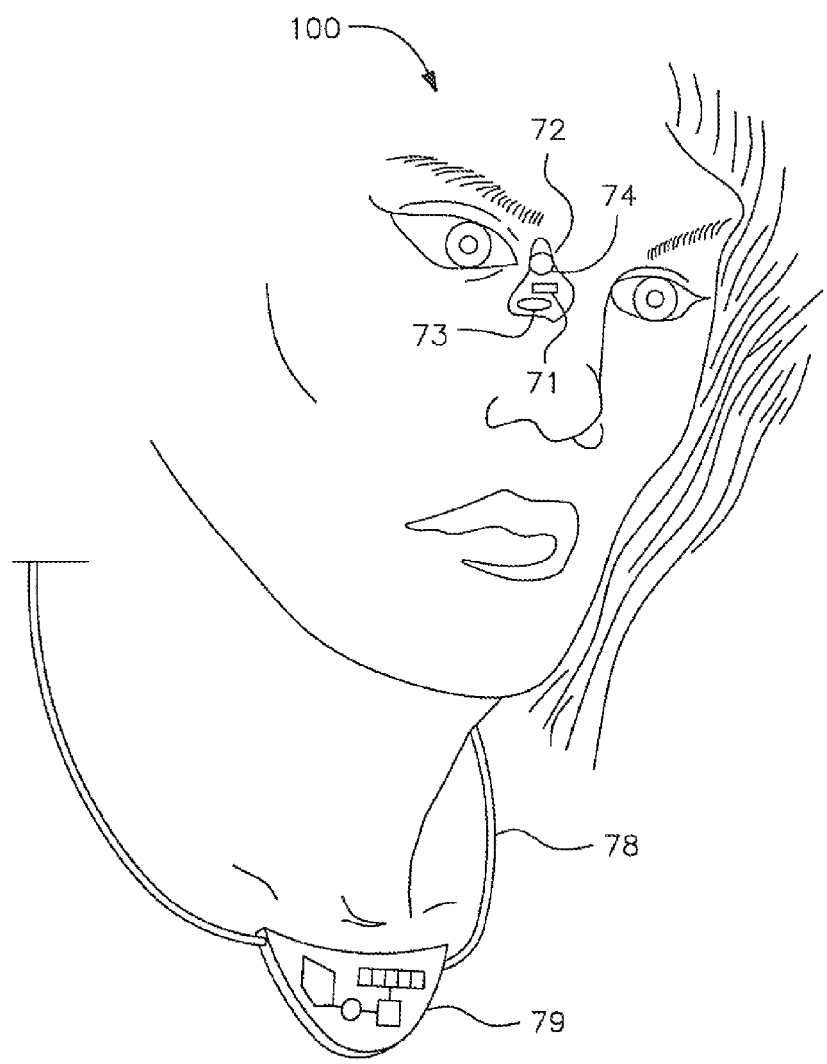
FIG. 11 is a perspective view of another preferred embodiment showing a person wearing a support structure comprised of a patch with a passive sensor positioned on the skin at the end of the tunnel in accordance with the present invention.

FIG. 11 is a perspective view of another preferred embodiment showing in closer detail a person 100 wearing a support structure comprised of patch 72 with a sensor 74, transmitter 71, and digital converter and control 73 positioned on the skin at the end of the tunnel. Person 100 is wearing a necklace which works as antenna 78 and a pendant in the necklace works as the controller unit and transmitting unit 79. Solar cells and/or specialized batteries power unit 79. Patients are used to carrying Holter monitoring and cards with cords around their necks and this embodiment can fit well with those currently used systems. It is understood that, besides a necklace, a variety of articles including clothing and electric devices can be used as a receiver/interrogator and this capability can be easily incorporated into cell phones, note book computers, hand held computers, internet appliances for connecting to the internet, and the like, so a patient could use his/her cell phone or computer means to monitor his/her brain temperature.

The preferred embodiments shown in FIGS. 10 and 11 can preferably provide continuous monitoring of fever or temperature spikes for any surgery, for any patient admitted to a hospital, for nursing home patients, in ambulances, and to prevent death or harm by hospital infection. Hospital infection is an infection acquired during a hospital stay. Hospital infection is the fourth cause of death in the US and kills more than 100,000 patients annually and occurs primarily due to lack of early identification of fever or temperature spikes. The present invention provides timely identification and therapy of an infection due to 24 hour automated monitoring of temperature. If there is a spike in temperature an alarm can be activated. This will allow timely identification and treatment of an infection and thus prevent death or costly complications such as septic shock that can occur due to delay in treating infectious processes. Besides, said preferred embodiments provide means for continuous fever monitoring at home including during sleeping for both children and adults.

Figure 12A:
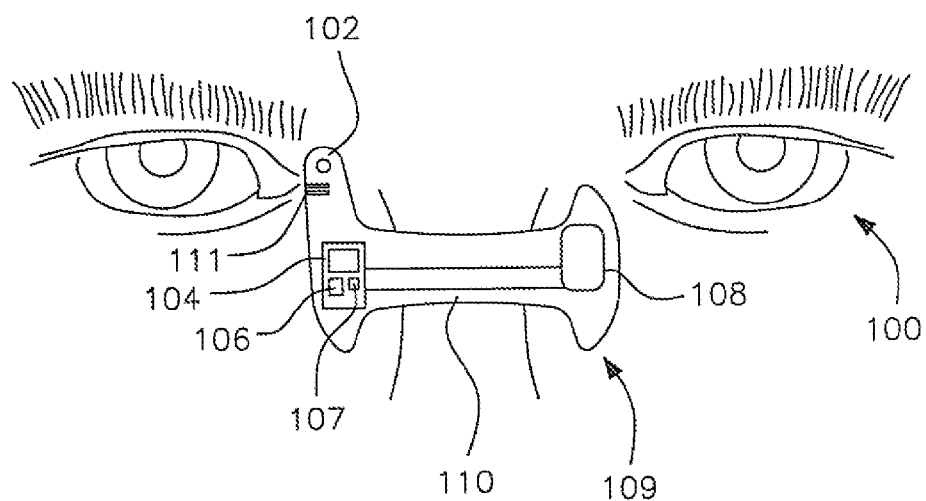
FIG. 12A is a front perspective view of a person wearing a support structure comprised of a patch with an active sensor positioned on the skin at the end of the tunnel in accordance with the present invention.
Figure 12B:
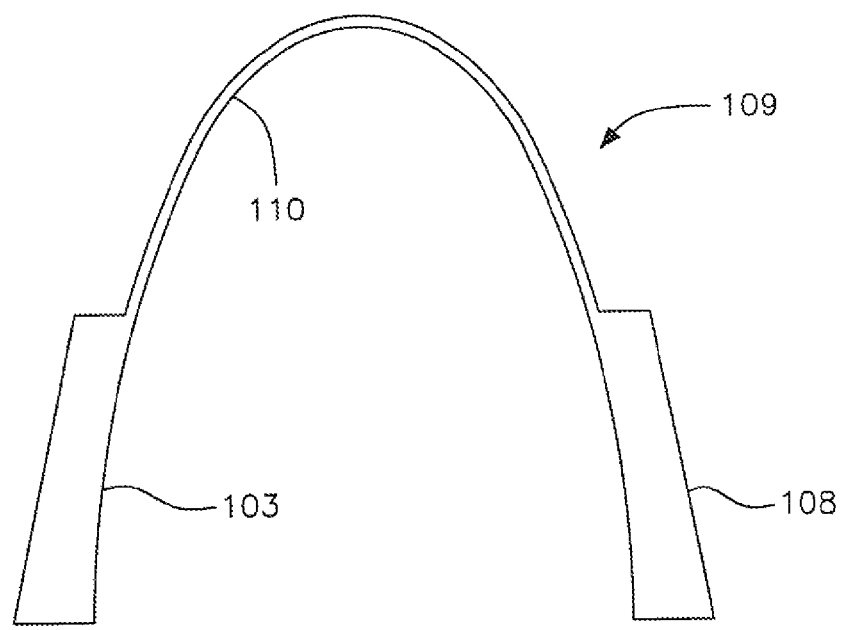
FIG. 12B is a side schematic view showing the flexible nature of the support structure shown in FIG. 12A.

FIG. 12A is a front perspective view of a preferred embodiment showing a person 100 wearing a support structure comprised of a patch 109 with indicator lines 111 and containing an active sensor 102 positioned on the skin at the end of the tunnel. The preferred embodiment shown in FIG. 12 provides transmitting means 104, processing means 106, AD converter 107 and sensing means 102 connected by flexible circuit 110 to power source 108. For example the transmitting module can include RF, sound or light. FIG. 12B is a side schematic view showing the flexible nature of the support structure in FIG. 12A with flexible circuit 110 connecting microelectronic package 103 which contains transmitting means, processing means and sensing means in the right side of the patch 109 to the power source 108 in the left side of said patch 109. Exemplary embodiments will be described.

In accordance with this exemplary embodiment for temperature measurement, the thermal energy emitted by the BTT is sensed by the temperature sensor 102 such as a miniature thermistor which produces a signal representing the thermal energy sensed. The signal is then converted to digital information and processed by processor 106 using standard processing for determining the temperature. An exemplary sonic-based system for brain temperature measurement comprises a temperature sensor, input coupling circuit, signal processing circuit, output coupling circuit and output display circuit. A temperature sensor 102 (e.g., thermistor) in a patch 109 placed on the surface of the skin at the medial canthal area responds to variations in brain temperature which is manifested as a DC voltage signal.

This signal, coupled to a Signal Processor Circuit via an Input Coupling Circuit is used to modulate the output of an oscillator, e.g., a multivibrator circuit, piezoelectric systems operating in or just above the audio frequency range. The oscillator is a primary component of the Signal Processor Circuit. The output of the oscillator is input to an amplifier, which is the second primary component of the Signal Processor.

The amplifier increases the output level from the oscillator so that the output of the Signal Processor is sufficient to drive an Output Display Circuit. Depending on the nature of the Output Display Circuit, e.g., an audio speaker, a visual LED display, or other possible display embodiment, an Output Coupling Circuit is utilized to match the signal from the Signal Processor Circuit to the Output Display Circuit. For an Output Display Circuit that requires a digital input signal the Output Coupling Circuit might include an analog to digital (A/D) converter circuit. A DC power supply circuit is the remaining primary component in the Signal Processor Module. The DC power supply is required to support the operation of the oscillator and the amplifier in the Signal Processing Circuit. Embodiments of the DC power supply can include ultra miniature DC batteries, a light sensitive DC power source, or some combination of the two. The micro transducers, signal processing electronics, transmitters and power source can be preferably constructed as an Application Specific Integrated Circuit or as a hybrid circuit alone or in combination with MEMS (micro electrical mechanical systems) technology.

The thermistor voltage is input to a microcontroller unit, i.e., a single chip microprocessor, which is pre-programmed to process the thermistor voltage into a digital signal which corresponds to the patient's measured temperature in degrees C. (or degrees F.) at the BTT site. It is understood that different programming and schemes can be used. For example, the sensor voltage can be directly fed into to the microcontroller for conversion to a temperature value and then displayed on a screen as a temperature value, e.g., 98.6° F. On the other hand the voltage can be processed through an analog to digital converter (ADC) before it is input to the microcontroller.

The microcontroller output, after additional signal conditioning, serves as the driver for a piezoelectric audio frequency (ultrasonic) transmitter. The piezoelectric transmitter wirelessly sends digital pulses that can be recognized by software in a clock radio sized receiver module consisting of a microphone, low-pass audio filter, amplifier, microcontroller unit, local temperature display and pre-selected temperature level alert mechanism. The signal processing software is pre-programmed into the microcontroller unit of the receiver. Although the present invention provides means for RF transmission in the presence of noise, this particular embodiment using a microphone as the receiving unit may offer additional advantages in the hospital setting since there is zero RF interference with the many other RF devices usually present in said setting. The microcontroller unit drives a temperature display for each patient being monitored. Each transmitter is tagged with its own ID. Thus one receiver module can be used for various patients. A watch, cell phone, and the like adapted with a microphone can also work as the receiver module.

In another embodiment the output of the microcontroller is used to drive a piezo-electric buzzer. The microcontroller output drives the piezo-electric buzzer to alert the user of the health threatening situation. In this design the output of the microcontroller may be fed into a digital-to-analog converter (DAC) that transforms the digital data signal from the microcontroller to an equivalent analog signal which is used to drive the buzzer.

In yet another embodiment the output from the (DAC) is used to drive a speech synthesizer chip programmed to output an appropriate audio warning to the user, for instance an athlete at risk of heatstroke. For a sensed temperature above 39 degrees Celsius the message might be: "Your Body temperature is High. Seek shade. Drink cold liquid. Rest." For temperature below 36 degrees Celsius the message might be: "Your Body temperature is Low. Seek shelter from the Cold. Drink warm liquid. Warm up."

In another embodiment the output is used to drive a light transmitter programmed to output an appropriate light signal. The transmitter consists of an infrared light that is activated when the temperature reaches a certain level. The light signal will work as a remote control unit that activates a remote unit that sounds an alarm. This embodiment for instance can alert the parents during the night when the child is sleeping and has a temperature spike.

An exemplary embodiment of the platform for local reporting consists of three electronic modules mechanically housed in a fabric or plastic holder such as patch 100, which contain a sensor 102 positioned on the skin at the BTT site. The modules are: Temperature Sensor Module, Microcontroller Module, and Output Display Module in addition to a battery. An electronic interface is used between each module for the overall device to properly function. The configuration of this system consists of a strip such as patch 100 attached to the BTT area by a self-adhesive pad. A thermistor coupled to a microcontroller drives an audio frequency piezoelectric transmitter or LED. The system provides local reporting of temperature without a receiver. An audio tone or light will alert the user when certain thresholds are met. The tone can work as a chime or reproduction of human voice.

Another exemplary embodiment for remote reporting consists of four electronic modules: Sensor Module, Microcontroller Module, Output Transmitter Module and Receiver/Monitor Module. From a mechanical viewpoint the first three modules are virtually identical to the first embodiment. Electronically the Temperature Sensor and Microprocessor Modules are identical to the previous embodiment. In this embodiment an Output Transmitter Module replaces the previous local Output Display Module. Output Transmitter Module is designed to transmit wirelessly the temperature results determined by the Microprocessor Module to a remotely located Receiver/Monitor Module. An electronic interface is used between each module for proper function. This device can be utilized by patients in a hospital or home setting. On a continuous basis temperature levels can be obtained by accessing data provided by the Receiver/Monitor Module.

A variety of temperature sensing elements can be used as a temperature sensor including a thermistor, thermocouple, or RTD (Resistance Temperature Detector), platinum wire, surface mounted sensors, semiconductors, thermoelectric systems which measure surface temperature, optic fiber which fluoresces, bimetallic devices, liquid expansion devices, and change-of-state devices, heat flux sensor, crystal thermometry and reversible temperature indicators including liquid crystal Mylar sheets. Two preferred temperature sensors are thermistor models ET-503 and 104JT available from Semitec of Japan.

FIG. 13 shows a block diagram of a preferred embodiment of the present invention linking transmitter 120 to receiver 130. Transmitter 120 preferably includes a chip 112 incorporating a microcontroller (MCU) 114, a radio frequency transmitter (RF) 116 and a A/D converter 118 in addition to a power source 122, amplifier (A) 124, sensor 126, and antenna 128, preferably built-in in the chip. Exemplary chips include: (1) rfPIC12F675F, (available from Microchip Corporation, Arizona, USA) this is a MCU+ADC+433 Mhz Transmitter (2) CC1010, available from Chipcon Corporation of Norway.

Receiver 130 preferably includes a chip RF transceiver 132 (e.g., CC1000 available from Chipcon Corporation), a microcontroller unit (MCU) 134, amplifier and filtering units (A/F) 136, display 138, clock 140, keypad 142, LED 144, speaker 146, in addition to a power source 150 and input/output units (I/O) 148 and associated modem 152, optical transceiver 154 and communication ports 156.

A variety of means can be used for the transmission scheme besides the commercially available RF transmitter chips previously mentioned. One simple transmission means include an apparatus with a single channel transmitter in the 916.48 MHz band that sends the temperature readings to a bed side receiver as a frequency proportional to the reading. The thermistor's resistance would control the frequency of an oscillator feeding the RF transmitter data input. If the duty cycle is less than 1%, the 318 MHz band would be usable. Rather than frequency, a period measurement technique can be used. The model uses a simple radio frequency carrier as the information transport and modulating that carrier with the brain temperature information derived from a transduction device capable of changing its electrical characteristics as a function of temperature (e.g.; thermistor). Either frequency or amplitude of the carrier would be modulated by the temperature information so that a receiver tuned to that frequency could demodulate the changing carrier and recover the slowly moving temperature data.

Another transmission technique suitable to transmit the signal from a sensor in a support structure is a chirp device. This means that when activated, the transmitter outputs a carrier that starts at a lower frequency in the ISM band and smoothly increases frequency with time until a maximum frequency is reached. The brain temperature information is used to modify the rate of change of frequency of the chirp. The receiver is designed to measure the chirp input very accurately by looking for two or more specific frequencies. When the first of the frequencies is detected, a clock measures the elapsed time until the second frequency is received. Accordingly, a third, fourth, etc., frequency could be added to aid in the rejection of noise. Since virtually all the direct sequence spread spectrum transmitters and frequency hopping transmitters are spread randomly throughout their part of the ISM band, the probability of them actually producing the "right" sequence of frequencies at exactly the right time is remote.

Once the receiver measured the timing between the target frequencies, that time is the value that would represent the brain temperature. If the expected second, third, or fourth frequency is not received by the receiver within a "known" time window, the receiver rejects the initial inputs as noise. This provides a spread spectrum system by using a wide spectrum for transmitting the information while encoding the information in a way that is unlike the expected noise from other users of the ISM band. The chirp transmitter is low cost and simple to build and the brain temperature transducer is one of the active elements that controls the rate of change of frequency.

Other preferred embodiments for local reporting include a sensor, an operational amplifier (LM358 available from National Semiconductor Corporation) and a LED in addition to a power source. It is understood that the operational amplifier (Op Amp) can be substituted by a MCU and the LED substituted by a piezoelectric component.

Figure 14:
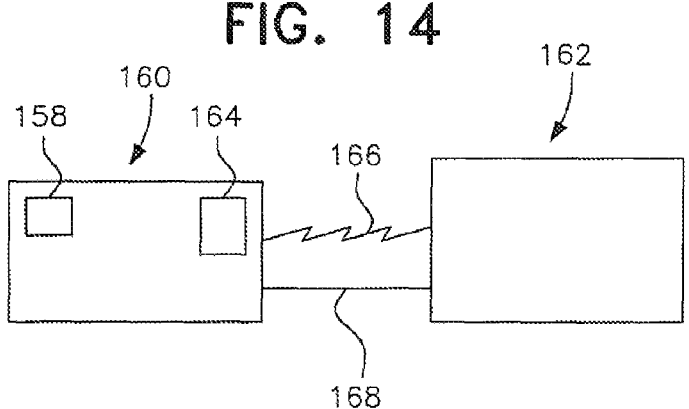
FIG. 14 is a schematic diagram of one preferred embodiment of the invention interacting with devices and articles of manufacture.

FIG. 14 is a schematic diagram showing the support structure 160 with a sensor 158, and MCU 164 controlling and/or adjusting unit 162. Communication between MCU 164 and unit 162 is achieved by wires 168 or wirelessly 166. By way of example, but not by limitation, exemplary units 162 include climate control units in cars, thermostats, vehicle seats, furniture, exercise machines, clothing, footwear, medical devices, drug pumps, and the like. For example, MCU 164 is programmed with transmit the temperature level to receiver unit 162 in the exercise machine. MCU in the exercising machine unit 162 is programmed to adjust speed or other settings in accordance with the signal generated by MCU 164.

The preferred embodiment allows precise positioning of the sensing apparatus by the support structure on the BTT site. The support structure is designed to conform to the anatomical landmarks of the BTT area which assures proper placement of the sensor at all times. The corner of the eye is considered a permanent anatomic landmark, i.e., it is present in the same location in all human beings. The BTT area is also a permanent anatomic landmark as demonstrated by the present invention. To facilitate consistent placement at the BTT site, an indicator in the support structure can be used as shown in FIGS. 15A to 15E.

Figure 15A:
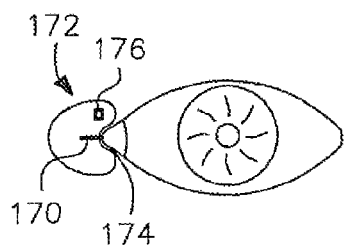
FIGS. 15A to 15E are schematic views showing preferred embodiments of the invention using indicators.

FIG. 15A shows a Guiding Line 170 placed on the outside surface of the support structure 172. The Guiding Line 170 is lined up with the medial corner of the eye 174. The sensor 176 is located above the Guiding Line 170 and on the outer edge of the support structure 172, so once the Guiding Line 170 of the support structure 172 is lined up with the medial corner of the eye 174, the sensor 176 is positioned on the main entry point of the tunnel. Thus the support structure 172 can be precisely and consistently applied in a way to allow the sensor 176 to cover the BTT area at all times.

Figure 15B:
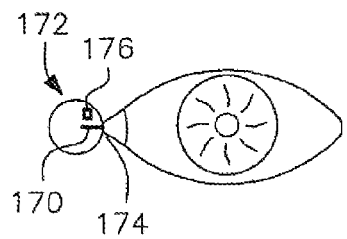

FIG. 15B shows a different design of the patch 172 but with the same Guiding Line 170 lined up with the medial corner of the eye 174, thus allowing consistent placement of sensor 176 at the BTT site despite the difference in design.

Figure 15C:
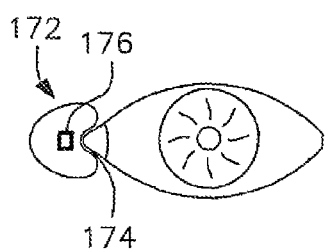

FIG. 15C is another preferred embodiment showing the sensor 176 lined up with medial corner 174. Thus in this embodiment a Guiding Line is not required and the sensor 176 itself guides the positioning.

Figure 15D:
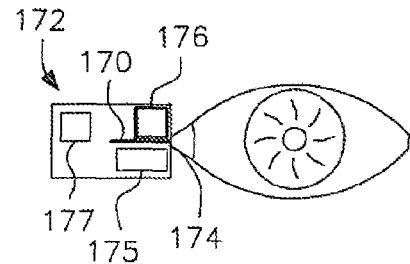

In FIG. 15D the MCU 175 and cell 177 of patch 172 are located outside of the BTT site while sensor 176 is precisely positioned at the BTT site. It is understood that any type of indicator on the support structure can be used to allow proper placement in the BTT area including external marks, leaflets, cuts in the support structure, different geometry that lines up with the corner of the eye, and the like.

Figure 15E:
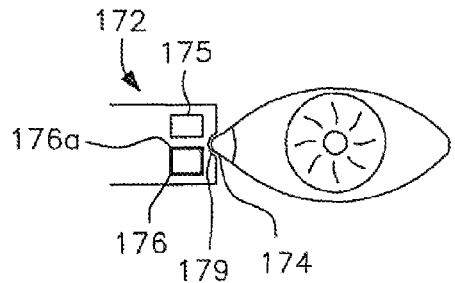

FIG. 15E is another preferred embodiment showing the superior edge 176a of sensor 176 lined up with medial corner 174 and located in the inferior aspect of the medial canthal area while microchip controller 175 is located in the superior aspect of the medial canthal area. Support structure 172 has a geometric indicator 179 comprised of a small recess on the support structure 172. It is understood that a strip working as support structure like a band-aid can have the side opposite to the sensor and hardware made with tear off pieces. The sensor side is first attached to the skin and any excess strip can be easily torn off. Two sizes, adult and children cover all potential users.

The material for the support structure working as a patch can be soft and have insulating properties such as are found in polyethylene. Depending on the application a multilayer structure of the patch can include from the external side to the skin side the following: thinsulate layer; double foam adhesive (polyethylene); sensor (thermistor); and a Mylar sheet. The sensor surface can be covered by the Mylar sheet, which in turn is surrounded by the adhesive side of the foam. Any soft thin material with high thermal resistance and low thermal conductivity can be preferably used as an interface between the sensor and the exterior, such as polyurethane foam (K=0.02 W/m·C). Any support structure can incorporate the preferred insulation material.

A preferred power source for the patch includes natural thermoelectrics as disclosed by the present invention. In addition, standard lightweight thin plastic batteries using a combination of plastics such as fluorophenylthiophenes as electrodes can be used, and are flexible allowing better conformation with the anatomy of the BTT site. Another exemplary suitable power source includes a light weight ultra-thin solid state lithium battery comprised of a semisolid plastic electrolyte which are about 300 microns thick.

The system can have two modes: at room temperature the system is quiet and at body temperature the system is activated. The system can also have an on/off switch by creating a circuit using skin resistance, so only when the sensor is placed on the skin is the system activated. The patch can also have a built-in switch in which peeling off a conductive backing opens the circuit (pads) and turn the system on. In addition, when removed from the body, the patch can be placed in a case containing a magnet. The magnet in the case acts as an off switch and transmission is terminated when said patch is in the case.

Figure 16A:
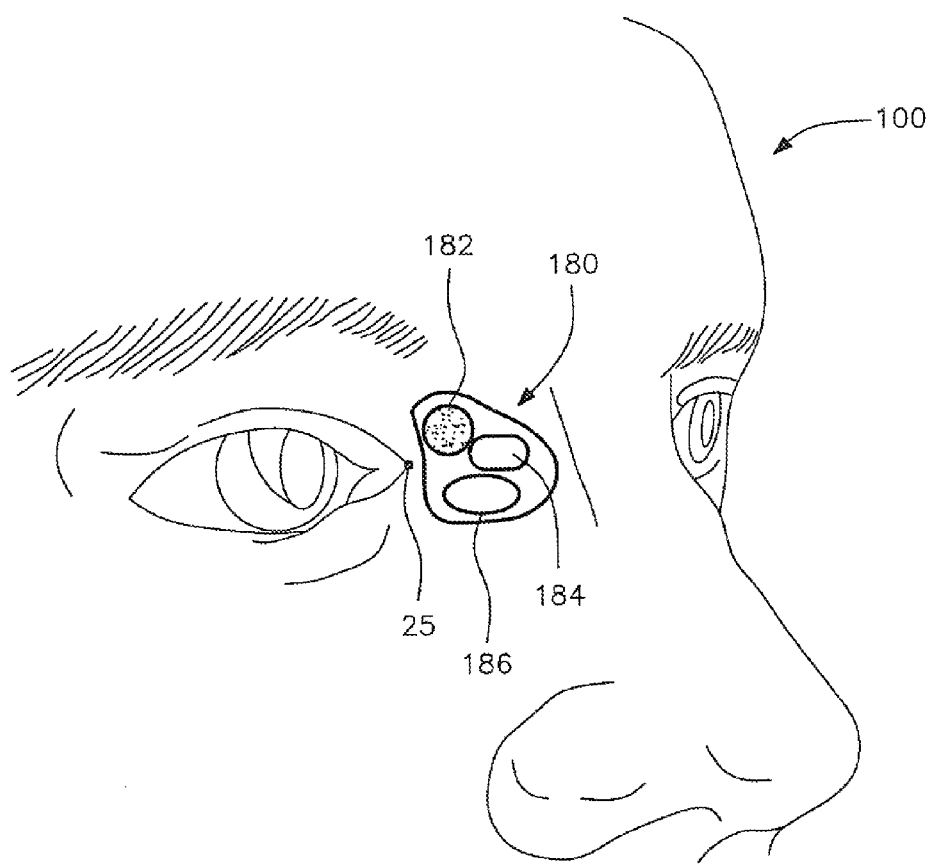
FIGS. 16A to 16C are perspective views of a preferred embodiment showing a person wearing support structures incorporated as patches.
Figure 16B:
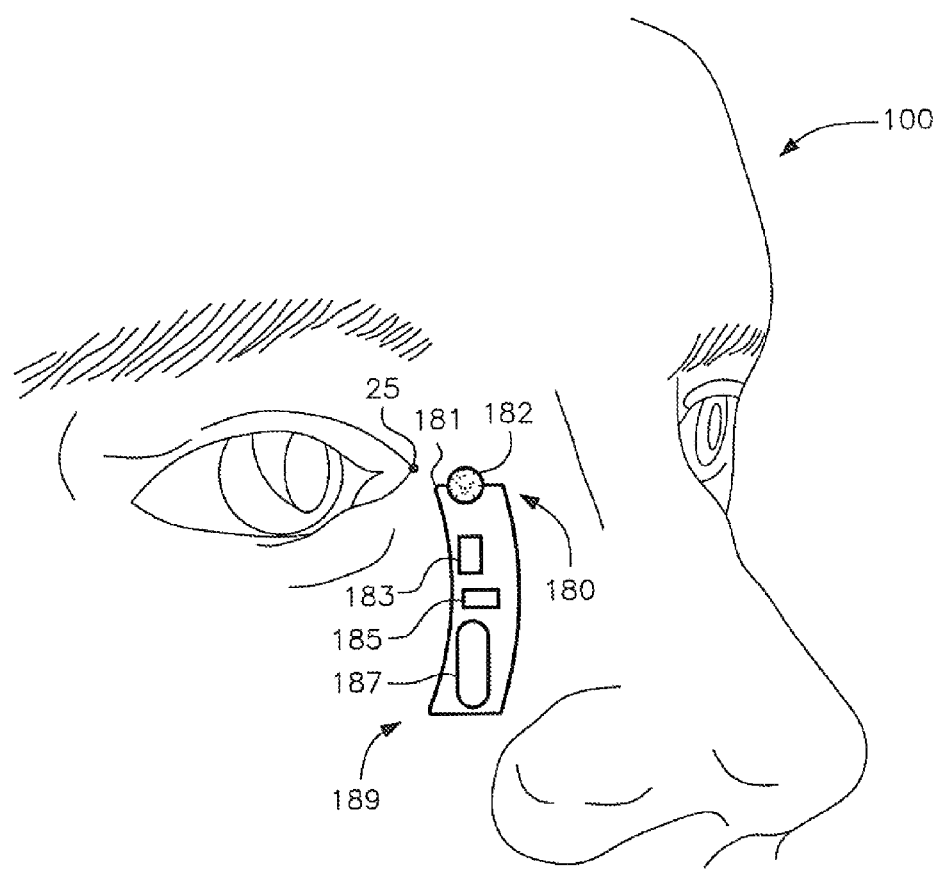
Figure 16C:
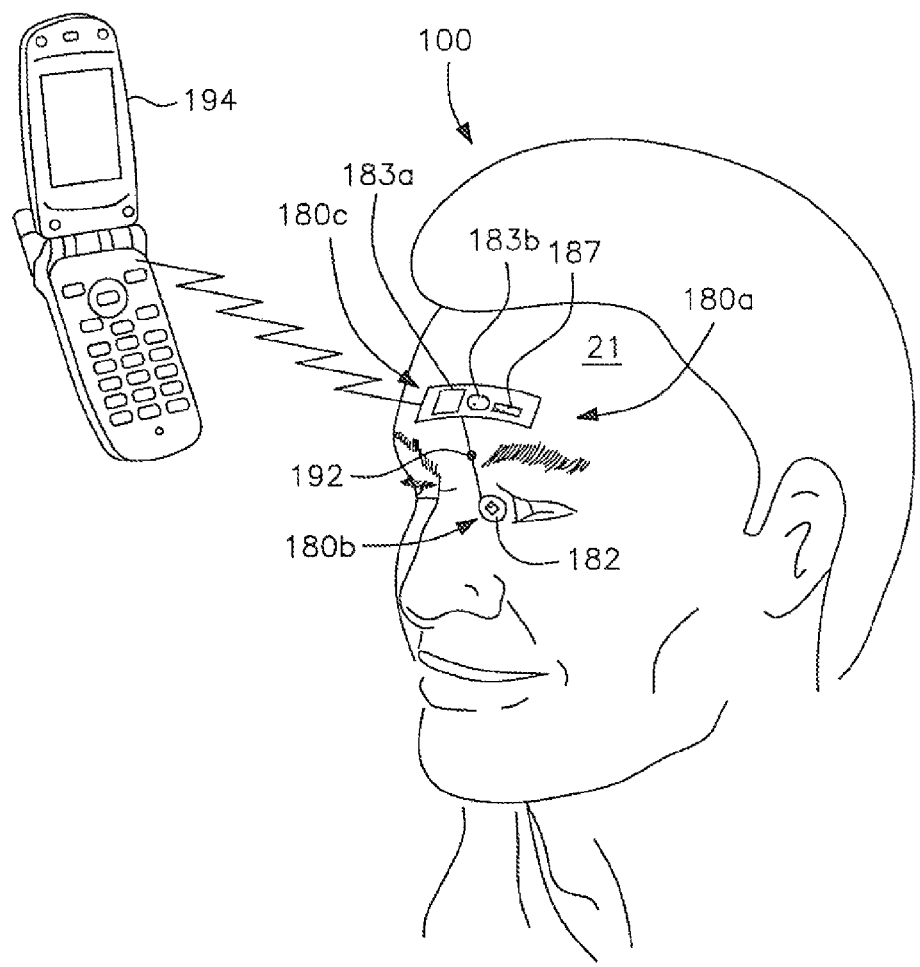

FIG. 16A to 16C are perspective views of preferred embodiments showing a person 100 wearing support structures 180 incorporated as patches. In a preferred embodiment shown in FIG. 16A, the support structure 180 contains LED 184, cell 186, and sensor 182. Sensor 182 is positioned at a main entry point on the superior aspect of the medial canthal area adjacent to the medial corner of the eye 25. LED 184 is activated when signal reaches certain thresholds and in accordance with the principles of the invention. FIG. 16B is another preferred embodiment showing a person 100 wearing support structure 180 with sensor 182 positioned at the general area of the main entry point of the tunnel with the superior edge 181 of support structure 180 being lined up with the corner of the eye 25. Support structure 180 contains an extension that rests on the cheek area 189 and houses transmitting means 183 for wireless transmission, processing means 185 and power source 187. FIG. 16C is an exemplary preferred embodiment showing person 100 wearing a two piece structure 180a comprised of support structure 180b and housing structure 180c connected by wires 192, preferably a flexible circuit. Support structure 180b contains the sensor 182 which is positioned at the BTT site. Housing structure 180c which can comprise an adhesive strip on the forehead 21 houses processing means 183a, transmitting means 183b and power source 187 for transmitting the signal to unit 194, for example a cell phone.

Figure 17:
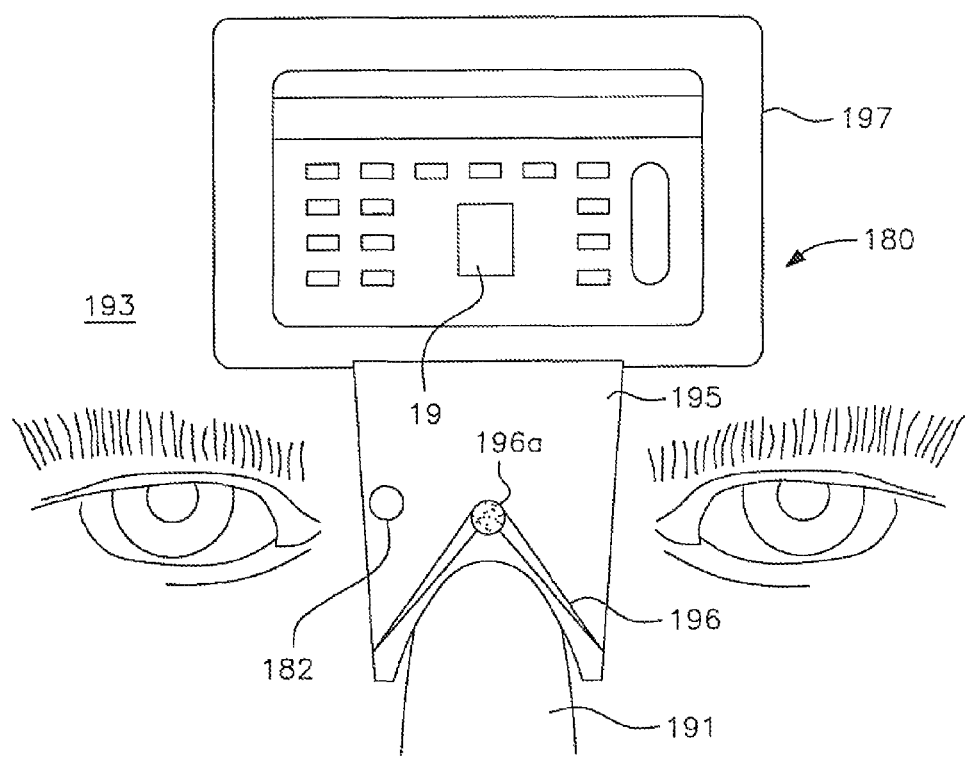
FIG. 17 is a perspective view of another preferred embodiment showing a person wearing a support structure incorporated as a clip with a sensor positioned on the skin at the end of the tunnel in accordance with the present invention.

FIG. 17 is a schematic view of another preferred embodiment showing the support structure 180 with sensor 182 being held at the nose 191 by a clip 196. Support structure 180 extends superiorly to the forehead 193. Housing 195 of support structure 180 contains pressure attachment means such as clip 196. Housing 197 on the forehead contains the transmitting means and power source. Clip 196 uses a spring based structure 196a to apply gentle pressure to secure support structure 180 and sensor 182 in a stable position. Housing 197 can also have a LCD display 19. The LCD 19 can have an inverted image to be viewed in a mirror by the user, besides LCD 19 can have a hinge or be foldable to allow proper positioning to allow the user to easily view the numerical value displayed.

FIG. 18 is a perspective view of another preferred embodiment showing a person 100 wearing a support structure 180 comprised of a patch with sensor 182 positioned on the skin at the end of the tunnel and connected by a wire 199 to a decoding and display unit 200. Support structure 180 has a visible indicator 170 lined up with the medial corner of the eye 174. Wire 199 includes an adhesive tape 201 within its first 20 cm, and most preferably adhesive tape connected to wire 199 is in the first 10 cm of wire from sensor 182.

FIGS. 19A1 to 19D are schematic views of preferred geometry and dimensions of support structures 180 and sensing means 182. Special geometry and dimension of sensors and support structure is necessary for the optimal functioning of the present invention. The dimensions and design for the support structure 180 are made in order to optimize function and in accordance with the geometry and dimensions of the different parts of the tunnel.

FIG. 19A1 shows support structure 180 working as a patch. The patch 180 contains sensor 182. The patch 180 may contain other hardware or solely the sensor 182. Exemplary sensor 182 is a flat thermistor or surface mount thermistor. The preferred longest dimension for the patch referred to as "z" is equal or less than 12 mm, preferably equal or less than 8 mm, and most preferably equal or less than 5 mm. The shortest distance from the outer edge of the sensor 182 to the outer edge of the patch 180 is referred to as "x". "x" is equal or less than 11 mm, preferably equal or less than 6 mm and most preferably equal or less than 2.5 mm. For illustrative purposes the sensor 182 has unequal sides, and distance "y" corresponds to the longest distance from outer edge of the sensor to outer edge of the patch 180. Despite having unequal sides, the shortest distance "x" is the determining factor for the preferred embodiment. It is understood that the whole surface of the sensor 182 can be covered with an adhesive and thus there is no distance between the sensor and an outer edge of a support structure.

An exemplary embodiment for that includes a sensor in which the surface touching the skin at the BTT site is made with Mylar. The Mylar surface, which comprises the sensor itself, can have an adhesive in the surface that touches the skin.

As shown in FIG. 19A2, the sensor 182 has adhesive in its surface, to be secured to skin 11. The sensor then can be applied to the BTT site in accordance with the principles of the invention. The preferred distance "x" equal or less than 2.5 mm allows precise pinpoint placement of sensor 182 at the main entry site of the tunnel and thus allows the most optimal signal acquisition, and it should be used for applications that require greatest precision of measurements such as during monitoring surgical procedures. Although a patch was used as support structure for the description of the preferred dimensions, it is understood that the same dimensions can be applied to any support structure in accordance with the principle of the invention including clips, medial canthal pads, head mounted gear, and the like.

FIG. 19B is an exemplary embodiment of a round patch 180 with a flat sensor 182. Preferred dimensions "x" and "z" apply equally as for FIG. 19A1. FIG. 19C is an exemplary embodiment of a patch 180 with a bead-type sensor 182. Preferred dimensions "x" and "z" apply equally as for FIG. 19A1. FIG. 19D is an exemplary embodiment of a support structure 180 with a sensor-chip 15. Sensor chip 15 comprises a sensor that is integrated as part of a chip, such as an Application Specific Integrated Circuit (ASIC). For example sensor chip 15 includes sensor 15a, processor 15b, and transmitter 15c. Preferred dimension "x" apply equally as for FIG. 19A1. Other hardware such as power source 27 may be housed in the support structure 180 which can have a long dimension referred to as "d" that does not affect performance as long as the dimension "x" is preserved.

The support structure and sensor are adapted to match the geometry and dimensions of the tunnel, for either contact measurements or non-contact measurements, in which the sensor does not touch the skin at the BTT site.

Figure 20A:
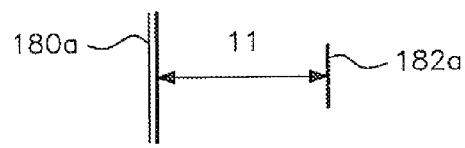
FIGS. 20A to 20C are schematic diagrams of preferred dimensions of the outer edge of support structures in relation to the outer edge of sensing means.
Figure 20B:
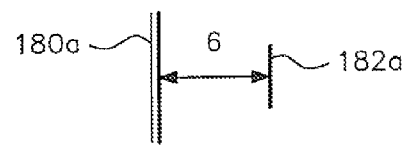
Figure 20C:
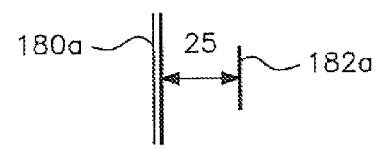

FIGS. 20A to 20C show the preferred dimensions "x" for any support structure in accordance with the present invention. The distance from the outer edge 180a of the support structure to outer edges of sensor 182a is 11 mm, as shown in FIG. 20A. Preferably, the distance from the outer edge 180a of support structure to outer edges of sensor 182a is 6 mm, as shown in FIG. 20B. Most preferably, the distance from the outer edge 180a of the support structure to outer edges of sensor 182a is 2.5 mm, as shown in FIG. 20C.

Figure 21A:
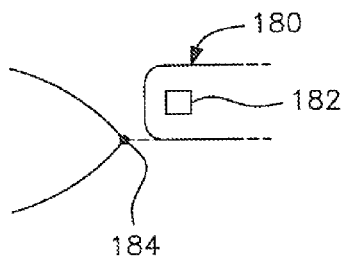
FIGS. 21A and 21B are schematic diagrams of preferred positions of sensing means.
Figure 21B:
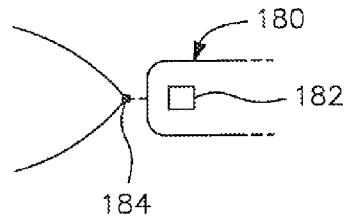

Preferred positions of sensors 182 in relation to the medial corner of the eye 184 are shown in FIGS. 21A and 21B. Support structure 180 positions sensor 182 lined up with medial corner 184 (FIG. 21B). Preferably, as shown in FIG. 21A, support structure 180 positions the sensor 182 above the medial corner 184.

The preferred embodiments of support structures incorporated as patches and clips are preferably used in the hospital setting and in the health care field including continuous monitoring of fever or temperature spikes. Support structures incorporated as medial canthal pads or head mounted gear are preferred for monitoring hyperthermia, hypothermia and hydration status of recreational athletes, professional athletes, military, firefighters, construction workers and other physically intensive occupations, occupational safety, and for preventing wrinkle formation due to thermal damage by sun light.

Figure 22B:
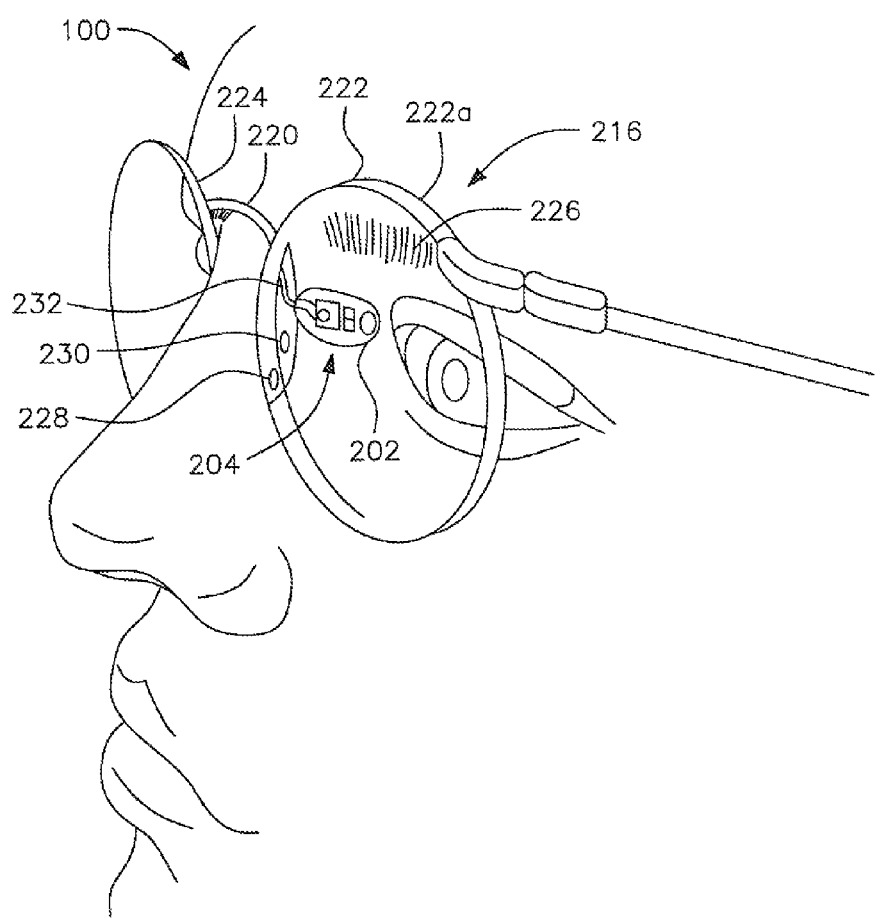
Figure 22C:
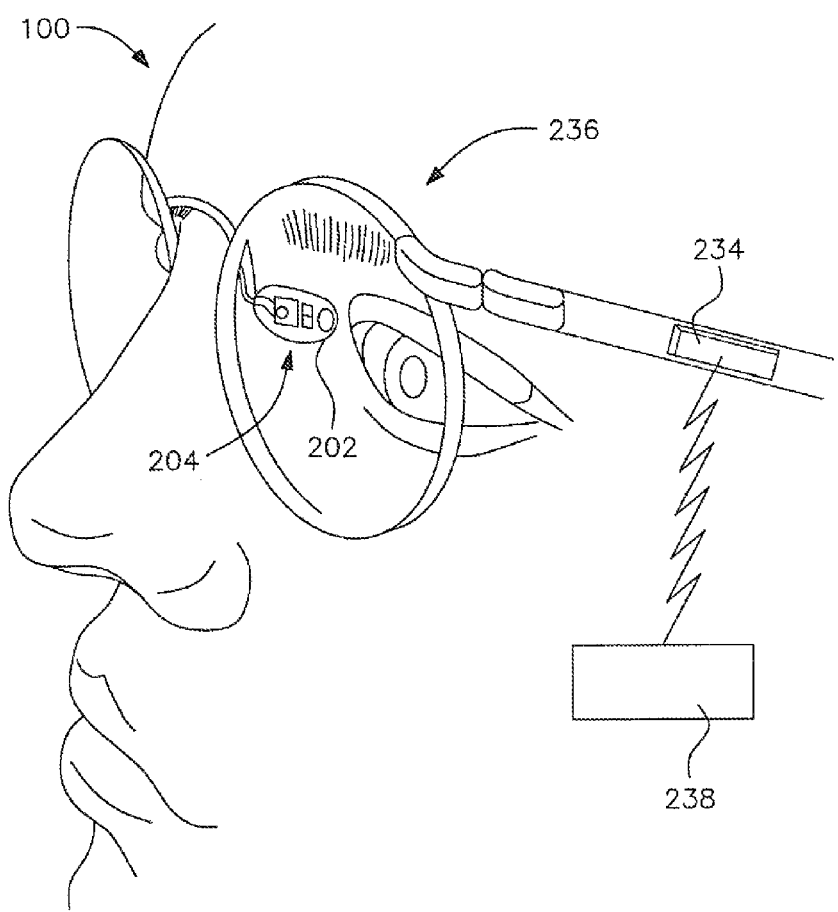

FIGS. 22A to 22C are perspective views of preferred embodiments showing a person 100 wearing support structures incorporated as a medial canthal pad 204 of eyeglasses 206. In a preferred embodiment shown in FIG. 22A, the medial canthal pad 204 contains sensor 202. Connecting arm 208 connects medial canthal pad 204 to eyeglasses frame 206 next to regular nose pads 212. Sensor 202 is positioned on the superior aspect of the medial canthal area adjacent to the medial corner of the eye 210.

FIG. 22B is an exemplary preferred embodiment showing person 100 wearing support structure incorporated as medial canthal pads 204 with sensor 202 integrated into specially constructed eyeglasses frame 216 and containing LEDs 228, 230. Connecting piece 220 which connects the left lens rim 222 and right lens rim 224 is constructed and positioned at a higher position than customary eyeglasses construction in relation to the lens rim 222, 224. Due to the higher position of connecting piece 220 and the special construction of frame 216, the upper edge 222a of left lens rim 222 is positioned slightly above the eyebrow 226. This construction allows medial canthal pad 204 to be positioned at the BTT site while LEDs 228, 230 are lined up with the visual axis. Arm 232 of medial canthal pad 204 can be flexible and adjustable for proper positioning of sensor 202 on the skin at the BTT site and for moving away from the BTT site when measurement is not required. The LED 228 is green and LED 230 is red, and said LEDs 228, 230 are activated when signal reaches certain thresholds.

FIG. 22C is an exemplary preferred embodiment showing person 100 wearing support structure incorporated as medial canthal pads 204 with sensor 202. Signal from sensor 202 is transmitted wirelessly from transmitter 234 housed in the temple of eyeglasses 236. Receiving unit 238 receives a signal from transmitter 234 for processing and displaying. Exemplary receiving units 238 include watch, cell phone, pagers, hand held computers, and the like.

Figure 23B:
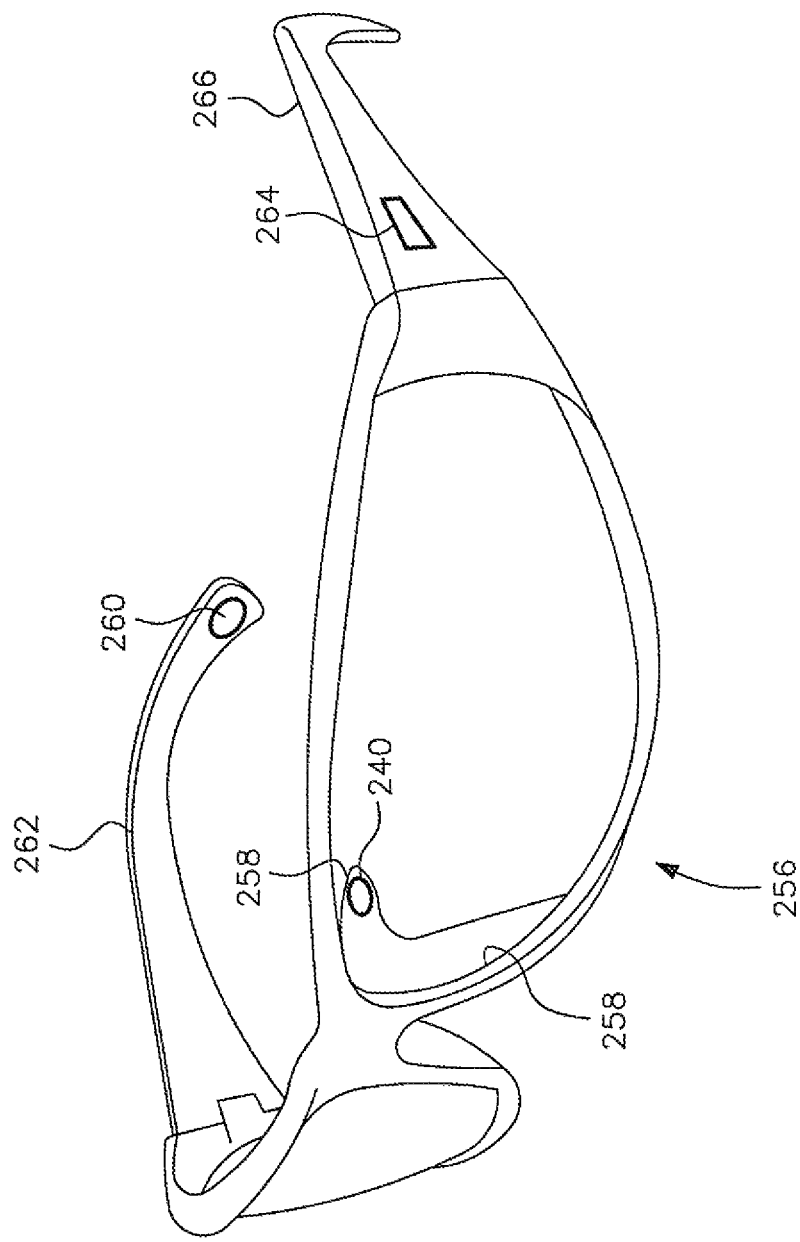

FIGS. 23A to 23B are perspective views of alternative embodiments showing support structures incorporated as a modified nose pad 242 of eyeglasses 244. FIG. 23A is a perspective view showing eyeglasses 244 containing a modified nose pad 242 with sensor 240 and processor 241, sweat sensor 246 and power source 248 supported by temple 250, and transmitter 252 supported by temple 254, all of which are electrically connected. Modified nose pads 242 are comprised of oversized nose pads with a horn like extension 243 superiorly which positions sensor 240 on top of the end of the tunnel.

FIG. 23B is a perspective view showing eyeglasses 256 containing an oversized modified nose pad 258 with sensor 240, sweat sensor 260 supported by temple 262, and transmitter 264 supported by temple 266. Modified oversized nose pad 258 measures preferably 12 mm or more in its superior aspect 258a and contains sensor 240 in its outer edge in accordance with the dimensions and principles of the present invention.

Figure 24:
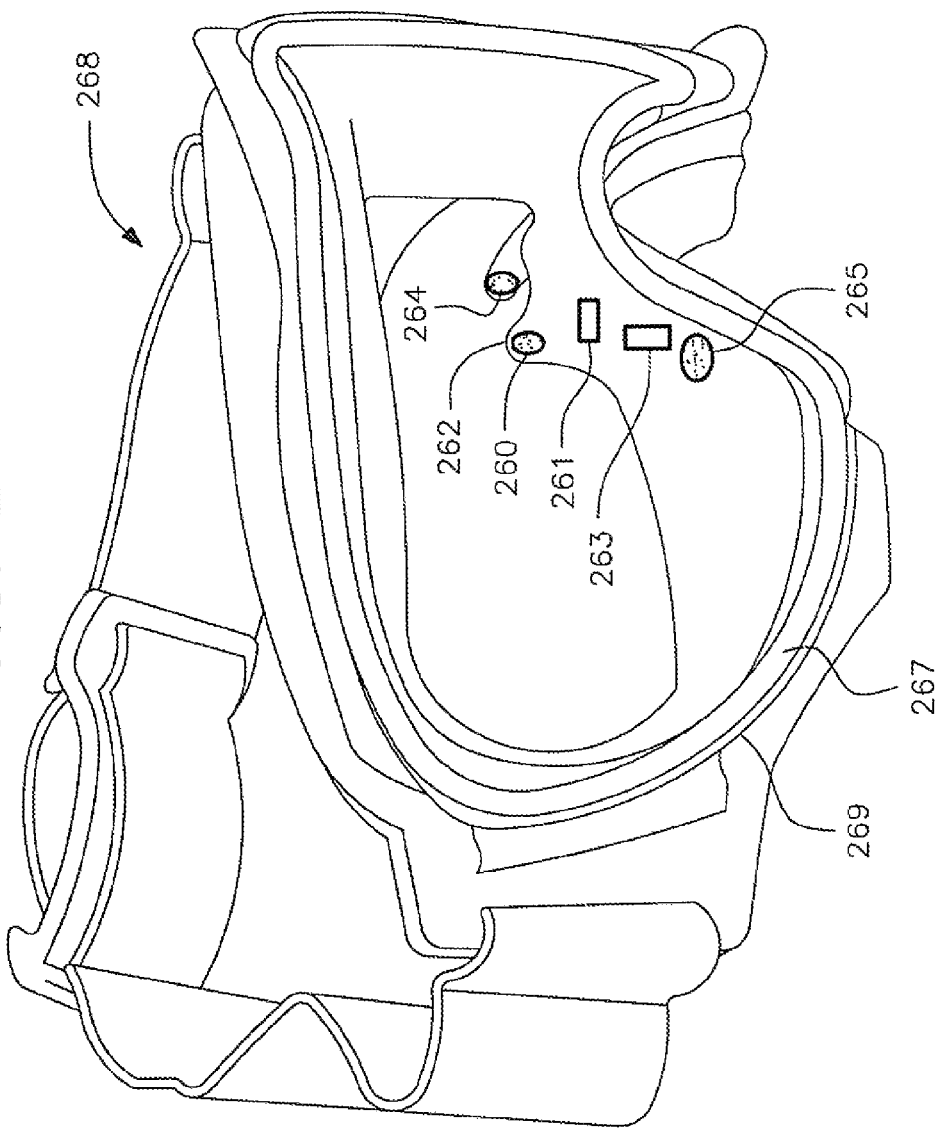
FIG. 24 is a perspective view of another preferred embodiment of support structure in accordance with the invention.

Another preferred embodiment of the invention, shown in FIG. 24, provides goggles 268 supporting medial canthal pads 260 adapted to position sensor 262, 264 at the tunnel site on the skin. As shown, goggles 268 also support transmitting means 261, power source 263, local reporting means 265 such as LED and an antenna 267 for remote reporting. Antenna 267 is preferably integrated as part of the lens rim 269 of goggles 268.

Figure 25:
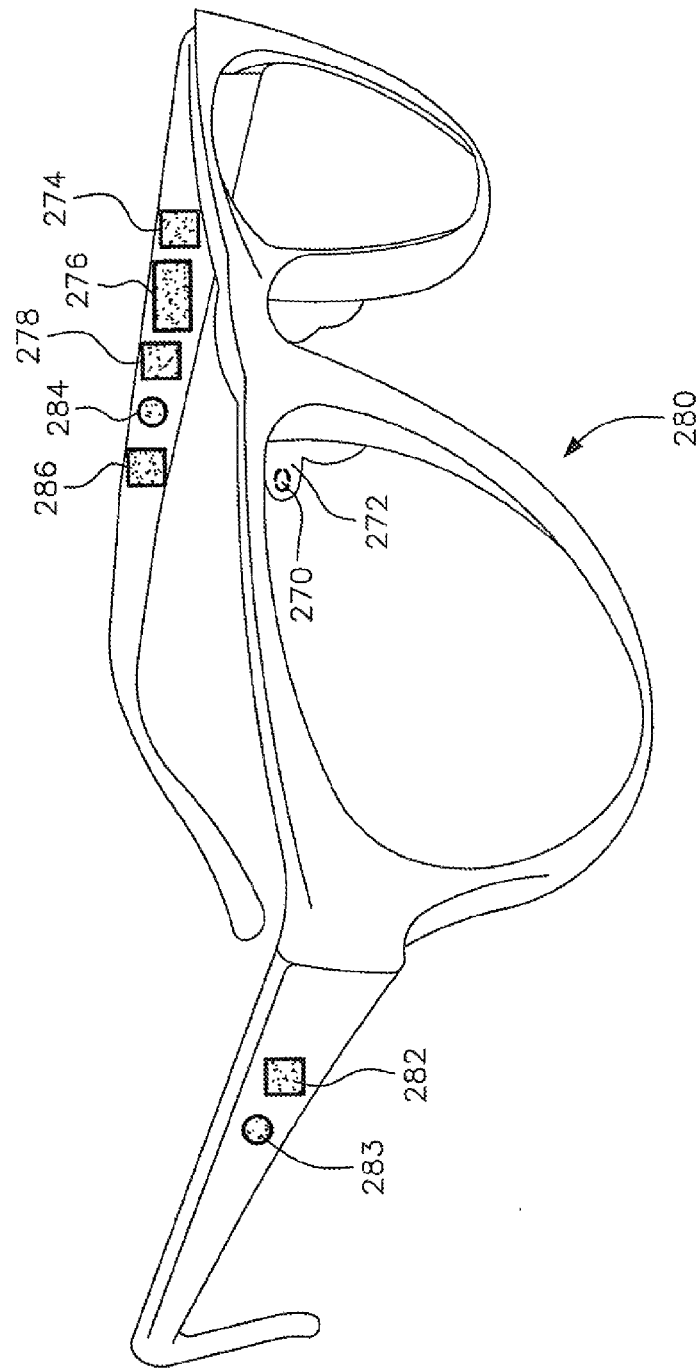
FIG. 25 is a perspective view of one preferred embodiment of support structure showing additional means for including a sensor.

As shown in FIG. 25, additional means related to the signal generated by sensor 270 in medial canthal pad 272 include power switch 274, set switch 276 which denotes a mode selector, transmitter 278 for wireless transmission of signals, a speaker 282, piezoelectric device 283, input means 284 and processing means 286. The means 274, 276, 278, 282, 284, and 286 are preferably supported by any portion of the frame of eyeglasses 280. It is understood that a variety of means, switches and controlling means to allow storage of data, time and other multiple functions switches can be incorporated in the apparatus in addition to wires for wired transmission of signals.

Figure 26A:
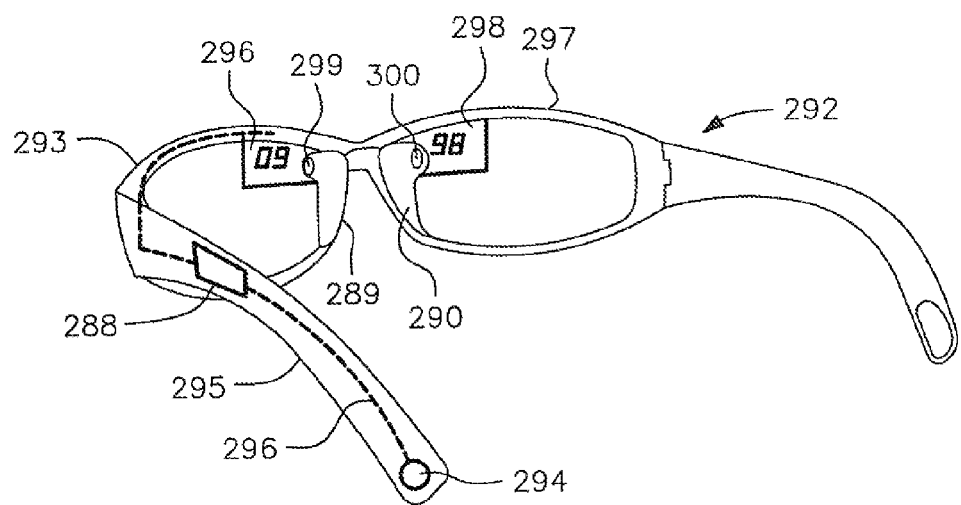
FIG. 26A is a rear perspective view of one preferred embodiment of a support structure with display means.

FIG. 26A is a rear perspective view of one preferred embodiment showing sensors 299, 300 supported by medial canthal pads 290, 289 of eyeglasses 292 and includes lens rim 297 and display 298 in addition to transmitter 288, sweat sensor 294 and wires 296 disposed within temple 295 and lens rim 293 of said eyeglasses 292 and connected to display means 296.

Figure 26B:
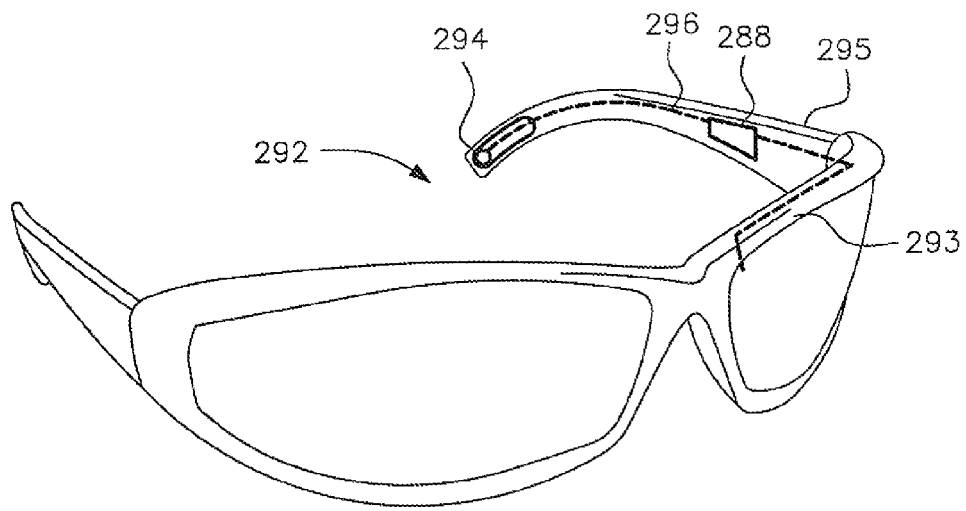
FIG. 26B is a front perspective view of one preferred embodiment of a support structure with display means.

FIG. 26B is a front perspective view of eyeglasses 292 including sweat sensor 294, transmitter 288 and wires 296 disposed within temple 295 and lens rim 293 of eyeglasses 292 and connected to display means. In this embodiment sweat sensor 294 produces a signal indicating the concentration of substances in sweat (e.g., sodium of 9 mmol/L) which is displayed on left side display 296 and sensor 300 supported by medial canthal pad 290 produces a signal indicative of, for example, brain temperature of 98 degrees F. which is displayed on the right side display 298. Sweat sensor can be porous or microporous in order to optimize fluid passage to sensors when measuring chemical components.

A variety of display means and associated lenses for proper focusing can be used including liquid crystal display, LEDs, fiber optic, micro-projection, plasma means, and the like. It is understood that display means can be attached directly to the lens or be an integral part of the lens. It is also understood that display means can include a separate portion contained in the lens rim or outside of the lens rim. Further, the two lenses and display 296, 298 held within the lens rims 293, 297 can be replaced with a single unit which can be attached directly to the frame of eyeglasses 292 with or without the use of lens rim 293, 297.

FIG. 27 is a perspective view of another preferred embodiment showing a three piece support structure 304 and preferably providing a medial canthal pad connecting piece 303 adapted as an interchangeable connecting piece. This embodiment comprises three pieces. Piece 301 comprises left lens rim 301a and left temple 301b. Piece 302 comprises right lens rim 302a and right temple 302b. Piece 303 called the medial canthal piece connector comprises the connecting bridge of eyeglasses 303a and the pad structure 303b of eyeglasses. Pad piece 303 is particularly adapted to provide medial canthal pads 306 for positioning a sensor 308 at the BTT site. In reference to this embodiment, the user can buy three piece eyeglasses in accordance with the invention in which the connector 303 has no sensing capabilities, and it is thus a lower cost. However, the three piece eyeglasses 304 offers the versatility of replacing the non-sensing connector 303 by a connector 303 with sensing capabilities. As shown in FIG. 27 connector 303 with medial canthal pads 306 and sensor 308 includes also radio frequency transmitter 310 and cell 312. Therefore, connector 303 provides all the necessary hardware including means for sensing, transmitting, and reporting the signal. Any means for attachment known in the art can be used including pressure means, sliding means, pins, and the like.

Another preferred embodiment, as shown in FIG. 28A, provides a removable medial canthal piece 314 supporting sensor 316. As shown, connecting bridge 320 of eyeglasses 318 are attached to medial canthal piece 314 in a releasable manner. Eyeglasses 318 further includes sweat sensor 322, 324 supported by front part 311 and transmitting means 326 supported by temple 313. Front part 311 of eyeglasses 318 defines a front brow portion and extends across the forehead of the wearer and contains sweat sensor 322, 324. Sweat fluid goes through membranes in the sensor 322, 324 and reaches an electrode with generation of current proportional to the amount of analyte found in the sweat fluid.

Figure 28B:
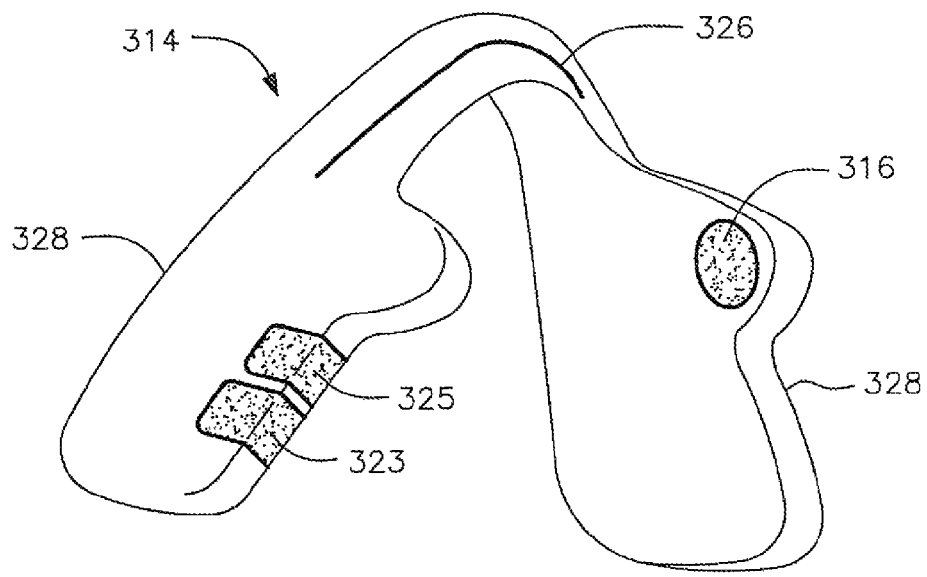
FIG. 28B is a rear perspective view of the removable medial canthal piece of FIG. 28A.
Figure 28C:
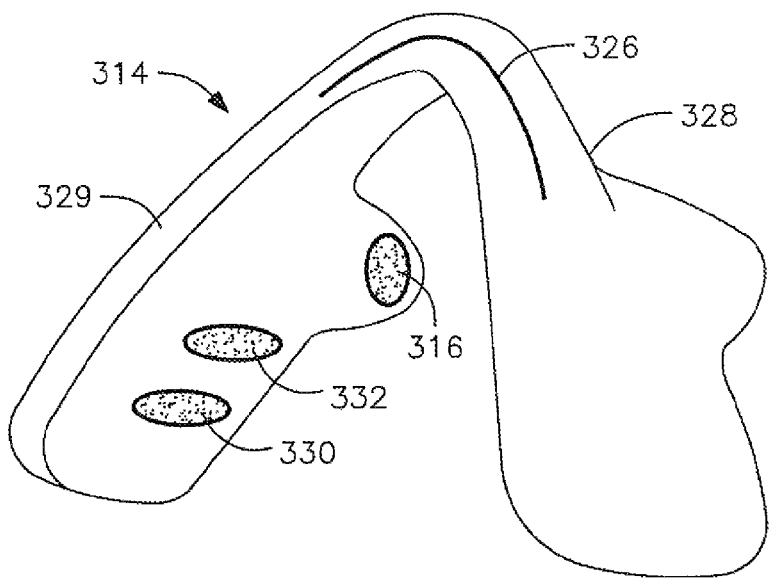
FIG. 28C is a front perspective view of the removable medial canthal piece of FIG. 28B.

FIG. 28B is a rear perspective view of the removable medial canthal piece 314 showing visual reporting means 323, 325 such as a green LED and a red LED in left arm 328 and sensor 316 adapted to be positioned at the end of the tunnel, and wire 326 for electrically connecting right arm 329 and left arm 328 of medial canthal piece 314. FIG. 28C is a front perspective view of the removable medial canthal piece 314 showing power source 330, transmitter 332 and sensor 316 in right arm 329 and wire 326 for electrically connecting right arm 329 and left arm 328 of medial canthal piece 314. Medial canthal piece 314 can be replaced by a non-sensing regular nose pad which would have the same size and dimension as medial canthal piece 314 for adequate fitting with connecting bridge 320 of eyeglasses 318 of FIG. 28A. The removable medial: canthal piece can have; besides LED, a built-in LCD display for displaying a numerical value and/or RF transmitter. Therefore, the removable medial canthal piece can have one or various reporting means integrated as a single sensing and reporting unit.

Figure 29:
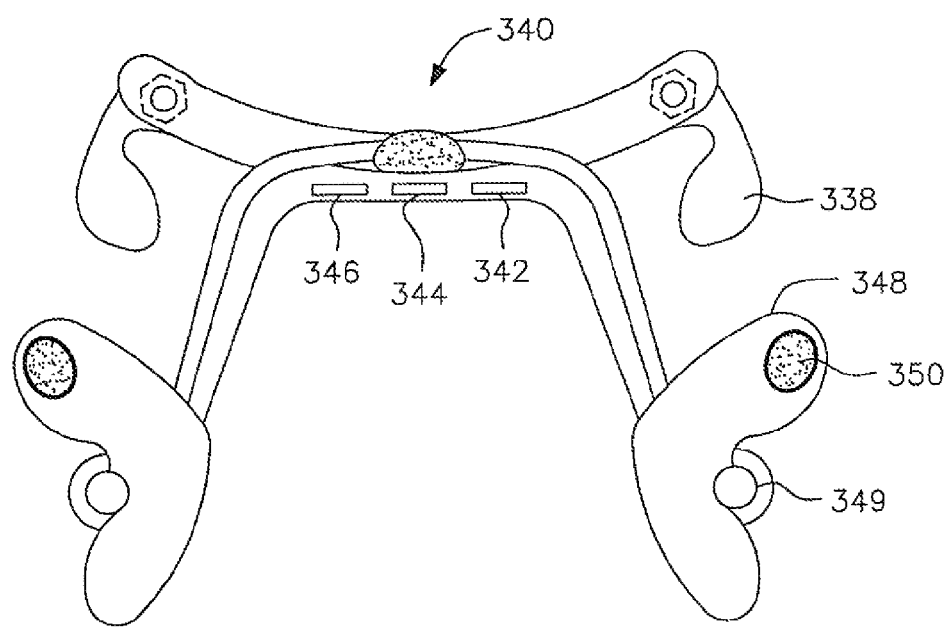
FIG. 29 is a rear perspective view of one preferred embodiment of a support structure incorporated as a clip-on for eyeglasses.

FIG. 29 is a rear perspective view of one preferred embodiment of a support structure incorporated as a clip-on 340 for eyeglasses and includes attachment means 338 such as a hook or a magnet, transmitting means 342, processing means 344, power source 346, medial canthal pad 348 mounted on a three axis rotatable structure 349 for proper positioning at the BTT site, and sensor 350. Clip-on 340 is adapted to be mounted on regular eyeglasses and to fit the medial canthal pad 348 above the regular nose pads of eyeglasses.

Figure 30:
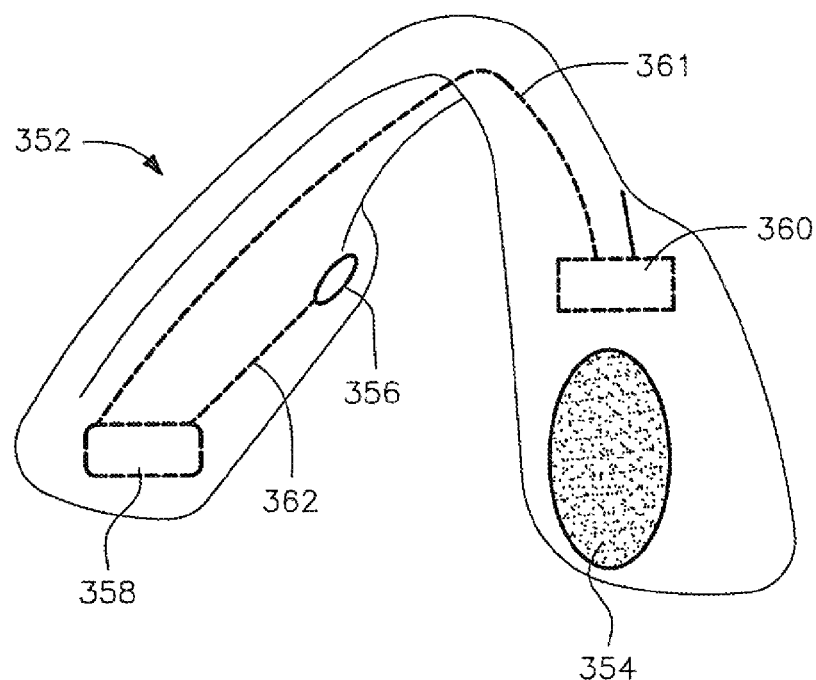
FIG. 30 is a perspective view of one alternative embodiment of a support structure with medial canthal pads that uses an adhesive backing for securing to another structure.

Sensing medial canthal pads can be preferably connected to attachment structure such as eyeglasses independent of the presence of specialized connecting or attachment means mounted in said eyeglasses such as grooves, pins, and the like. This embodiment provides means for the universal use of sensing medial canthal pads in any type or brand of attachment structure. FIG. 30 shows a front perspective view of medial canthal pads 352 comprising an adhesive backing 354 for securing pad 352 to an attachment structure such as eyeglasses or another support structure. Adhesive surface 354 is adapted to match an area of eyeglasses that allow securing medial canthal pad 352 to said eyeglasses, such as for instance the area corresponding to regular nose pads of eyeglasses. Medial canthal pad 352 works as a completely independent unit and contains sensor 356, power source 358 and reporting means 360 electrically connected by wire 361,362. Reporting means 360 include local reporting with visual means (e.g., LED), audio means (e.g., piezoelectric, voice chip or speaker) and remote reporting with wireless transmission.

Figure 31A:
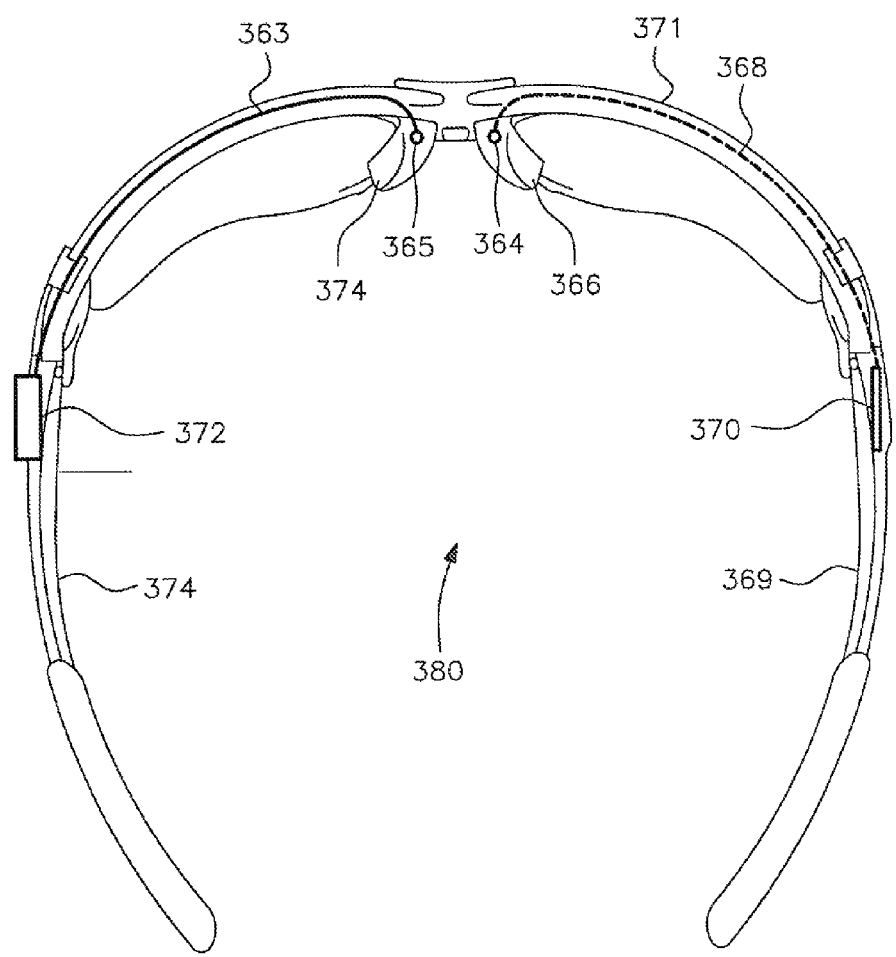
FIG. 31A is a top perspective view of one alternative embodiment of a support structure with holes for securing medial canthal pads.
Figure 31B:
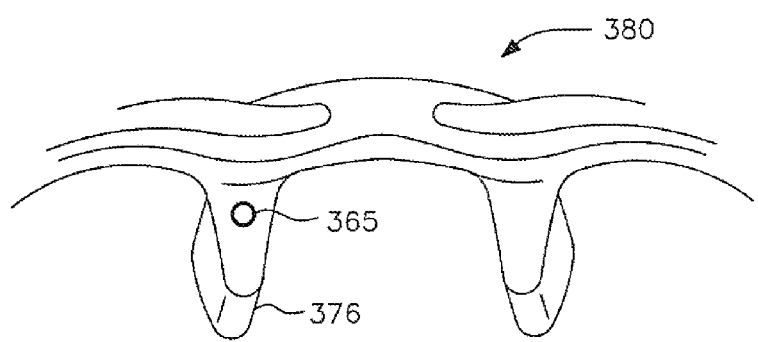
FIG. 31B is a magnified perspective view of part of the support structure of FIG. 31A.

FIG. 31A is a top perspective view of one alternative embodiment of a support structure incorporated as eyeglasses 380 with holes 364, 365 in regular nose pads 366, 376 for securing specialized medial canthal pads. Eyeglasses 380 includes wire 368 disposed within the right lens rim 371 of the frame of eyeglasses 380 with said wire 368 connecting transmitter 370 housed inside the right temple 369 to nose pad 366. Eyeglasses 380 further includes wire 363 mounted on top of left lens rim 365 with said wire 363 connecting transmitter 372 mounted on top of the left temple 374 to nose pad 376. FIG. 31B is a magnified perspective view of part of the support structure 380 with hole 365 in regular nose pad 376. FIG. 31C is a side perspective view of regular nose pad 366 with hole 364. FIG. 31D is a side perspective view of a medial canthal piece 382 secured to hole 364 of regular nose pad 366.

Figure 32A:
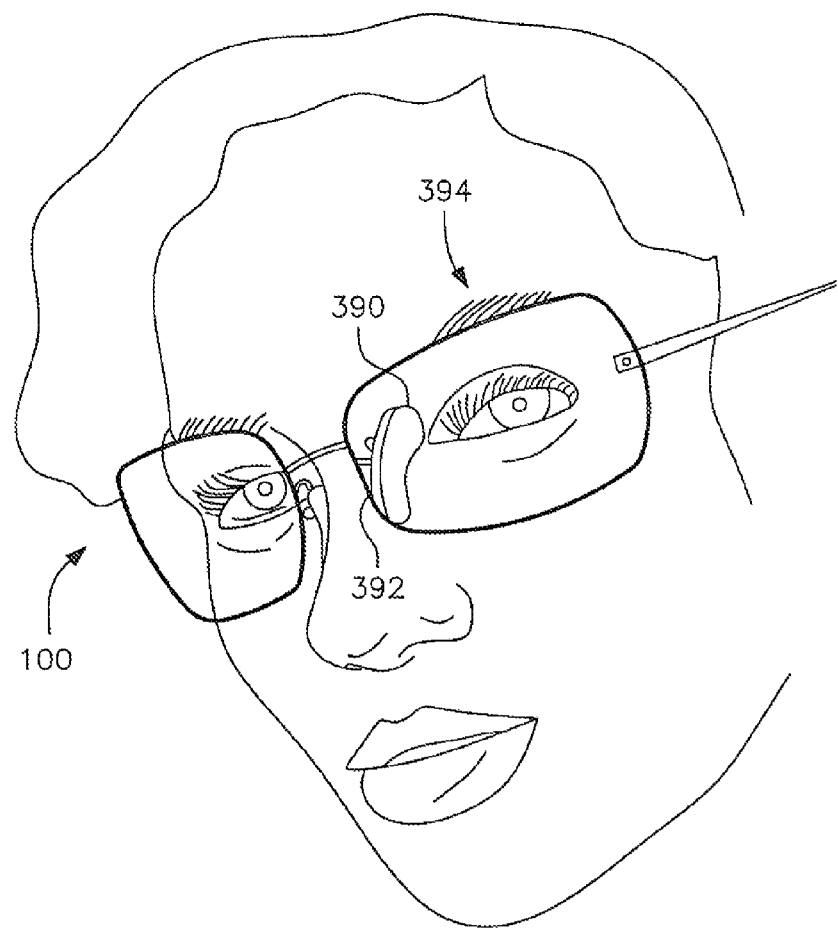
FIG. 32A is a perspective view of a person wearing a support structure comprised of medial canthal caps secured on top of a regular nose pad of eyeglasses.
Figure 32B:
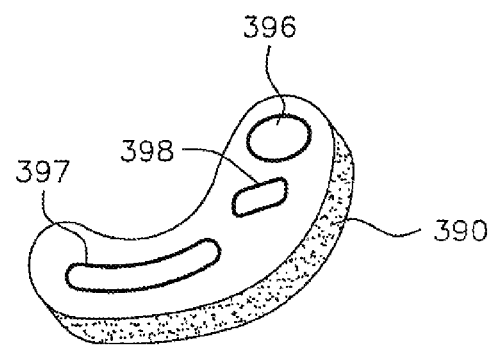
FIG. 32B is a perspective view of the medial canthal cap of FIG. 32A.

FIG. 32A is a perspective view of a person 100 wearing a support structure comprised of medial canthal caps 390 secured on top of a regular nose pad 392 of eyeglasses 394. FIG. 32B is a perspective rear view of the medial canthal cap 390 showing sensor 396, transmitter chip 398 and opening 397 for securing cap 390 to nose pads.

Figure 33A:
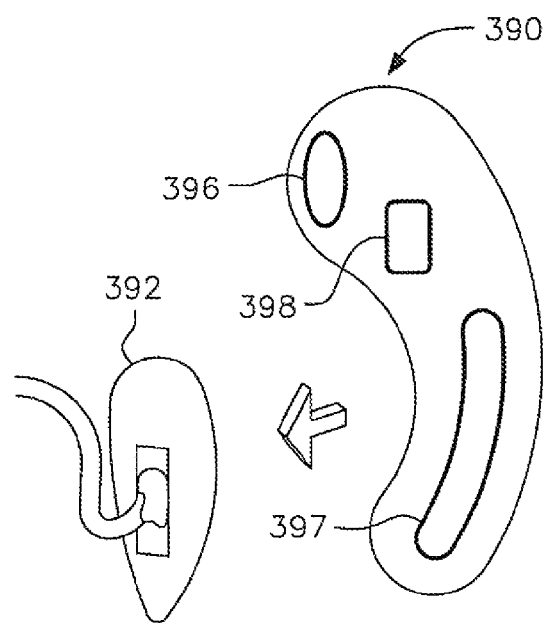
FIG. 33A is an exploded perspective view of a medial canthal cap being secured to the nose pad.
Figure 33B:
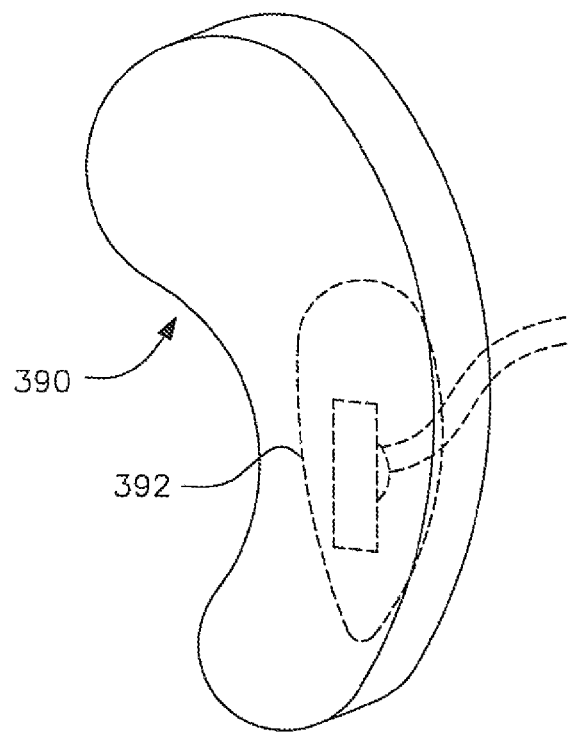
FIG. 33B is a perspective view of the end result of the medial canthal cap secured to the nose pad.

FIG. 33A is a perspective view of a medial canthal cap 390 being secured to the nose pad 392. Medial canthal cap 390 contains sensor 396, transmitter chip 398 and opening 397. FIG. 33B is a perspective view showing the end result of the medial canthal cap 390 secured to the nose pad 392.

Figure 34:
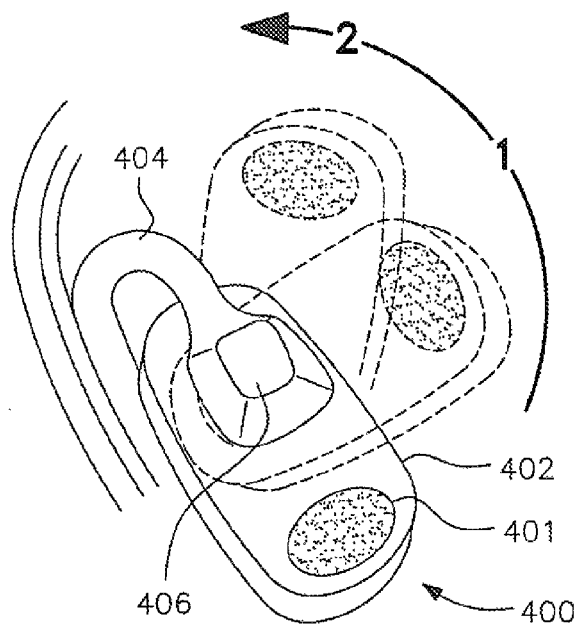
FIG. 34 is a perspective view of a modified rotatable nose pad to position a sensor on the skin at the end of the tunnel in accordance with the present invention.

Special nose pads are provided by the present invention for proper positioning a sensor at the BTT site. FIG. 34 is a perspective view of a modified left side rotatable nose pad 400 adapted to position a sensor on the skin at the end of the tunnel and includes nose pad 402 with sensor 401, arm 404, house 406 which houses a gear that allows rotation of a nose pad as a dial for positioning sensor 401 on different regions of the tunnel identified as 1 and 2. Position 1 places the sensor in line with the medial canthal corner and reaches the general area of the main entry point of the tunnel and position 2 places the sensor above the medial canthal corner right at the main entry point of the tunnel. This embodiment allows automated activation of the sensing system and takes advantage of the fact that the nose bridge is cold as seen in FIG. 1 (nose is dark) and FIG. 2 (nose is purple and blue). When the pad is in its resting position ("zero"), the sensor 401 rests in a cold place with temperature of 35.7° C. corresponding to the regular position of nose pads on the nose. In position "zero" the sensor is in Sleep Mode (temperature of 35.8° C. or less). Changing the sensor to a hot region such as the general area (position 1) or the main entry point (position 2) automatically activates the sensor which goes into Active Mode and start sensing function.

It is understood that numerous special nose pads and medial canthal pads can be used in accordance with the principles of the invention including a pivotal hinge that allows pads to be foldable in total or in part, self-adjusting pads using a spring, pivoting, sliding in a groove, and the like as well as self-adjusting mechanisms which are adaptable to anatomic variations found in different races. It is understood that the modified nose pads are preferably positioned high in the frame, most preferably by connecting to the upper part of the lens rim or within 6 mm from the upper edge of the lens rim.

A variety of materials can be used including materials with super-adherent properties to allow intimate apposition of sensing means to the BTT site. A variety of metallic wires exhibiting super-elastic properties can be used as the hinge assembly mechanism for allowing proper positioning of sensing means to the BTT site. Medial canthal pads can be made of a flexible synthetic resin material such as a silicon rubber, conductive plastic, conductive elastomeric material, metal, pliable material, and the like so that appropriate apposition to the BTT site at the medial canthal area and proper functioning is achieved. It is also understood that the medial canthal pads can exhibit elastic and moldable properties and include material which when stressed is able to remain in the stressed shape upon removal of the stress. Any type of rubber, silicone, and the like with shape memory can also be used in the medial canthal pads and modified nose pad.

By greatly reducing or eliminating the interfering constituents and providing a high signal to noise ratio with a sensor adapted to capture thermal radiation from the BTT, the present invention provide the means needed for accurate and precise measurement of biological parameters including chemical components in vivo using optical means such as infrared spectroscopy. Moreover, the apparatus and methods of the present invention by enhancing the signal allows clinical useful readings to be obtained with various techniques and using different types of electromagnetic radiation. Besides near-infrared spectroscopy, the present invention provides superior results and higher signal to noise ratio when using other forms of electromagnetic radiation such as for example mid-infrared radiation, radio wave impedance, photoacoustic spectroscopy, Raman spectroscopy, visible spectroscopy, ultraviolet spectroscopy, fluorescent spectroscopy, scattering spectroscopy and optical rotation of polarized light as well as other techniques such as fluorescent (including Maillard reaction, light induced fluorescence and induction of glucose fluorescence by ultraviolet light), calorimetric, refractive index, light reflection, thermal gradient, Attenuated Total Internal Reflection, molecular imprinting, and the like. A sensor adapted to capture thermal energy at the BTE (Brain Thermal Energy) tunnel site provides optimal means for measurement of biological parameters using electromagnetic means. The BTE tunnel is the physical equivalent to the physiologic BTT and is used herein to characterize the physics of the tunnel. The geometry and dimension on the skin surface are the same for the BTT and BTE tunnel.

The following characteristics of the BTE tunnel allow optimal signal acquisition. Skin at the end of the BTE tunnel is thin. With a thick skin radiation may fail to penetrate and reach the substance to be measured. Skin at the BTE tunnel is homogenous with constant thickness along its entire surface. Random thickness of skin as occurs in other skin areas prevent achieving the precision needed. The BTE tunnel has no fat. The intensity of the reflected or transmitted signal can vary drastically from patient to patient depending on the individual physical characteristics such as the amount of fat. A blood vessel in the end of the BTE is superficial, terminal and void of thermoregulatory shunts. In other parts of the skin the deep blood vessels are located deep and vary greatly in position and depth from person to person. The BTE tunnel has no light scattering elements covering its end such as bone, cartilage and the like. Thermal radiation does not have to go through cartilage or bone to reach the substance to be measured. The end of the BTE tunnel on the skin has a special but fixed geometry and is well demarcated by permanent anatomic landmarks. In other skin surfaces of the body, inconsistency in the location of the source and detector can be an important source of error and variability.

Far-infrared radiation spectroscopy measures natural thermal emissions after said emissions interact and are absorbed by the substance being measured. The present invention provides a thermally stable medium, insignificant number of interfering constituents, and a thin skin is the only structure to be traversed by the thermal emissions from the BTE tunnel before reaching the detector. Thus there is high accuracy and precision when converting the thermal energy emitted by the BTE tunnel into concentration of the substance being measured.

The natural spectral emission by BTE tunnel changes according to the presence and concentration of chemical substances. The far-infrared thermal radiation emitted follow Planck's Law and the predicted amount of thermal radiation can be calculated. Reference intensity is calculated by measuring thermal energy absorption outside the substance of interest band. The thermal energy absorption in the band of substance of interest can be determined via spectroscopic means by comparing the measured and predicted values at the BTE tunnel site. The signal is then converted to concentration of the substance measured according to the amount of thermal energy absorbed.

A sensor adapted to view the BTE tunnel provides means for measuring a substance of interest using natural brain far-infrared emissions emitted at the BTE tunnel site and for applying Beer-Lambert's law in-vivo. Spectral radiation of infrared energy from the surface of the BTE tunnel site corresponds to spectral information of chemical substances. These thermal emissions irradiated at 38 degrees Celsius can include the 4,000 to 14,000 nm wavelength range. For example, glucose strongly absorbs light around the 9,400 nm band. When far-infrared thermal radiation is emitted at the BTE tunnel site, glucose will absorb part of the radiation corresponding to its band of absorption. Absorption of the thermal energy by glucose bands is related in a linear fashion to blood glucose concentration in the thermally sealed and thermally stable environment present in the BTE tunnel.

The support structure includes at least one radiation source from infrared to visible light which interacts with the substance being measured at the BTE tunnel and a detector for collecting the resulting radiation.

The present invention provides method for measuring biological parameters comprising the steps of measuring infrared thermal radiation at the BTE tunnel site, producing output electrical signals representative of the intensity of the radiation, converting the resulting input, and sending the converted input to a processor. The processor is adapted to provide the necessary analysis of the signal to determine the concentration of the substance measured and for displaying the results.

The present invention includes means for directing preferably near-infrared energy into the surface of the skin at the end of the BTE tunnel, means for analyzing and converting the reflectance or back scattered spectrum into the concentration of the substance measured and support means for positioning the light source and detector means adjacent to the surface of the skin at the BTE tunnel site.

The present invention also provides methods for determining the concentration of a substance with said methods including the steps of directing electromagnetic radiation such as near-infrared at the skin at the BTE tunnel site, detecting the near-infrared energy radiated from said skin at the BTE tunnel site, taking the resulting spectra and providing an electrical signal upon detection, processing the signal and reporting concentration of the substance of interest according to said signal. The invention also includes means and methods for positioning the light sources and detectors in stable position and with stable pressure and temperature in relation to the surface to which radiation is directed to and received from.

The present invention further includes means for directing infrared energy through the nose using medial canthal pads, means for positioning radiation source and detector diametrically opposed to each other, and means for analyzing and converting the transmitted resulting spectrum into the concentration of the substance measured. The present invention also provides methods for measuring biological parameters with said methods including the steps of directing electromagnetic radiation such as near-infrared through the nose using medial canthal pads, collecting the near-infrared energy radiated from said nose, taking the resulting spectra and providing an electrical signal upon detection, processing the signal and reporting concentration of the substance measured according to said signal. The invention also includes means and methods for positioning the radiation sources and detectors in a stable position and with stable pressure and temperature in relation to the surface to which radiation is directed through.

The present invention yet includes means for collecting natural far-infrared thermal radiation from the BTE tunnel, means for positioning a radiation collector to receive said radiation, and means for converting the collected radiation from the BTE tunnel into the concentration of the substance measured. The present invention also provides methods for measuring biological parameters with said methods including the steps of using the natural far-infrared thermal emission from the BTE tunnel as the resulting radiation for measuring the substance of interest, collecting the resulting radiation spectra, providing an electrical signal upon detection, processing the signal and reporting the concentration of the substance measured according to said signal.

A drug dispensing system including an infusion pump can be activated according to the level of the substance measured at the BTE tunnel, for example insulin can be injected automatically as needed to normalize glucose levels as an artificial pancreas.

Any substance present in blood which is capable of being analyzed by electromagnetic means can be measured at the BTE tunnel. For example but not by way of limitation such substances can include exogenous chemicals such as drugs and alcohol as well as endogenous chemicals such as glucose, oxygen, lactic acid, cholesterol, bicarbonate, hormones, glutamate, urea, fatty acids, triglycerides, proteins, creatinine, aminoacids and the like. Values such as pH can also be calculated as pH can be related to light absorption using reflectance spectroscopy.

Figure 35:
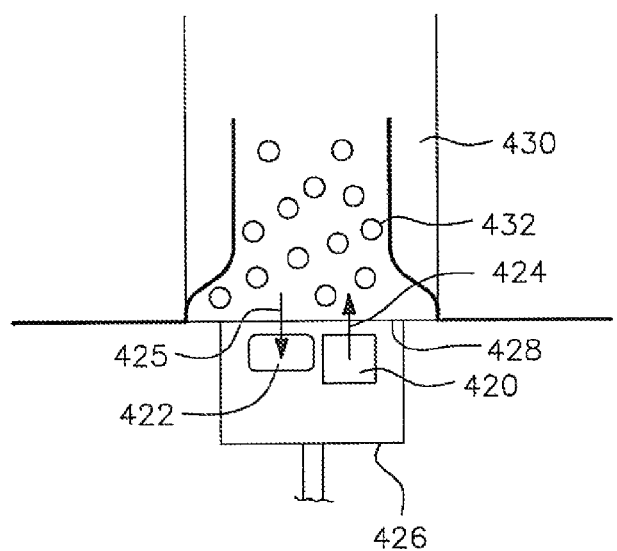
FIG. 35 is a schematic view of another preferred embodiment of the present invention using spectral reflectance.

In accordance with FIG. 35 a schematic view of one preferred reflectance measuring apparatus of the present invention is shown. FIG. 35 shows a light source 420 such as an infrared LED and a photodetector 422 located side-by-side and disposed within support structure 426 such as a medial canthal pad or modified nose pads of eyeglasses directing radiation 424 at the BTE tunnel 430 with said light source 420 laying in apposition to the skin 428 at the BTE tunnel 430. The light source 420 delivers the radiation 424 to the skin 428 at the BTE tunnel which is partially absorbed according to the interaction with the substance 432 being measured resulting in attenuated radiation 425. Part of the radiation 424 is then absorbed by the substance 432 and the resulting radiation 425 emitted from BTE tunnel 430 is collected by the photodetector 422 and converted by a processor into the blood concentration of the substance 432. Thin skin 428 is the only tissue interposed between radiation 424, 425 and the substance 432 being measured. The concentration of the substance 432 is accomplished by detecting the magnitude of light attenuation collected which is caused by the absorption signature of the substance being measured.

Infrared LEDs (wavelength-specific LEDs) are the preferred light source for this embodiment because they can emit light of known intensity and wavelength, are very small in size, low-cost, and the light can be precisely delivered to the site. The light source 420 emits preferably at least one near-infrared wavelength, but alternatively a plurality of different wavelengths can be used. The light source emits radiation 424, preferably between 750 and 3000 nm, including a wavelength typical of the absorption spectrum for the substance 432 being measured. The preferred photodetector includes a semiconductor photodiode with a 400 micron diameter photosensitive area coupled to an amplifier as an integrated circuit.

Figure 36:
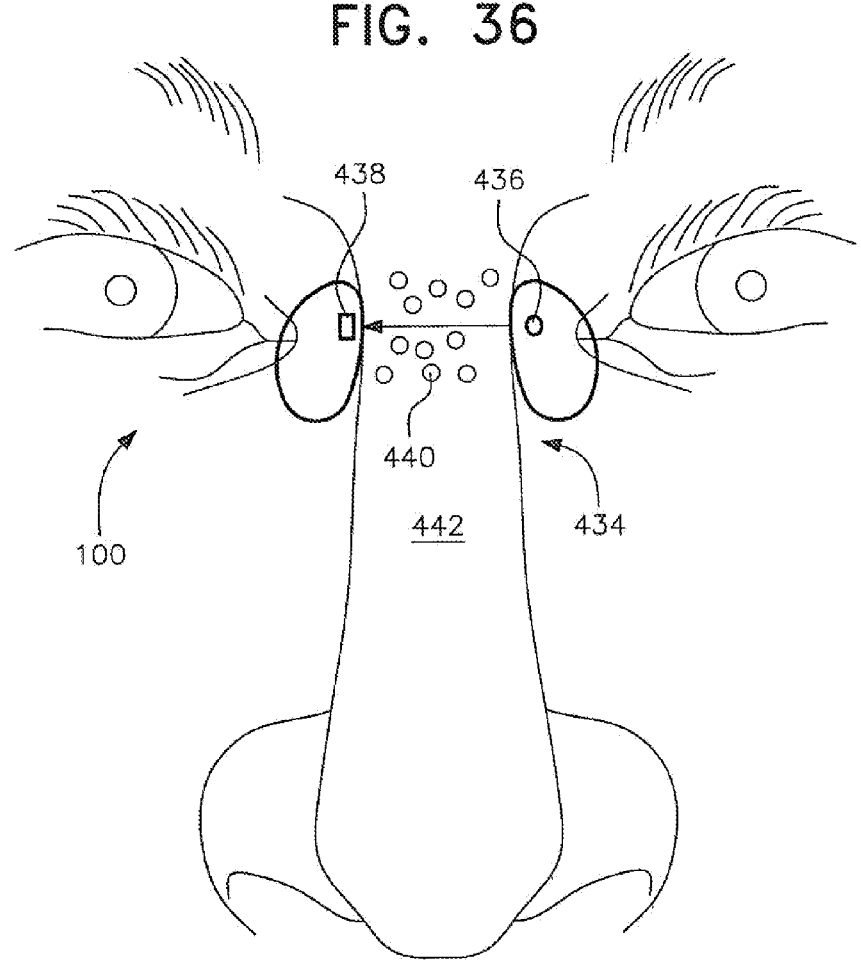
FIG. 36 is a schematic view of a person showing another preferred embodiment in accordance with the present invention using spectral transmission.

FIG. 36 shows a schematic view of a person 100 wearing a support structure 434 and light source 436 and detector 438 adapted to measure biological parameters using spectral transmission means. The light source 436 and photodetector 438 are positioned diametrically opposed to each other so that the output of the radiation source 436 goes through the nasal interface 442 containing the substance 440 being measured before being received by the detector 438. Photodetector 438 collects the resulting transmitted radiation which was directed through the nasal interface 442. A variety of LEDs and optical fibers disposed within the support structure 434 such as the medial canthal pads, nose pads and frames of eyeglasses are preferably used as a light delivery for the light source 436 and the light detector 438.

Arms of support structures 434 such as medial canthal pads are moveable and can be adjusted into different positions for creating fixed or changeable optical path. Preferred substances measured include oxygen and glucose. The brain maintains constant blood flow, whereas flow in extremities change according to cardiac output and ambient conditions. The oxygen levels found in the physiologic tunnel reflects central oxygenation. The oxygen monitoring in a physiologic tunnel is representative of the general hemodynamic state of the body. Many critical conditions such as sepsis (disseminated infection) or heart problems which alter perfusion in most of the body can be monitored. Oxygen in the BTE tunnel can continuously monitor perfusion and detect early hemodynamic changes.

Figure 37:
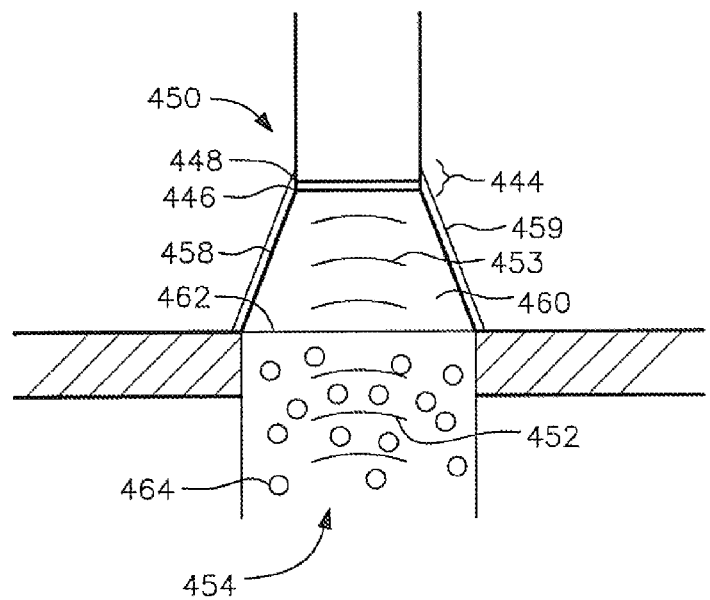
FIG. 37 is a schematic cross-sectional view of another preferred embodiment of the present invention using thermal emission.

FIG. 37 is a schematic cross-sectional view of another preferred embodiment of the present invention using thermal emission from the BTE tunnel. FIG. 37 shows a support structure 450 housing a thermal infrared detector 444 which has a filter 446 and a sensing element 448 with said sensing element 448 being preferably a thermopile and responding to thermal infrared radiation 452 naturally emitted by the BTE tunnel 454. The support structure 450 is adapted to have sensing means 448 with a field of view that corresponds to the geometry and dimension of the skin 462 at the end of the BTE tunnel 454. Support structure 450 provides walls 456, 458 which are in contact with the skin 462 with said walls creating a cavity 460 which contains thermal radiation 453 which has already passed through thin skin 462.

For example in the thermally sealed and thermally stable environment in the BTE tunnel 454, at 38° Celsius spectral radiation 453 emitted as 9,400 nm band is absorbed by glucose in a linear fashion according to the amount of the concentration of glucose due to the carbon-oxygen-carbon bond in the pyrane ring present in the glucose molecule. The resulting radiation 453 is the thermal emission 452 minus the absorbed radiation by the substance 464. The resulting radiation 453 enters the infrared detector 444 which generates an electrical signal corresponding to the spectral characteristic and intensity of said resulting radiation 453. The resulting radiation 453 is then converted into the concentration of the substance 464 according to the amount of thermal energy absorbed in relation to the reference intensity absorption outside the substance 464 band.

The same principles disclosed in the present invention can be used for near-infrared transmission measurements as well as for continuous wave tissue oximeters, evaluation of hematocrit, blood cells and other blood components. The substance measured can be endogenous such as glucose or exogenous such as alcohol and drugs including photosensitizing drugs.

Figure 38:
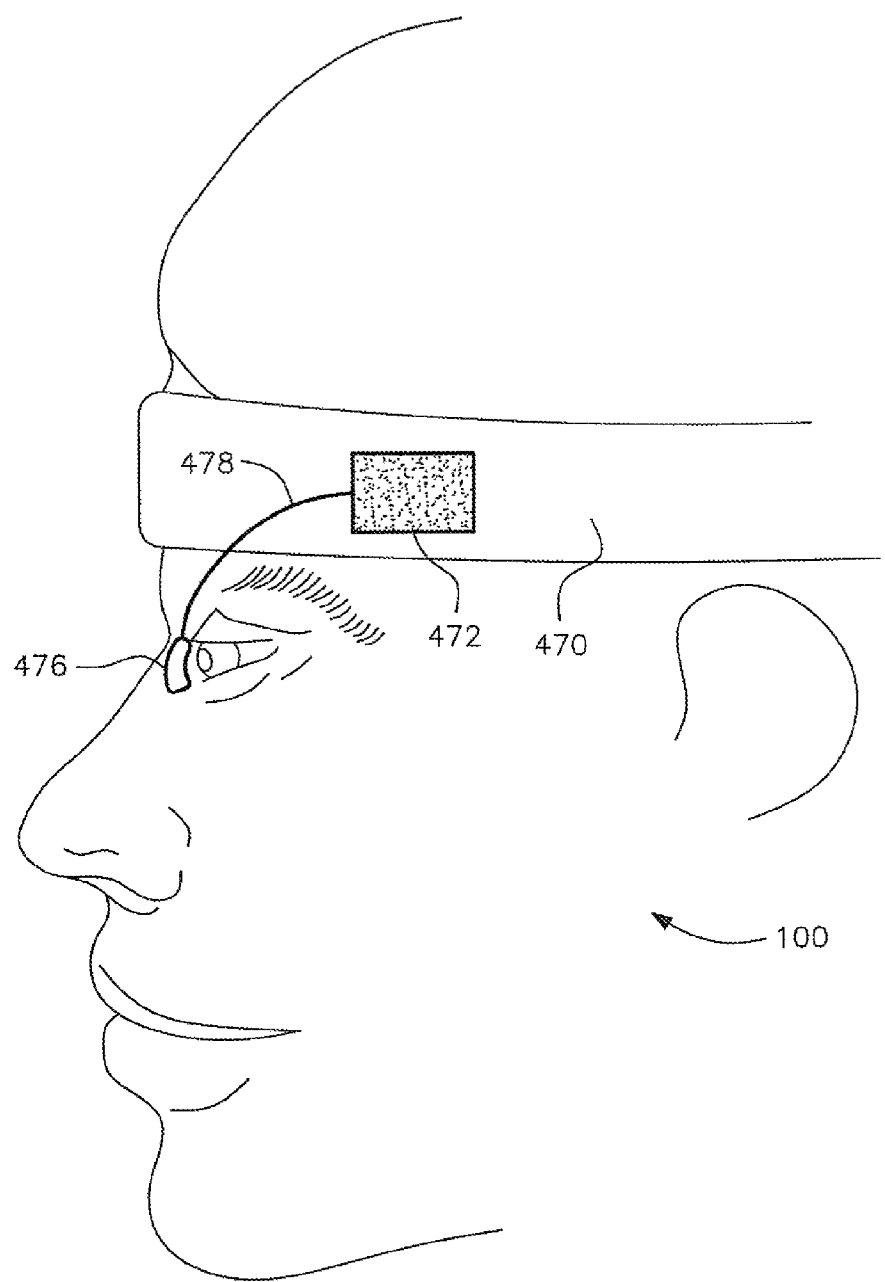
FIG. 38 is a side perspective view of an alternative embodiment using head mounted gear as a support structure.

Numerous support structures can position sensors at the BTT site for measuring biological parameters. Accordingly, FIG. 38 is a side perspective view of an alternative embodiment showing a person 100 using head mounted gear 470 as a support structure positioning with wires 478 and sensor 476 on the skin at the BTT site. A microelectronic package 472 containing transmitting means, processing means, and power source is disposed within or mounted on head band 470, with said head band 470 providing wire 478 from microelectronic package 472 for connection with sensing means 476 on the skin at the BTT site.

It is understood that the sensing means can be an integral part of the support structure or be connected to any support structures such as using conventional fasteners including screw, pins, a clip, a tongue-groove relationship, interlocking pieces, direct attachment, adhesives, mechanical joining, and the like; and said support structures include patches, clips, eyeglasses, head mounted gear, and the like.

Figure 39:
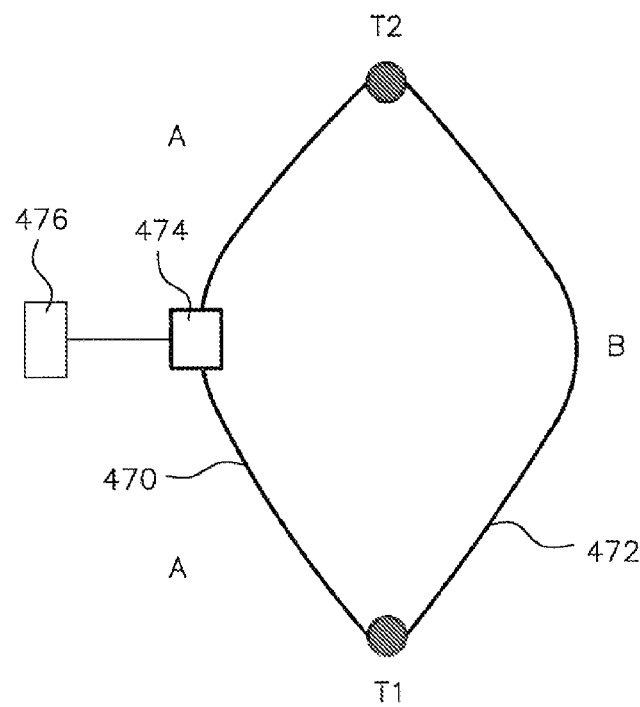
FIG. 39 is a schematic diagram of a preferred embodiment for generating thermoelectric energy to power the sensing system.

Various means to provide electrical energy to the sensing system were disclosed. The BTE tunnel offers yet a new way for natural generation of electrical energy. Accordingly, FIG. 39 is a schematic diagram of a preferred embodiment for generating thermoelectric energy from the BTE tunnel to power the sensing system. The generator of the invention converts heat from the tunnel into electricity needed to power the system. A thermoelectric module is integrated into the support structure to power the sensing system. The thermoelectric module preferably includes a thermopile or a thermocouple which comprises dissimilar metallic wires forming a junction. As heat moves from the tunnel through the thermoelectric module an electric current is generated. Since the BTE tunnel is surrounded by cold regions, the Seebeck effect can provide means for generating power by inducing electromotive force (emf) in the presence of a temperature gradient due to distribution of electric charges at the surface and interface of the thermoelectric circuit generated by the temperature at the BTE tunnel.

Accordingly, FIG. 39 shows the junctions T1 and T2 of metallic wire A 470 and metallic wire B 472 kept at different temperatures by placing junction T1 at the main entry point of the tunnel and junction T2 in a cold area such as the nose bridge (denoted in blue or purple in FIG. 1B, and referred herein as blue-purple nose). Metallic wires A 470 and B 472 are made of different materials and electric current flows from the hot to the cold region due to the thermal gradient with a magnitude given by the ratio of the thermoelectric potential. The potential U is given by $U=(Q_a-Q_b)*(T_1-T_2)$, where $Q_a$ and $Q_b$ denote the Seebeck coefficient (thermoelectric power) of metal A and metal $B_2$ and $T_1$ denotes temperature at the entry point of the BTE tunnel and $T_2$ denotes temperature at the blue-purple nose. The thermoelectric potential generated can power the sensing system and a capacitor 474 inserted into the system can be used to collect and store the energy and MCU 476 is adapted to controls the delivery of energy as needed for measuring, processing and transmitting the signal.

It is understood that other means to convert thermal energy from the BTE tunnel into electricity can be used. It is also understood that the surface of the eye and caruncle in the eye can provide a thermal gradient and Seebeck effect, however it is much less desirable than using the skin at the end of the BTE tunnel since hardware and wires touching the surface of the eye and/or coming out of the eye can be quite uncomfortable and cause infection.

Contrary to that numerous support structures disclosed in the present invention including eyeglasses can easily be adapted to provide in an unobtrusive manner the power generating system of the invention, for example by using a support structure such as eyeglasses for positioning the hot junction at the BTE site using medial canthal pads and positioning the cold junction on the nose using regular nose pads of eyeglasses. It is also understood that although the power generating system using Brain Thermal Energy was designed for powering the sensing system of the present invention, any other electrical device could be adapted to be supplied with energy derived from the Brain Thermal Energy tunnel.

Additional embodiments include support structures to position the sensor at the BTT site of animals. Many useful applications can be achieved, including enhancing artificial insemination for mammalian species by detecting moment of ovulation, monitoring herd health by continuous monitoring of brain temperature, detection of parturition and the like.

Figure 40:
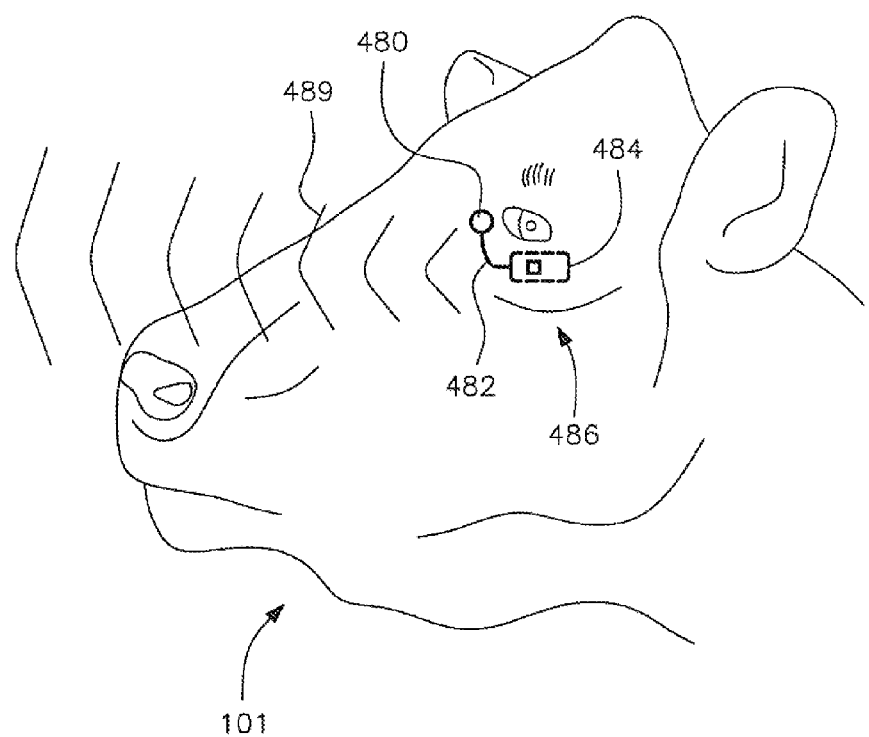
FIG. 40 is a perspective view of a preferred embodiment for animal use.

Accordingly, FIG. 40 is a perspective view of a preferred embodiment showing an animal 101 with sensor 480 positioned at the BTT site with wire 482 connecting sensor 480 with a microelectronic package 484 containing transmitting means, processing means, and power source in the eyelid pocket 486 of animal 101. Signal from microelectronic package 484 is preferably transmitted as radio waves 489. The signal from the transmitter in package 484 can be conveyed to a GPS collar allowing the identification of the animal having a high temperature associated with the localization of said animal by GPS means. Whenever there is an increase in brain temperature identified by the sensing means 480, the signal of high temperature activates the GPS collar to provide the localization of the affected animal. Alternatively the remote radio station receiving waves 489 activate the GPS system when the abnormal signal is received. In this case, the transmitter in package 484 only sends the signal to the remote station, but not to the GPS collar.

Figure 41A:
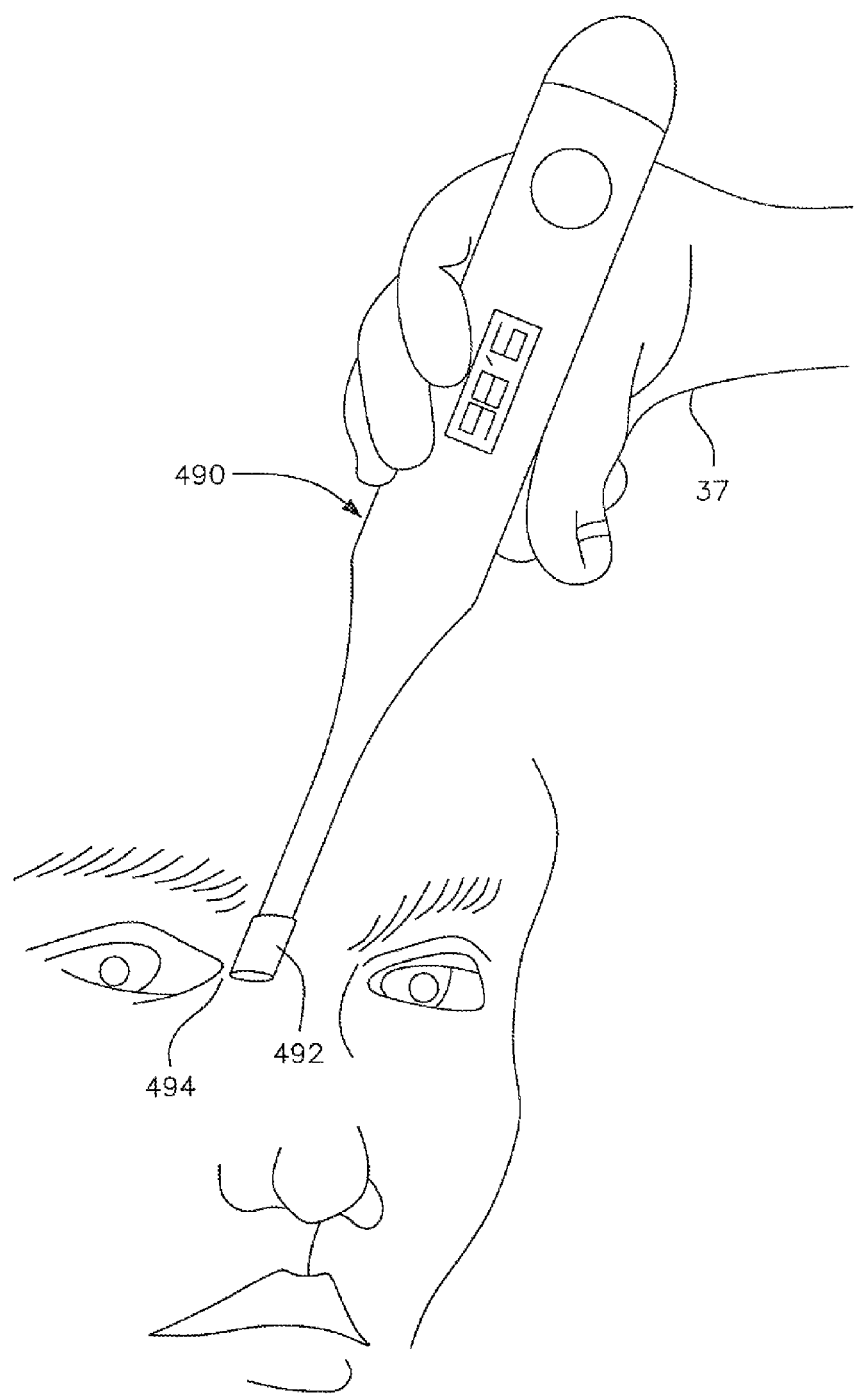
FIGS. 41A and 41B are perspective views of an alternative embodiment of a portable support structure with a sensor positioned at the tunnel.
Figure 41B:
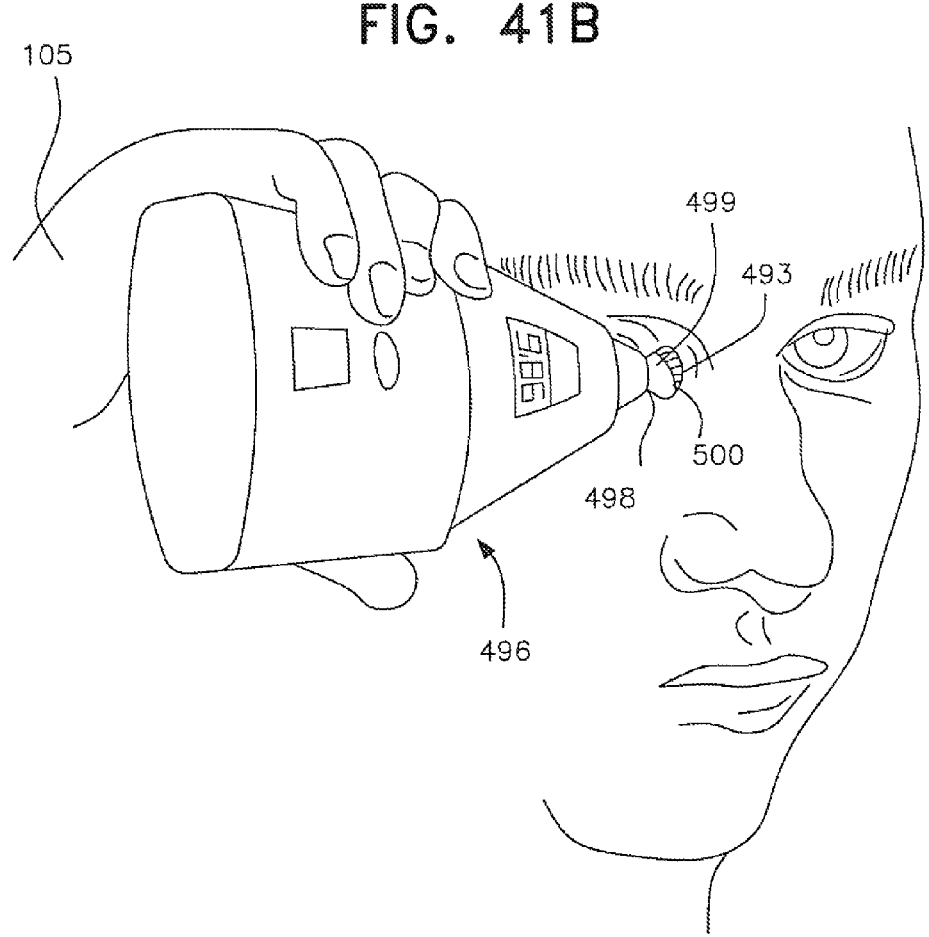

FIG. 41A is a perspective view of a portable support structure 490 positioning sensor 492 in contact with the skin 494 at the BTT site for measuring biological parameters. Support structure 490 incorporated as a thermometer with a contact sensor 492 is held by a second person 17 for positioning the sensor 492 on the skin 494 and performing the measurement. FIG. 41B is a perspective view of a portable support structure 496 with walls 500 positioning non-contact sensor 498 such as a thermopile with a field of view that matches in total or in part the geometry and dimension of the skin area at the end of the BTT. Support structure 496 incorporated as an infrared thermometer is held by a second person 105 for positioning the sensor 498 and measuring biological parameters. Although it is understood that pointing an infrared detector to the BTT site can be used in accordance with the invention, the temperature measured is not as clinically useful because of the ambient temperature. Therefore, the support structure 496 contains walls 500 that create a confined environment for thermal radiation to reach sensor 498 from the skin over the tunnel. Walls 500 of the support structure are adapted to match the geometry of the tunnel and to provide a cavity 499 with the boundaries consisting of the sensor surface 492 and the skin area 493 viewed by said sensor 498, in a similar manner as described for FIG. 37.

It is also understood that many variations are evident to one of ordinary skill in the art and are within the scope of the invention. For instance, one can place a sensor on the skin at the BTT site and subsequently place an adhesive tape on top of said sensor to secure the sensor in position at the BTT site. Thus in this embodiment the sensor does not need to have an adhesive surface nor a support structure permanently connected to said sensor.

It is understood that any electrochemical sensor, thermoelectric sensor, acoustic sensor, piezoelectric sensor, optical sensor, and the like can be supported by the support structure for measuring biological parameters in accordance with the principles of the invention. It is understood that sensors using amperometric, potentiometric, conductometric, gravimetric, impedimetric, systems, and the like can be used in the apparatus of the invention for the measurement of biological parameters. It is also understood that other forms for biosensing can be used such as changes in ionic conductance, enthalpy, and mass as well as immunobiointeractions and the like.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A method of warning for thermal damage by thermal radiation in an individual exposed to said thermal radiation, said method comprising the steps of measuring temperature of said individual by measuring radiation emitted at a brain temperature tunnel, the location of measurement of the radiation being at the brain temperature tunnel located between an eyebrow and an eye of the individual on the skin at the end of the brain tunnel the radiation being detected by a sensor at said brain temperature tunnel located between the eyebrow and the eye of the individual, analyzing the measured temperature by comparing the measured temperature to a predetermined temperature by a microprocessor to determine whether the measured temperature fits a predetermined criteria of an elevated temperature capable of developing thermal damage to the brain, and notifying said individual of said condition by a warning device.

2. A method of enhancing safety and performance of an individual during physical activity, said method comprising the steps of measuring brain temperature by measuring radiation emitted at a brain temperature tunnel, the location of measurement of the radiation being at the brain temperature tunnel located between an eyebrow and an eye of the individual on the skin at the end of the brain tunnel, the radiation being detected by a sensor at said brain temperature tunnel located between the eyebrow and the eye of the individual, and determining a type, amount and time of fluid intake necessary for the individual to lower brain temperature according to a predetermined criteria of elevated brain temperature based on said measured brain temperature by comparison by a processor of the actual brain temperature and the predetermined criteria of elevated brain temperature so as to enhance safety and performance during said physical activity by avoiding conditions of elevated brain temperature of the individual.

3. A physical activity management device comprising a housing for placement adjacent to the skin at the end of a brain temperature tunnel, a temperature sensor contained in the housing being spaced by said housing so as to produce a field of contact of said temperature sensor for measuring signals produced on said skin at the end of the brain tunnel, said housing including at least one of a patch, a clip, a medial canthal pad, a modified nose pad, head mounted gear and a contact structure, a processor determining a thermal state of the body of said individual from said individual's measured brain temperature as measured by the temperature sensor at the brain temperature tunnel located between an eyebrow and an eye of the individual, and a reporting device signaling to said individual when said thermal state is above a predetermined value so as to warn the individual against elevated detrimental temperature conditions of the brain as measured at the brain temperature tunnel located between the eyebrow and the eye of the individual that would adversely affect the individual due to elevated brain temperature above the predetermined value.

* * * * *